(12) United States Patent
Gupta et al.

(10) Patent No.: US 9,765,350 B2
(45) Date of Patent: Sep. 19, 2017

(54) **METHODS AND COMPOSITIONS FOR RECOMBINATION A GENE-DEFICIENT STRAINS OF *AGROBACTERIUM TUMEFACIENS***

(71) Applicant: Dow AgroSciences LLC, Indianapolis, IN (US)

(72) Inventors: Manju Gupta, Carmel, IN (US); Sara Bennett, Indianapolis, IN (US); Sandeep Kumar, Carmel, IN (US); Donald Merlo, Carmel, IN (US); Nagesh Sardesai, West Lafayette, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/844,731

(22) Filed: Sep. 3, 2015

(65) Prior Publication Data

US 2016/0068851 A1    Mar. 10, 2016

Related U.S. Application Data

(60) Provisional application No. 62/045,947, filed on Sep. 4, 2014.

(51) Int. Cl.
*C12N 15/82* (2006.01)
*C12N 15/74* (2006.01)

(52) U.S. Cl.
CPC ....... *C12N 15/8205* (2013.01); *C12N 15/743* (2013.01)

(58) Field of Classification Search
None
See application file for complete search history.

(56) References Cited

U.S. PATENT DOCUMENTS

| 3,868,730 A | 3/1975 | Kaufer et al. |
| 4,249,270 A | 2/1981 | Bahler |
| 5,147,405 A | 9/1992 | Van Zile et al. |
| 6,117,175 A | 9/2000 | Bosredon |
| 2004/0220675 A1 | 11/2004 | Lewis et al. |
| 2011/0137619 A1 | 6/2011 | Otto et al. |

OTHER PUBLICATIONS

Farrand et al 1989 (Journal of Bacteriology October: p. 5314-5321).*
Wood et al 2014 (Genbank accession No. AE007869.2).*
Hamilton et al 1996 (PNAS 93: p. 9975-9979).*

* cited by examiner

*Primary Examiner* — Matthew Keogh
(74) *Attorney, Agent, or Firm* — Yung H. Lee; Barnes & Thornburg LLP

(57) ABSTRACT

The present disclosure provides novel compositions and methods for the production and use of *Agrobacterium tumefaciens* strains (for example LBA4404) that are deficient in RecA activity relative to the parent strain. Combinations with other gene-deficient-strains of *Agrobacterium tumefaciens* are also disclosed. Specifically, two exemplary s recA minus strains, UIA777 where chloramphenicol resistant gene disrupting the recA gene and UIA770 where kanamycin resistant gene disrupting the recA gene are provided.

7 Claims, 4 Drawing Sheets

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 1
ggcattcttg gcatagtggt                                              20

<210> SEQ ID NO 2
<211> LENGTH: 20
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 2
gctgaagcca gttaccttcg                                              20

<210> SEQ ID NO 3
<211> LENGTH: 34
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 3
ccggatcccc gcgttccagc gtcttgcgga aacg                              34

<210> SEQ ID NO 4
<211> LENGTH: 36
<212> TYPE: DNA
<213> ORGANISM: Artificial Sequence
<220> FEATURE:

<223> OTHER INFORMATION: Primer used to identify and isolate the recA
      gene from A. tumefaciens

<400> SEQUENCE: 4
ccggatccgg atagggcatg ccgtgggtga tgatgg                          36

<210> SEQ ID NO 5
<211> LENGTH: 23
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 5
cgttccagcg tcttgcggaa acg                                       23

<210> SEQ ID NO 6
<211> LENGTH: 21
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 6
ccgtttcagt ctcgatcatg c                                         21

<210> SEQ ID NO 7
<211> LENGTH: 23
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 7
gcattggtga acatcagtgt cgg                                       23

<210> SEQ ID NO 8
<211> LENGTH: 63
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 8
ccaccggacg cgaacgcccg gaccttcgaa tgcatcagcc ctcgtgtagg ctggagctgc   60
ttc                                                                63

<210> SEQ ID NO 9
<211> LENGTH: 63
<212> TYPE: DNA
<213> ORGANISM: Artificial Sequence
<220> FEATURE:
<223> OTHER INFORMATION: Primer used to identify and isolate the recA
      gene from A. tumefaciens

<400> SEQUENCE: 9
cctgtgcggc ttcaataacc taaggtgga tcggatggca caacatatga atatcctcct   60
tag                                                                63

<210> SEQ ID NO 10
<211> LENGTH: 1092

```
<212> TYPE: DNA
<213> ORGANISM: Agrobacterium tumefaciens

<400> SEQUENCE: 10
atggcacaaa attctttgcg tctcgtagag gataaatcgg tggataaaag caaggcactg      60
gaagcggcgc tctcccagat cgaacggtcg ttcggcaagg gatcgatcat gaagctcggt     120
tccaatgaaa acgtggttga agtagagacc atttcgacgg ttctctcag cctggatata     180
gcgctcggta tcggcggcct gccgaagggg cgtatcgttg agatttacgg cccggaaagc     240
tccggtaaga cgacgcttgc gttgcagacg atcgcggaag cccagaaaaa gggcggcatc     300
tgcgccttcg tggatgccga gcacgcgctc gatccggtct atgcccgcaa gctcggtgtg     360
gatttgcaga accttctgat ctcgcagccg gatacgggcg agcaggcgct tgaaatcacc     420
gatacgctgg tgcgctccgg tgccgtcgac attctggtcg tggactcggt tgcggcgctg     480
acgccgcgtg ccgaaatcga aggcgagatg ggtgacagcc tgccgggcct tcaggcacgt     540
ctgatgagcc aggcgctgcg caagctgacc gcctcgatct ccaagtcgaa gtgcatggtg     600
atcttcatca accagatccg catgaagatc ggcgtcatgt tcggttcgcc ggaaacgacg     660
acgggcggta tgcgcttaa attctacgcc tcggtgcgtc tcgacattcg ccgtatcggc     720
gccgtcaagg agcgtgaaga ggttgtcggc aaccagaccc gcgtcaaggt cgtcaagaac     780
aagatggcac cgccttcaa gcaggtggaa ttcgacatca tgtatggtga aggcgtttcc     840
aagaccggcg agcttgtcga tctcggcgtg aaagccggta tcgtcgagaa atccggtgca     900
tggttctcct ataacagcca gcgtttgggg caggggcgtg aaaatgccaa gactttcctg     960
cgcgacaatc cggaaatggc aagcgagatc gaactggcgc tgcgccagaa cgccggtctg    1020
atcgccgatc ggttcctgca gaatggcggc ccggaagctg gcgaaagcga cgacggtccc    1080
gacgagggct ga                                                         1092

<210> SEQ ID NO 11
<211> LENGTH: 3680
<212> TYPE: DNA
<213> ORGANISM: Agrobacterium tumefaciens

<400> SEQUENCE: 11
agcgcgacga tcggcgcgcc gcgctgtttg gcagcggcaa cctcttgcga atagatgatg      60
gttaggagcg gggagatggg gcgggtcatt ctgtttgttc cagactataa aaaacgggt     120
tcatgccagc atttcggcct tggggacaag ccccaacatg gtctcgacac tgtcttttga     180
caggtcttgg gcggtggcga aaggcgattg cacggtgatg gcggccgccg cggcaccaa     240
tcgcagggcc tcagtgatgg ctttgccctc cgtaatcgcc gcgagataac ctgacgccat     300
ggcgtctccg gccccggtta cgtctttcac ctcgcggatg atgggtgggt ggaggcttgc     360
ggtttgcgtc gcgttgaagg ctaccacttc gcttgcgcca cgggtgatga cgccgccggc     420
aaggcctgcc ctgcggagaa tgcccggcca gtcgcgaaca ttgtctgccg tctgtccggt     480
cagcgcgcgc gcctctgcct ggttcatgaa gagaatgtcg atatcggcga gcatgtcctt     540
cagcttcacc gccttggcgg gcgaaatggc gatggccgcg agcggctttt ggcaggcgcg     600
ggcaatgaga ccgagcgcct tcaacgtatc ctccggcaga ttggcatcgc aaagcagaag     660
gtcgctcgcg gtaatcgctt cacgcaccgc gcgaactttg aggcggcgcg gcgaaaacag     720
cttgtaaagg tccatatccg caagtgcgat gacaagattg ccgtcgcgct ccagaatggc     780
ggtgtagctt ggcgtgcggc gatcgaggaa aacgaagggc gtatcttcca cgcccgcctg     840
```

```
ccttgctgcc tctgccaccg cttcgccggt cacgtcgccg ccgcgcggtg cgatgatacg      900
gacggcaaaa ccgagccggg aaagattgcg cgccgcattg aaaccgccgc cgccagcctc      960
ttccatccat gagccaggat tgctgggcgc cgggcgccgt ttcagtctcg atcatgccgc     1020
gcctgtcata tgcgcgccgc ccagaacgag tatcttcttc acgcttgtgt ttccctcttt     1080
cgcggatgga aaggtggacg gattcgtccc aatcttctgt tgttcccct tcacatccgg      1140
ttcgcagcga taggccggac acggaaaaac gaaagcagaa caaaccactt atcgctattt     1200
gttttcaata tgctggctgc gccttgcgat atgagaacaa atagagtaca tcctatttcc     1260
atactgcttc attgcctgtg cggcttcaat aacctaaagg tggatcggat ggcacaaaat     1320
tctttgcgtc tcgtagagga taaatcggtg ataaaagca aggcactgga agcggcgctc      1380
tcccagatcg aacggtcgtt cggcaaggga tcgatcatga agctcggttc caatgaaaac     1440
gtggttgaag tagagaccat ttcgacgggt tctctcagcc tggatatagc gctcggtatc     1500
ggcggcctgc cgaaggggcg tatcgttgag atttacggcc cggaaagctc cggtaagacg     1560
acgcttgcgt tgcagacgat cgcggaagcc cagaaaaagg gcggcatctg cgccttcgtg     1620
gatgccgagc acgcgctcga tccggtctat gcccgcaagc tcggtgtgga tttgcagaac     1680
cttctgatct cgcagccgga tacgggcgag caggcgcttg aaatcaccga tacgctggtg     1740
cgctccggtg ccgtcgacat tctggtcgtg gactcggttg cggcgctgac gccgcgtgcc     1800
gaaatcgaag gcgagatggg tgacagcctg ccgggccttc aggcacgtct gatgagccag     1860
gcgctgcgca agctgaccgc ctcgatctcc aagtcgaagt gcatggtgat cttcatcaac     1920
cagatccgca tgaagatcgg cgtcatgttc ggttcgccgg aaacgacgac gggcggtaat     1980
gcgcttaaat tctacgcctc ggtgcgtctc gacattcgcc gtatcggcgc cgtcaaggag     2040
cgtgaagagg ttgtcggcaa ccagacccgc gtcaaggtcg tcaagaacaa gatggcaccg     2100
cctttcaagc aggtggaatt cgacatcatg tatggtgaag gcgtttccaa gaccggcgag     2160
cttgtcgatc tcggcgtgaa agccggtatc gtcgagaaat ccggtgcatg gttctcctat     2220
aacagccagc gtttggggca ggggcgtgaa aatgccaaga cttttcctgcg cgacaatccg     2280
gaaatggcaa gcgagatcga actggcgctg cgccagaacg ccggtctgat cgccgatcgg     2340
ttcctgcaga atggcggccc ggaagctggc gaaagcgacg acggtcccga cgagggctga     2400
tgcattcgaa ggtccgggcg ttcgcgtccg gtggctttgc cggcatgagc cggtatggat     2460
caaaagggtc gtgcgatttt cctcgcgtgg cccttttct ttgcctagac gccttggtgc       2520
gcctccatgg ctggacaggg caggatgcgg acgataaaag cctttgattt tgcaagatag     2580
ccatcattcg ggatggcggt gatggactcc agctgtgagc ggtgtgtggg catgagcggt     2640
gtgaatgaaa ttcggtcgac cttctcgac tacttcaaga agaacggaca cgagattgtg      2700
ccctccagcc cgctggtgcc gcgcaacgat ccgacgctga tgttcaccaa tgccggcatg     2760
gtgcagttca agaacgtctt caccggtctc gaaagccgtc cttattccac cgccgcctcg     2820
gcgcagaaat gcgtgcgcgc cggtggcaag cataacgacc tggacaatgt cggttatacg     2880
gcccgtcacc atacgttctt cgaaatgctc ggcaatttct cctttggcga ctatttcaag     2940
gaagaggcga ttacccatgc ctggaacctg atcaccaagg aattcggcat cgaccgcaac     3000
cgtctgctgg tcacggtcta tcacaccgac gacgaggctt ttaatctctg gaagaagatc     3060
gccggtttct ccgacgatcg catcatccgt attccgacca gcgataattt ctgggccatg     3120
ggcgataccg gtccgtgcgg tccctgctcg gaaatcttct atgaccacgg cgatcatatc     3180
tggggcggac cgcccggttc gccggaagag gatggcgacc gtttcatcga aatctggaac     3240
```

-continued

```
ctcgtcttca tgcaatatga gcagctgacg aaggaagagc gcatcgatct gccgcgcccg    3300
tctatcgaca ccggcatctc gagcgcattt cggcgttgtt gcagggcaaa cacgacaatt    3360
acgacaccga tctgttccgg gcgctgattt cggcctccgt cgaagcgacc ggcgttccgg    3420
cagagggcga gaagcgcgcc agccatcgcg tcattgccga tcatctgcgc tcctccgctt    3480
tcctgatcgc cgatggcgtc ctgccgtcaa atgagggccg tggttacgtt ctgcgccgca    3540
tcatgcgccg cgccatgcgc catgccgagc ttctcggttc gcgcgagccg ctgatctaca    3600
agctgctgcc ggcgctgata cagcagatgg gccgcgccta tccggaactg gttcgcgccg    3660
aggcgctgat ctccgagacg                                                3680
```

<210> SEQ ID NO 12
<211> LENGTH: 363
<212> TYPE: PRT
<213> ORGANISM: Agrobacterium tumefaciens

<400> SEQUENCE: 12

```
Met Ala Gln Asn Ser Leu Arg Leu Val Glu Asp Lys Ser Val Asp Lys
 1               5                  10                  15

Ser Lys Ala Leu Glu Ala Ala Leu Ser Gln Ile Glu Arg Ser Phe Gly
            20                  25                  30

Lys Gly Ser Ile Met Lys Leu Gly Ser Asn Glu Asn Val Val Glu Val
        35                  40                  45

Glu Thr Ile Ser Thr Gly Ser Leu Ser Leu Asp Ile Ala Leu Gly Ile
    50                  55                  60

Gly Gly Leu Pro Lys Gly Arg Ile Val Glu Ile Tyr Gly Pro Glu Ser
65                  70                  75                  80

Ser Gly Lys Thr Thr Leu Ala Leu Gln Thr Ile Ala Glu Ala Gln Lys
                85                  90                  95

Lys Gly Gly Ile Cys Ala Phe Val Asp Ala Glu His Ala Leu Asp Pro
            100                 105                 110

Val Tyr Ala Arg Lys Leu Gly Val Asp Leu Gln Asn Leu Leu Ile Ser
        115                 120                 125

Gln Pro Asp Thr Gly Glu Gln Ala Leu Glu Ile Thr Asp Thr Leu Val
    130                 135                 140

Arg Ser Gly Ala Val Asp Ile Leu Val Val Asp Ser Val Ala Ala Leu
145                 150                 155                 160

Thr Pro Arg Ala Glu Ile Glu Gly Glu Met Gly Asp Ser Leu Pro Gly
                165                 170                 175

Leu Gln Ala Arg Leu Met Ser Gln Ala Leu Arg Lys Leu Thr Ala Ser
            180                 185                 190

Ile Ser Lys Ser Lys Cys Met Val Ile Phe Ile Asn Gln Ile Arg Met
        195                 200                 205

Lys Ile Gly Val Met Phe Gly Ser Pro Glu Thr Thr Thr Gly Gly Asn
    210                 215                 220

Ala Leu Lys Phe Tyr Ala Ser Val Arg Leu Asp Ile Arg Arg Ile Gly
225                 230                 235                 240

Ala Val Lys Glu Arg Glu Glu Val Val Gly Asn Gln Thr Arg Val Lys
                245                 250                 255

Val Val Lys Asn Lys Met Ala Pro Pro Phe Lys Gln Val Glu Phe Asp
            260                 265                 270

Ile Met Tyr Gly Glu Gly Val Ser Lys Thr Gly Glu Leu Val Asp Leu
        275                 280                 285
```

```
Gly Val Lys Ala Gly Ile Val Glu Lys Ser Gly Ala Trp Phe Ser Tyr
    290                 295                 300

Asn Ser Gln Arg Leu Gly Gln Gly Arg Glu Asn Ala Lys Thr Phe Leu
305                 310                 315                 320

Arg Asp Asn Pro Glu Met Ala Ser Glu Ile Glu Leu Ala Leu Arg Gln
                325                 330                 335

Asn Ala Gly Leu Ile Ala Asp Arg Phe Leu Gln Asn Gly Gly Pro Glu
            340                 345                 350

Ala Gly Glu Ser Asp Asp Gly Pro Asp Glu Gly
            355                 360

<210> SEQ ID NO 13
<211> LENGTH: 3186
<212> TYPE: DNA
<213> ORGANISM: Agrobacterium tumefaciens

<400> SEQUENCE: 13
```

| | | | | | |
|---|---|---|---|---|---|
| atgactttca | cccatcacgc | aaagcgcgtc | ctgacgatcg | ctgcgggaac | accgttcctc | 60 |
| aaaacgctcg | cggaaacgct | gtgtgacggg | acactgacag | ccggctataa | atacgaccct | 120 |
| gcggatccgc | tttcgcttgc | caaggtgacg | atctatgttc | cgacccggcg | ctccgcccgc | 180 |
| gtgctgcgct | cagagtttgt | cgatcttctg | ggcggccgtt | ccgccatttt | gccactgatc | 240 |
| cggccgctcg | gcgaaaccga | tgacgacagc | ggcttcttcg | agatcgaaaa | tcctgagatc | 300 |
| atggatctgg | cgccgccgat | ttccggcacc | ggccggcaaa | tcgagctggc | gcgcctcatt | 360 |
| ctggcatggc | gcaacagcct | gcccgacgcc | atcagggcca | tccattcgga | ctcaccactt | 420 |
| gtcgccccg | ccagccctgc | cgacgccata | tggctggcgc | gcgcgcttgg | cgaagtgatc | 480 |
| gatgcgatgg | atacggaaga | aaaagaatgg | gaggcgctcg | cgcatctcga | taccggcgat | 540 |
| cacgcccaat | ggtggcagct | gacggcggat | ttcctgaaaa | tcgccagcgt | gttctggccc | 600 |
| gcccgtcttg | ccgaactcaa | tcgaacttcc | gcaggccgac | atcgcaacgg | catcctgagg | 660 |
| gcagaggcga | accggcttgc | caacctgccg | gacaccggac | caatcatcgt | tgcgggctcc | 720 |
| acgggctcaa | ttccggcagc | agcagaccdtt | atcgcctctg | tcgcctccct | gcccagggc | 780 |
| gtcgtcgtgc | ttccgggcct | cgatcttacg | atgccggagg | aacaatggga | ggctattgcc | 840 |
| gaggacccta | ccgatccttc | aagccgcacc | cattcgcaat | acggactcta | catgctgttg | 900 |
| cagaagctcg | atatcatgcg | agacgatgtc | gttcagattg | gcgctatcga | tagcgatctt | 960 |
| gaaaaacgcg | cggcggtttt | tcggcagca | cttgctcctg | ccaaatccac | cagcgactgg | 1020 |
| aaccgctggc | gtgaggacaa | gcaacccgga | ttttttcgacg | atgctttttgc | ggcagcgacc | 1080 |
| ctgatagaag | ctgcaaacga | gcgcgaagag | gcaaccgcaa | ttgcggtggc | gctgcggctg | 1140 |
| gcgcttgaag | cgccgggcgc | tggccgcccg | tctcaggccg | cgctgatcac | gcccgatcgc | 1200 |
| ggactggcca | ggcgcgtggc | gacggaattg | caacgcttcg | gtatcgaagc | cgacgattcc | 1260 |
| gccggtacgc | cgctttccgc | cacgccgcag | gccggactga | cgcaactcgc | actgaaagct | 1320 |
| atcctcaggc | ccggagatcc | ggtgccggtc | atttcccttc | tgaaacatcc | gctcagccgt | 1380 |
| ttcgggcttt | cgctggaggc | ttttacaaaa | gcatcaaagg | cgctggaatt | gatcgcactt | 1440 |
| agaggcggcc | gcgtcgaaac | ggaaatcggc | aatctggagg | cggttctcga | tgcgcaactg | 1500 |
| gcggcgcagc | gtgatgaccg | gcatccgcct | gcctggaggc | tggcactgcc | cgagggaagc | 1560 |
| gtagacgccg | cgcgcgatct | ggcacgccgg | atcgccgttt | cgacagagcc | gcttggcagc | 1620 |
| gcattcgttc | gtagcgaccg | ctcaggccgg | tctttcacgg | acaaattgcc | gctttccgat | 1680 |

```
tgggccgagc ggacgggccg ggtgatcgaa gccatctgcg cggatgacaa caacgatctt    1740
gccactctct ggtccggcga ggcaggcgac aagctttccg gcctgtttgg cgaattgatg    1800
gaaagcggcg aaatcctgga tgcggatggt ccgcaatggg ctgatatctt cgcggcactg    1860
gtggctggcg aatcgatcaa gccgcgatcc atgcgccatc cgcgcatttt cattttcggt    1920
gcccttgagg cacgactgca aagcgtcgac actgtcgtga tcggcggtct caatgaaggg    1980
ctttggccgg ccagacggc aaacaacccg tttctgtccc gcaacatgaa gacagccatc    2040
ggtctggaac cgccggagcg cgcatcggc cagctggcgc acgatttcga gatggcgaac    2100
gggacacggc agattttcta cagccgcgcg ctcagacagg gctcgacacc cgcagtcgca    2160
tcgcgctggc tgcagcgatt gctggcactc ggcggcgagg attttgccga acagctgaag    2220
aagcgcggcg agacctatcg ccactgggca gccctgatgg atgcgaccat cgaccaggaa    2280
gcagcaaagc gccctgcccc caaaccgccg gccgacttgc agccgaagag ctattccttc    2340
agcgaagtgg gcaggctgcg ccgtgacccc tattcgatct acgcgcggcg tatcctgaag    2400
ctcaacccgc ttgatggctt caaccgcgat cccaatgccg ccgaccgtgg cacgctctat    2460
catgcaatca ttgagcgcta ttcccgcgag gggcatattc ccggcacacc ggcatcgctc    2520
gaggccatgc agcgtattct ggatgagagt ttcgacgcgg aagatcttcc tgcacatgtc    2580
gatgtcatct ggcgcccgcg attcgaggcg gtggcacgcg cctttatcga ctgggagaaa    2640
gaacgacatc catccatccg ccgcagcttt ttcgaggcgc gtgccggaca ggaaatcccc    2700
gaggcaggca taaggctgac cggcatcgcc gaccgcatag atatcaagac cggcggtcag    2760
gcggatatta tcgactacaa aacggggctt gcgccttcag tcaatcaggc gcgcgcgctg    2820
ctcgacccgc agctcgcgct ggaagcggca gcactgatgc ggggcgcctt ccgcgaggcg    2880
ggttcgcaga caccggaaaa ccttatctat gtgcgcctgc ggccgggtac ccgtttttt     2940 gccgaccagg tgaataacga acactccaac cggggtggca aaaagcacc gaaatcggca     3000 attgagctgg caaccgaatc aatcgatcag ctggccaagt tcgtgcgttc gctgcgtgat    3060
ggcgagaacg gttttgcctc gcggctggtg ccggaggagc agcagtccta tgggggggaa    3120
tatgaccacc tcgcccgcgt ttcggaatgg tcgacggcag aaccgggaga cggcgatgat    3180
gattga                                                              3186
```

<210> SEQ ID NO 14
<211> LENGTH: 1061
<212> TYPE: PRT
<213> ORGANISM: Agrobacterium tumefaciens

<400> SEQUENCE: 14

```
Met Thr Phe Thr His His Ala Lys Arg Val Leu Thr Ile Ala Ala Gly
1               5                   10                  15

Thr Pro Phe Leu Lys Thr Leu Ala Glu Thr Leu Cys Asp Gly Thr Leu
            20                  25                  30

Thr Ala Gly Tyr Lys Tyr Asp Pro Ala Asp Pro Leu Ser Leu Ala Lys
        35                  40                  45

Val Thr Ile Tyr Val Pro Thr Arg Arg Ser Ala Arg Val Leu Arg Ser
    50                  55                  60

Glu Phe Val Asp Leu Leu Gly Gly Arg Ser Ala Ile Leu Pro Leu Ile
65                  70                  75                  80

Arg Pro Leu Gly Glu Thr Asp Asp Asp Ser Gly Phe Phe Glu Ile Glu
                85                  90                  95

Asn Pro Glu Ile Met Asp Leu Ala Pro Pro Ile Ser Gly Thr Gly Arg
```

```
                100             105                110
Gln Ile Glu Leu Ala Arg Leu Ile Leu Ala Trp Arg Asn Ser Leu Pro
            115                 120                 125
Asp Ala Ile Arg Ala Ile His Ser Asp Ser Pro Leu Val Ala Pro Ala
        130                 135                 140
Ser Pro Ala Asp Ala Ile Trp Leu Ala Arg Ala Leu Gly Glu Val Ile
145                 150                 155                 160
Asp Ala Met Asp Thr Glu Glu Lys Glu Trp Glu Ala Leu Ala His Leu
                165                 170                 175
Asp Thr Gly Asp His Ala Gln Trp Trp Gln Leu Thr Ala Asp Phe Leu
            180                 185                 190
Lys Ile Ala Ser Val Phe Trp Pro Ala Arg Leu Ala Glu Leu Asn Arg
        195                 200                 205
Thr Ser Ala Gly Arg His Arg Asn Gly Ile Leu Arg Ala Glu Ala Asn
    210                 215                 220
Arg Leu Ala Asn Leu Pro Asp Thr Gly Pro Ile Ile Val Ala Gly Ser
225                 230                 235                 240
Thr Gly Ser Ile Pro Ala Ala Asp Leu Ile Ala Ser Val Ala Ser
                245                 250                 255
Leu Pro Gln Gly Val Val Leu Pro Gly Leu Asp Leu Thr Met Pro
            260                 265                 270
Glu Glu Gln Trp Glu Ala Ile Ala Glu Asp Pro Thr Asp Pro Ser Ser
        275                 280                 285
Arg Thr His Ser Gln Tyr Gly Leu Tyr Met Leu Leu Gln Lys Leu Asp
    290                 295                 300
Ile Met Arg Asp Asp Val Val Gln Ile Gly Ala Ile Asp Ser Asp Leu
305                 310                 315                 320
Glu Lys Arg Ala Ala Val Phe Ser Ala Ala Leu Ala Pro Ala Lys Ser
                325                 330                 335
Thr Ser Asp Trp Asn Arg Trp Arg Glu Asp Lys Gln Pro Gly Phe Phe
            340                 345                 350
Asp Asp Ala Phe Ala Ala Thr Leu Ile Glu Ala Ala Asn Glu Arg
        355                 360                 365
Glu Glu Ala Thr Ala Ile Ala Val Ala Leu Arg Leu Ala Leu Glu Ala
    370                 375                 380
Pro Gly Ala Gly Arg Pro Ser Gln Ala Ala Leu Ile Thr Pro Asp Arg
385                 390                 395                 400
Gly Leu Ala Arg Arg Val Ala Thr Glu Leu Gln Arg Phe Gly Ile Glu
                405                 410                 415
Ala Asp Asp Ser Ala Gly Thr Pro Leu Ser Ala Thr Pro Gln Ala Gly
            420                 425                 430
Leu Thr Gln Leu Ala Leu Glu Ala Ile Leu Arg Pro Gly Asp Pro Val
        435                 440                 445
Pro Val Ile Ser Leu Leu Lys His Pro Leu Ser Arg Phe Gly Leu Ser
    450                 455                 460
Leu Glu Ala Phe Thr Lys Ala Ser Lys Ala Leu Glu Leu Ile Ala Leu
465                 470                 475                 480
Arg Gly Gly Arg Val Glu Thr Glu Ile Gly Asn Leu Glu Ala Val Leu
                485                 490                 495
Asp Ala Gln Leu Ala Ala Gln Arg Asp Asp Arg His Pro Pro Ala Trp
            500                 505                 510
Arg Leu Ala Leu Pro Glu Gly Ser Val Asp Ala Ala Arg Asp Leu Ala
        515                 520                 525
```

```
Arg Arg Ile Ala Val Ser Thr Glu Pro Leu Gly Ser Ala Phe Val Arg
        530                 535                 540

Ser Asp Arg Ser Gly Arg Ser Phe Thr Asp Lys Leu Pro Leu Ser Asp
545                 550                 555                 560

Trp Ala Glu Arg Thr Gly Arg Val Ile Glu Ala Ile Cys Ala Asp Asp
                565                 570                 575

Asn Asn Asp Leu Ala Thr Leu Trp Ser Gly Glu Ala Gly Asp Lys Leu
            580                 585                 590

Ser Gly Leu Phe Gly Glu Leu Met Glu Ser Gly Glu Ile Leu Asp Ala
        595                 600                 605

Asp Gly Pro Gln Trp Ala Asp Ile Phe Ala Ala Leu Val Ala Gly Glu
    610                 615                 620

Ser Ile Lys Pro Arg Ser Met Arg His Pro Arg Ile Phe Ile Phe Gly
625                 630                 635                 640

Ala Leu Glu Ala Arg Leu Gln Ser Val Asp Thr Val Ile Gly Gly
                645                 650                 655

Leu Asn Glu Gly Leu Trp Pro Gly Gln Thr Ala Asn Asn Pro Phe Leu
            660                 665                 670

Ser Arg Asn Met Lys Thr Ala Ile Gly Leu Glu Pro Pro Glu Arg Arg
        675                 680                 685

Ile Gly Gln Leu Ala His Asp Phe Glu Met Ala Asn Gly Thr Arg Gln
    690                 695                 700

Ile Phe Tyr Ser Arg Ala Leu Arg Gln Gly Ser Thr Pro Ala Val Ala
705                 710                 715                 720

Ser Arg Trp Leu Gln Arg Leu Leu Ala Leu Gly Gly Glu Asp Phe Ala
                725                 730                 735

Glu Gln Leu Lys Lys Arg Gly Glu Thr Tyr Arg His Trp Ala Ala Leu
            740                 745                 750

Met Asp Ala Thr Ile Asp Gln Glu Ala Ala Lys Arg Pro Ala Pro Lys
        755                 760                 765

Pro Pro Ala Asp Leu Gln Pro Lys Ser Tyr Ser Phe Ser Glu Val Gly
    770                 775                 780

Arg Leu Arg Arg Asp Pro Tyr Ser Ile Tyr Ala Arg Arg Ile Leu Lys
785                 790                 795                 800

Leu Asn Pro Leu Asp Gly Phe Asn Arg Asp Pro Asn Ala Ala Asp Arg
                805                 810                 815

Gly Thr Leu Tyr His Ala Ile Ile Glu Arg Tyr Ser Arg Glu Gly His
            820                 825                 830

Ile Pro Gly Thr Pro Ala Ser Leu Glu Ala Met Gln Arg Ile Leu Asp
        835                 840                 845

Glu Ser Phe Asp Ala Glu Asp Leu Pro Ala His Val Asp Val Ile Trp
    850                 855                 860

Arg Pro Arg Phe Glu Ala Val Ala Arg Ala Phe Ile Asp Trp Glu Lys
865                 870                 875                 880

Glu Arg His Pro Ser Ile Arg Arg Ser Phe Phe Glu Ala Arg Ala Gly
                885                 890                 895

Gln Glu Ile Pro Glu Ala Gly Ile Arg Leu Thr Gly Ile Ala Asp Arg
            900                 905                 910

Ile Asp Ile Lys Thr Gly Gly Gln Ala Asp Ile Ile Asp Tyr Lys Thr
        915                 920                 925

Gly Leu Ala Pro Ser Val Asn Gln Ala Arg Ala Leu Leu Asp Pro Gln
    930                 935                 940
```

```
Leu Ala Leu Glu Ala Ala Leu Met Arg Gly Ala Phe Arg Glu Ala
945                 950                 955                 960

Gly Ser Gln Thr Pro Glu Asn Leu Ile Tyr Val Arg Leu Arg Pro Gly
            965                 970                 975

Thr Arg Phe Phe Ala Asp Gln Val Asn Asn Glu His Ser Asn Arg Gly
                980                 985                 990

Gly Lys Lys Ala Pro Lys Ser Ala Ile Glu Leu Ala Thr Glu Ser Ile
        995                 1000                1005

Asp Gln Leu Ala Lys Phe Val Arg Ser Leu Arg Asp Gly Glu Asn
    1010                1015                1020

Gly Phe Ala Ser Arg Leu Val Pro Glu Glu Gln Gln Ser Tyr Gly
    1025                1030                1035

Gly Glu Tyr Asp His Leu Ala Arg Val Ser Glu Trp Ser Thr Ala
    1040                1045                1050

Glu Pro Gly Asp Gly Asp Asp Asp
    1055                1060
```

<210> SEQ ID NO 15
<211> LENGTH: 1128
<212> TYPE: DNA
<213> ORGANISM: Agrobacterium tumefaciens

<400> SEQUENCE: 15

```
atgttatttt caccgcaaca ggacgaagcg ctcaaggctg tttcccgctg gctgaaggaa      60
ggccggacgc cggttttttcg gttgttcggt tatgccggaa ccggcaagac gacgcttgcc    120
aaacatttcg cggaaaatgt cgatggcgaa gtgctgtttg cggccttcac cggcaaggcg    180
gcgcaggtgc tgcgctcgcg cggggcgacc aatgcccgca ccatccattc gctgatctac    240
cgcccgcgcg cgaagagac cgtggaagac gaggagaccg gcaagacctc ggtcgcgcca    300
atgttttcca tcaaccgcca gagcccgctc gccaaggcgg cactcatcat catcgatgaa    360
tgttcgatgg tggatgagca gctcggcaag gatctgatga gcttcggcac gcctatcctg    420
gtgctcggcg atcccgggca gttgccgcca gtttcaggcg gtggcttctt cacggagcag    480
gagcctgatt acctgctctc gaaattcat cggcaggcca aggacaatcc catcatccac    540
cttgccatgg atgtgcggga aggccgcgag atcatgcgtg gcgattacgg tgccgcgcag    600
gtgatttcca gtccgaggt gacacagtcg ctcgtgctcg atgccgatca ggtgctcgtc    660
ggcacaaatc gcacgcgacg ccgttataac cagcggcttc gcgagctgaa gggatttacg    720
gccgattatc cgcaatccgg cgacaagctg gtttgcttga ggaacgatcc ggccaagggc    780
ctgctgaacg gctctctctg gcaggtcatg agttcgtcgc gcgagacggt gaaacccggc    840
atcaacctga tgatccggcc tgaagacgac gatatggatc ggggcgcggc caagatcaaa    900
ttgctgaagg cggctttcga ggatgtggaa acggaaattc cgtggaccac ccgcaagcgt    960
tatgacgagt cgatttcgg ctatgcgctg accgtgcaca aggcgcaggg ttcgcagtgg   1020
aacaatgtgg ttctctttga cgagagctat gccttccgcg attcgcgcga gcggtggctt   1080
tacaccgcca tcacccgcgc cgcagaaaca ctcacaatcg ttcgctga                1128
```

<210> SEQ ID NO 16
<211> LENGTH: 375
<212> TYPE: PRT
<213> ORGANISM: Agrobacterium tumefaciens

<400> SEQUENCE: 16

Met Leu Phe Ser Pro Gln Gln Asp Glu Ala Leu Lys Ala Val Ser Arg

```
  1               5                  10                 15
Trp Leu Lys Glu Gly Arg Thr Pro Val Phe Arg Leu Phe Gly Tyr Ala
             20                 25                 30
Gly Thr Gly Lys Thr Thr Leu Ala Lys His Phe Ala Glu Asn Val Asp
             35                 40                 45
Gly Glu Val Leu Phe Ala Ala Phe Thr Gly Lys Ala Ala Gln Val Leu
 50                 55                 60
Arg Ser Arg Gly Ala Thr Asn Ala Arg Thr Ile His Ser Leu Ile Tyr
 65                 70                 75                 80
Arg Pro Arg Gly Glu Glu Thr Val Glu Asp Glu Thr Gly Lys Thr
                 85                 90                 95
Ser Val Ala Pro Met Phe Ser Ile Asn Arg Gln Ser Pro Leu Ala Lys
                100                105                110
Ala Ala Leu Ile Ile Ile Asp Glu Cys Ser Met Val Asp Glu Gln Leu
            115                120                125
Gly Lys Asp Leu Met Ser Phe Gly Thr Pro Ile Leu Val Leu Gly Asp
            130                135                140
Pro Gly Gln Leu Pro Pro Val Ser Gly Gly Gly Phe Phe Thr Glu Gln
145                150                155                160
Glu Pro Asp Tyr Leu Leu Ser Glu Ile His Arg Gln Ala Lys Asp Asn
                165                170                175
Pro Ile Ile His Leu Ala Met Asp Val Arg Glu Gly Arg Glu Ile Met
            180                185                190
Arg Gly Asp Tyr Gly Ala Ala Gln Val Ile Ser Lys Ser Glu Val Thr
            195                200                205
Gln Ser Leu Val Leu Asp Ala Asp Gln Val Leu Val Gly Thr Asn Arg
210                215                220
Thr Arg Arg Arg Tyr Asn Gln Arg Leu Arg Glu Leu Lys Gly Phe Thr
225                230                235                240
Ala Asp Tyr Pro Gln Ser Gly Asp Lys Leu Val Cys Leu Arg Asn Asp
                245                250                255
Pro Ala Lys Gly Leu Leu Asn Gly Ser Leu Trp Gln Val Met Ser Ser
            260                265                270
Ser Arg Glu Thr Val Lys Pro Gly Ile Asn Leu Met Ile Arg Pro Glu
            275                280                285
Asp Asp Asp Met Asp Arg Gly Ala Ala Lys Ile Lys Leu Leu Lys Ala
            290                295                300
Ala Phe Glu Asp Val Glu Thr Glu Ile Pro Trp Thr Thr Arg Lys Arg
305                310                315                320
Tyr Asp Glu Phe Asp Phe Gly Tyr Ala Leu Thr Val His Lys Ala Gln
                325                330                335
Gly Ser Gln Trp Asn Asn Val Val Leu Phe Asp Glu Ser Tyr Ala Phe
            340                345                350
Arg Asp Ser Arg Glu Arg Trp Leu Tyr Thr Ala Ile Thr Arg Ala Ala
            355                360                365
Glu Thr Leu Thr Ile Val Arg
370                375
```

<210> SEQ ID NO 17
<211> LENGTH: 1128
<212> TYPE: DNA
<213> ORGANISM: Agrobacterium tumefaciens

<400> SEQUENCE: 17

```
atgacgaata aggtgtcgct tttacggctg aaactcacgg acttccgcaa ctatgcggcg      60
gcgtcgcttg cgctggatga ccgccacgtg gtgctgacgg gtgacaacgg ttccggcaag     120
accaatctcc tggaggctgt ttcgtttctg tcgcccggaa ggggcctgcg ccgcgccacc     180
ctgtccgatg tgacgcgagt gggggcggag gccgccggtt tttcgatttt tgcggatgtc     240
gacggcatgg acggcgaggt cgccatcgga accgggatcg agggtgacgg cgaggtagtg     300
tcgcgccgcc tgaggctgaa cgggacatcg gtgaagtcgg tcgatgaatt gacggatcat     360
ctgcgggtgc tgtggctgac gcctgccatg gatgggcttt ttaccggttc atcctcggat     420
cgccggcgtt ttctcgatcg gttggtgctc tcgctcgatc ccgcgcatgg gcggcgggca     480
agcgacttcg aaaaggccat gcgcggccgc aaccgtctgc tttcggaagg ccgtttcgat     540
ccggtctggc tggacggtat cgagaagcag atggcggaac tcggcatttc catggcgctc     600
gcgcgctatg aaatgttggg tcttttgaaa agcctcatcg aaggccgttc cggcaatgct     660
gccttcccct ctgcagcgct ggcgctctcg gtttcatgg acgacacgct caaccggccg      720
gctgtcgatc tggaagacga gtataggctt atgctgcgcg aaggccggta tcgagacgcg     780
gcggcgggcc gcacgcttga tggaccgcac cgtgtcgatc tgttcgtgcg ccatgcggaa     840
aagaacatgg aggcagagcg ttgctcgacc ggagaacaga aggcgctgct ggtgggattg     900
gtgcttgcgc atgcccagct caccgccaac atgaccggcc atgcgccggt tctgctgctc     960
gacgaaattg ccgcgcatct ggatgagggc aggcgggcgg ctctgttcga tctcattcac    1020
gcgctcggtg gtcagagttt catgaccgga acggatgcgg caatgttctc cgcccttggc    1080
gacagggcgc aattcttcaa tgtctcccac gggggcatca cggcatga                 1128
```

<210> SEQ ID NO 18
<211> LENGTH: 375
<212> TYPE: PRT
<213> ORGANISM: Agrobacterium tumefaciens

<400> SEQUENCE: 18

```
Met Thr Asn Lys Val Ser Leu Leu Arg Leu Lys Leu Thr Asp Phe Arg
1               5                   10                  15

Asn Tyr Ala Ala Ala Ser Leu Ala Leu Asp Asp Arg His Val Val Leu
            20                  25                  30

Thr Gly Asp Asn Gly Ser Gly Lys Thr Asn Leu Leu Glu Ala Val Ser
        35                  40                  45

Phe Leu Ser Pro Gly Arg Gly Leu Arg Arg Ala Thr Leu Ser Asp Val
    50                  55                  60

Thr Arg Val Gly Ala Glu Ala Ala Gly Phe Ser Ile Phe Ala Asp Val
65                  70                  75                  80

Asp Gly Met Asp Gly Glu Val Ala Ile Gly Thr Gly Ile Glu Gly Asp
                85                  90                  95

Gly Glu Val Val Ser Arg Arg Leu Arg Leu Asn Gly Thr Ser Val Lys
            100                 105                 110

Ser Val Asp Glu Leu Thr Asp His Leu Arg Val Leu Trp Leu Thr Pro
        115                 120                 125

Ala Met Asp Gly Leu Phe Thr Gly Ser Ser Ser Asp Arg Arg Arg Phe
    130                 135                 140

Leu Asp Arg Leu Val Leu Ser Leu Asp Pro Ala His Gly Arg Arg Ala
145                 150                 155                 160

Ser Asp Phe Glu Lys Ala Met Arg Gly Arg Asn Arg Leu Leu Ser Glu
                165                 170                 175
```

```
Gly Arg Phe Asp Pro Val Trp Leu Asp Gly Ile Glu Lys Gln Met Ala
            180                 185                 190

Glu Leu Gly Ile Ser Met Ala Leu Ala Arg Tyr Glu Met Leu Gly Leu
        195                 200                 205

Leu Lys Ser Leu Ile Glu Gly Arg Ser Gly Asn Ala Ala Phe Pro Ser
    210                 215                 220

Ala Ala Leu Ala Leu Ser Gly Phe Met Asp Asp Thr Leu Asn Arg Pro
225                 230                 235                 240

Ala Val Asp Leu Glu Asp Glu Tyr Arg Leu Met Leu Arg Glu Gly Arg
                245                 250                 255

Tyr Arg Asp Ala Ala Ala Gly Arg Thr Leu Asp Gly Pro His Arg Val
            260                 265                 270

Asp Leu Phe Val Arg His Ala Glu Lys Asn Met Glu Ala Glu Arg Cys
        275                 280                 285

Ser Thr Gly Glu Gln Lys Ala Leu Leu Val Gly Leu Val Leu Ala His
    290                 295                 300

Ala Gln Leu Thr Ala Asn Met Thr Gly His Ala Pro Val Leu Leu Leu
305                 310                 315                 320

Asp Glu Ile Ala Ala His Leu Asp Glu Gly Arg Arg Ala Ala Leu Phe
                325                 330                 335

Asp Leu Ile His Ala Leu Gly Gly Gln Ser Phe Met Thr Gly Thr Asp
            340                 345                 350

Ala Ala Met Phe Ser Ala Leu Gly Asp Arg Ala Gln Phe Phe Asn Val
        355                 360                 365

Ser His Gly Gly Ile Thr Ala
    370                 375

<210> SEQ ID NO 19
<211> LENGTH: 2106
<212> TYPE: DNA
<213> ORGANISM: Agrobacterium tumefaciens

<400> SEQUENCE: 19
atgcgtcccg ccattctcga tccgctattt gcttccgtct ccacccttgc cggtgtgggg      60
ccgaagcttg ccgaccttct ggccaaactg ctgagccggg aaaatgccga cgacacccgc     120
gtgatcgatc ttctgttcca cgcgccatca acgtcatcg accggcgcaa ccgcccgggc     180
atcgcgcttg ccgctcccgg cgccattgtc accatccagg acgtgtcga ccggcatcag     240 ccagctccac caggcaatcg ttccgcgccc taccgtgttt tcctgcatga cgagaccggg     300
gaactggcgc tgaccttctt ccgcgccaag ggagactggc tttccaaggc cttacccgtc     360
gatgaagagg ttctcgtcag cggcaaggtg gactggttca acggccgcgc tccatggtg     420 catccggatt tcatggtgaa gctctccgag gccgagaacc tgccgctggt cgaagccgtt     480
tatccgatga cagccgggct gtctccgaag gtgctgcggc gggcaattga aggcgggctt     540
tcgaaactgc cggtctttcc cgaatggatc gacgaaacgc tcaagacccg tcagggtttc     600
ggcgacgtgg catcgagctt ccgtgagttg cacgatccgc gcgacagcgc cgatatcgat     660
cctcaggccc cggcacgcag acggctcgcc tacgacgaat tcctggccgg gcagctgtca     720
ctggcgctgg tgcggcaaag actgcgcaag gtcgcgggcc agccgatccg cgccaagggg     780
gacattgctg caaaaatcct gtcgcaactg cccttctccc tgacgccgag ccagaatgcc     840
tcggtgaaag atatcctgac cgatatggcc agcgaggacc gtatgttgcg gctgttgcaa     900
ggcgatgtcg gcgcgggcaa gacgctggtg gcgctgatgg ctatgcaac cgccgtcgag     960
```

```
gccggagggc aggcggtgtt gatggccccg accgaaattc ttgcccggca gcatttcgcc    1020
accatctcca aactcgccaa tgccgtgggc attacggttg aggtgctgac cggccgcacc    1080
aagggcaagg agcgtcgcga gatcgaagaa cgcgtggcct ccggtgaggc acagatcgtc    1140
atcggcaccc acgcgctgtt ccaggacagc gtgagttaca agaacctcgt gctggccgtg    1200
gtggatgagc agcaccgttt cggcgtacac cagcgcctgc gtctcaccgc caagggcatc    1260
acgccgcata tgcttgttat gaccgccacg cccattccgc gcacgctggt gctggccgcc    1320
ttcggcgaca tggatgtgtc gaaactcacc gaaaaaccgg ccggccgaaa accgatccag    1380
accgtgacaa tccccacaga gcgcatcggc gacatcgtcg agcggctgcg cgccgcgctg    1440
aaggagggca agaaggccta ctggatctgc ccgctggtgg aggagacgga agagtccgac    1500
ctgatgtcgg cggaagaacg acatgcggtt ctctcgcaga tgctcggtgc caatatcggt    1560
ctcatccatg ggcgcatgag cggccctgag aaggacgccg ccatgctggc tttcaagaac    1620
ggcgaaaccc ggctgctggt tgcaacgaca gtggtggaag tgggtgtcga cgttccggac    1680
gccacgatca tggtcatcga acatgccgaa cgtttcggcc tggcccagct tcaccagctg    1740
cgtggccggg ttggacgcgg tgacgaggcc tccacctgca tcctgctcta aggggccg    1800 ctcagcgaaa acgccgcgc ccgactttcc atcctgcgcg acagcgagga cggcttcctg    1860
attgccgaag aggatttgaa gctgcgcggc gaaggcgaac tcctcggcac cgccagtcc    1920 ggaaccccgg gcttccgcat cgccagcctc gaagcccatg ccgatctcct ggaaatcgcc    1980
cgcaaggacg ccgcctatgt catcgagcgc gaccccgaac tgaccggccc gcgcggcgaa    2040
agcctgcgca ccctgctcta tctgcaccgc cgcgacgaag ctatccgctt cctgcacgcc    2100
ggctga                                                              2106
```

<210> SEQ ID NO 20
<211> LENGTH: 701
<212> TYPE: PRT
<213> ORGANISM: Agrobacterium tumefaciens

<400> SEQUENCE: 20

Met Arg Pro Ala Ile Leu Asp Pro Leu Phe Ala Ser Val Ser Thr Leu
1               5                   10                  15

Ala Gly Val Gly Pro Lys Leu Ala Asp Leu Leu Ala Lys Leu Leu Ser
            20                  25                  30

Arg Glu Asn Ala Asp Asp Thr Arg Val Ile Asp Leu Leu Phe His Ala
        35                  40                  45

Pro Ser Asn Val Ile Asp Arg Arg Asn Arg Pro Gly Ile Ala Leu Ala
    50                  55                  60

Ala Pro Gly Ala Ile Val Thr Ile Gln Gly Arg Val Asp Arg His Gln
65                  70                  75                  80

Pro Ala Pro Pro Gly Asn Arg Ser Ala Pro Tyr Arg Val Phe Leu His
                85                  90                  95

Asp Glu Thr Gly Glu Leu Ala Leu Thr Phe Phe Arg Ala Lys Gly Asp
            100                 105                 110

Trp Leu Ser Lys Ala Leu Pro Val Asp Glu Glu Val Leu Val Ser Gly
        115                 120                 125

Lys Val Asp Trp Phe Asn Gly Arg Ala Ser Met Val His Pro Asp Phe
    130                 135                 140

Met Val Lys Leu Ser Glu Ala Glu Asn Leu Pro Leu Val Glu Ala Val
145                 150                 155                 160

Tyr Pro Met Thr Ala Gly Leu Ser Pro Lys Val Leu Arg Arg Ala Ile

-continued

```
                165                 170                 175
Glu Gly Gly Leu Ser Lys Leu Pro Val Phe Pro Glu Trp Ile Asp Glu
            180                 185                 190

Thr Leu Lys Thr Arg Gln Gly Phe Gly Asp Val Ala Ser Ser Phe Arg
        195                 200                 205

Glu Leu His Asp Pro Arg Asp Ser Ala Asp Ile Asp Pro Gln Ala Pro
    210                 215                 220

Ala Arg Arg Arg Leu Ala Tyr Asp Glu Phe Leu Ala Gly Gln Leu Ser
225                 230                 235                 240

Leu Ala Leu Val Arg Gln Arg Leu Arg Lys Val Ala Gly Gln Pro Ile
            245                 250                 255

Arg Ala Lys Gly Asp Ile Ala Ala Lys Ile Leu Ser Gln Leu Pro Phe
        260                 265                 270

Ser Leu Thr Pro Ser Gln Asn Ala Ser Val Lys Asp Ile Leu Thr Asp
    275                 280                 285

Met Ala Ser Glu Asp Arg Met Leu Arg Leu Leu Gln Gly Asp Val Gly
    290                 295                 300

Ala Gly Lys Thr Leu Val Ala Leu Met Ala Met Ala Thr Ala Val Glu
305                 310                 315                 320

Ala Gly Gly Gln Ala Val Leu Met Ala Pro Thr Glu Ile Leu Ala Arg
            325                 330                 335

Gln His Phe Ala Thr Ile Ser Lys Leu Ala Asn Ala Val Gly Ile Thr
        340                 345                 350

Val Glu Val Leu Thr Gly Arg Thr Lys Gly Lys Glu Arg Arg Glu Ile
    355                 360                 365

Glu Glu Arg Val Ala Ser Gly Glu Ala Gln Ile Val Ile Gly Thr His
    370                 375                 380

Ala Leu Phe Gln Asp Ser Val Ser Tyr Lys Asn Leu Val Leu Ala Val
385                 390                 395                 400

Val Asp Glu Gln His Arg Phe Gly Val His Gln Arg Leu Arg Leu Thr
            405                 410                 415

Ala Lys Gly Ile Thr Pro His Met Leu Val Met Thr Ala Thr Pro Ile
        420                 425                 430

Pro Arg Thr Leu Val Leu Ala Ala Phe Gly Asp Met Asp Val Ser Lys
    435                 440                 445

Leu Thr Glu Lys Pro Ala Gly Arg Lys Pro Ile Gln Thr Val Thr Ile
    450                 455                 460

Pro Thr Glu Arg Ile Gly Asp Ile Val Glu Arg Leu Arg Ala Ala Leu
465                 470                 475                 480

Lys Glu Gly Lys Lys Ala Tyr Trp Ile Cys Pro Leu Val Glu Glu Thr
            485                 490                 495

Glu Glu Ser Asp Leu Met Ser Ala Glu Arg His Ala Val Leu Ser
        500                 505                 510

Gln Met Leu Gly Ala Asn Ile Gly Leu Ile His Gly Arg Met Ser Gly
    515                 520                 525

Pro Glu Lys Asp Ala Ala Met Leu Ala Phe Lys Asn Gly Glu Thr Arg
    530                 535                 540

Leu Leu Val Ala Thr Thr Val Glu Val Gly Val Asp Val Pro Asp
545                 550                 555                 560

Ala Thr Ile Met Val Ile Glu His Ala Glu Arg Phe Gly Leu Ala Gln
            565                 570                 575

Leu His Gln Leu Arg Gly Arg Val Gly Arg Gly Asp Glu Ala Ser Thr
        580                 585                 590
```

```
Cys Ile Leu Leu Tyr Lys Gly Pro Leu Ser Glu Asn Gly Arg Ala Arg
            595                 600                 605

Leu Ser Ile Leu Arg Asp Ser Glu Asp Gly Phe Leu Ile Ala Glu Glu
        610                 615                 620

Asp Leu Lys Leu Arg Gly Glu Gly Glu Leu Leu Gly Thr Arg Gln Ser
625                 630                 635                 640

Gly Thr Pro Gly Phe Arg Ile Ala Ser Leu Glu Ala His Ala Asp Leu
                645                 650                 655

Leu Glu Ile Ala Arg Lys Asp Ala Ala Tyr Val Ile Glu Arg Asp Pro
            660                 665                 670

Glu Leu Thr Gly Pro Arg Gly Glu Ser Leu Arg Thr Leu Leu Tyr Leu
        675                 680                 685

His Arg Arg Asp Glu Ala Ile Arg Phe Leu His Ala Gly
690                 695                 700

<210> SEQ ID NO 21
<211> LENGTH: 1809
<212> TYPE: DNA
<213> ORGANISM: Agrobacterium tumefaciens

<400> SEQUENCE: 21
atggcaatga tggagccggc cgataccgtg gtccgcgcat tcttagcgt ggagcggtcg      60 gcgacagagc aacgttgggt ttcgcggctg atcaggccg cacagaaccg tgcgctggcc     120
atgtcccaga tccatgccat tcccgaactg attgcccggg tgctggccgg gcgaggggtg    180
ggggtggatg aggctctcgc tttcctcgat ccgaccattc gctcattgat gcccgacccg    240
catgtgctga cagattgcga aaaggctgcc gaaaggctgg tccgcgccat tgagaccggc    300
gagaaggtgg cgatcttcgg cgattatgac gttgatggcg ccgcgtcttc cgcgctgatg    360
tatcggtttc tcgcacattt cgggctgacg ccggaaatct atattccaga tcgtattttc    420
gagggttatg ggccgaaccc ggcggcgatg cagcagcttg ccgccaatgg cgcgaccctg    480
atcgtgacgg ttgattgcgg ctccaccagc catgaatcgc tgaatgccgc aaaggatgcg    540
ggaacagatg tggtggtgat cgatcaccac caggtcggtt cggaactgcc gccgcggtg    600 gcgttggtca atcccaaccg gaagacgat ctttcggggc aggggcatct ctgcgccgca    660
ggcgtggtgt ttctggttct ggtcgccacc ctcaggctgt gaaggacag gcgcaacaga    720 caggcgttca cgatcgatct gctggcgctg ctggatatag tcgcactcgc aaccgtatgc    780
gacgtggtgc ccttgaaggg gctgaaccgc gcctatgtgg taaaggggtt gattgccgcg    840
cgccatatga caacgccgg gctggcggcg ctgttcagaa aggcggggtt gggcgggccg    900
gtgacaccgt atcatttcgg tttcctgatc gggccacgca tcaatgccgg tggccgtatt    960
ggcgatgccg cactgggtag ccgtctgctt acactcgacg actcgtcaca ggcggacgtg   1020
attgccgaaa agctggatga gctcaaccgc gagcgacagg cgatggaagc cgtgatgctg   1080
gcggaagccg aagcggaagc gctttatgag tatggcgacg gctctggcgc tggcgtcatc   1140
gttaccgcac gggaaaactg gcatccgggg atcgttggcc tgcttgcctc acgcctcaag   1200
gaccgtttcc gccgcccggc ctttgcaatc gctttcgatc cctctggcaa gggcacaggc   1260
tccggccgct cgatcaatgg tttcgatatg gcagaatgg tccgcgccgc tgtggatgcc   1320
ggcctgctgg tcaagggtgg cggtcacgcc atgccgcgg gcctgacggt ggaacgcgcc   1380
aatctcggca aactccggac cttcttcgag gaagccgccg caaagacggt gagcgagctg   1440
gtggaaagca gcgtgcttaa gatcgacggc gcaatcggcg cgtccggtgc gaccctgcag   1500
```

```
cttgtcgatc agctggaaca ggctggtcct tatggctccg gccattctca gcccattttt    1560
gccgtgcctg cccaccggct gcgcgatgtg cgtctggtcg gcacctccca cgtcaagatc    1620
acgctggagg ccatggatgg ctcacggctg gacggcatcg cattccgcgc cgcagaggcc    1680
cctctggggc agatgctgct gaatgcgcgt ggcaggtcta tccacgtggc aggcaccgtg    1740
ggtgccgatc tctggcaggg ccagaggcgt gtgcagctgc gtgttctgga cgcggctttc    1800
gcgccctga                                                            1809
```

<210> SEQ ID NO 22
<211> LENGTH: 602
<212> TYPE: PRT
<213> ORGANISM: Agrobacterium tumefaciens

<400> SEQUENCE: 22

```
Met Ala Met Met Glu Pro Ala Asp Thr Val Arg Ala Phe Leu Ser
1               5                   10                  15

Val Glu Arg Ser Ala Thr Glu Gln Arg Trp Val Ser Arg Leu Asp Gln
            20                  25                  30

Ala Ala Gln Asn Arg Ala Leu Ala Met Ser Gln Ile His Ala Ile Pro
        35                  40                  45

Glu Leu Ile Ala Arg Val Leu Ala Gly Arg Gly Val Gly Val Asp Glu
    50                  55                  60

Ala Leu Ala Phe Leu Asp Pro Thr Ile Arg Ser Leu Met Pro Asp Pro
65                  70                  75                  80

His Val Leu Thr Asp Cys Glu Lys Ala Ala Glu Arg Leu Val Arg Ala
                85                  90                  95

Ile Glu Thr Gly Glu Lys Val Ala Ile Phe Gly Asp Tyr Asp Val Asp
            100                 105                 110

Gly Ala Ala Ser Ser Ala Leu Met Tyr Arg Phe Leu Ala His Phe Gly
        115                 120                 125

Leu Thr Pro Glu Ile Tyr Ile Pro Asp Arg Ile Phe Glu Gly Tyr Gly
    130                 135                 140

Pro Asn Pro Ala Ala Met Gln Gln Leu Ala Ala Asn Gly Ala Thr Leu
145                 150                 155                 160

Ile Val Thr Val Asp Cys Gly Ser Thr Ser His Glu Ser Leu Asn Ala
                165                 170                 175

Ala Lys Asp Ala Gly Thr Asp Val Val Ile Asp His His Gln Val
            180                 185                 190

Gly Ser Glu Leu Pro Pro Ala Val Ala Leu Val Asn Pro Asn Arg Glu
        195                 200                 205

Asp Asp Leu Ser Gly Gln Gly His Leu Cys Ala Ala Gly Val Val Phe
    210                 215                 220

Leu Val Leu Val Ala Thr Leu Arg Leu Leu Lys Asp Arg Arg Asn Arg
225                 230                 235                 240

Gln Ala Phe Thr Ile Asp Leu Leu Ala Leu Asp Ile Val Ala Leu
                245                 250                 255

Ala Thr Val Cys Asp Val Val Pro Leu Lys Gly Leu Asn Arg Ala Tyr
            260                 265                 270

Val Val Lys Gly Leu Ile Ala Ala Arg His Met Asn Asn Ala Gly Leu
        275                 280                 285

Ala Ala Leu Phe Arg Lys Ala Gly Leu Gly Gly Pro Val Thr Pro Tyr
    290                 295                 300

His Phe Gly Phe Leu Ile Gly Pro Arg Ile Asn Ala Gly Gly Arg Ile
```

```
                305                 310                 315                 320
            Gly Asp Ala Ala Leu Gly Ser Arg Leu Leu Thr Leu Asp Asp Ser Ser
                            325                 330                 335
            Gln Ala Asp Val Ile Ala Glu Lys Leu Asp Glu Leu Asn Arg Glu Arg
                            340                 345                 350
            Gln Ala Met Glu Ala Val Met Leu Ala Glu Ala Glu Ala Glu Ala Leu
                            355                 360                 365
            Tyr Glu Tyr Gly Asp Gly Ser Gly Ala Gly Val Ile Val Thr Ala Arg
                            370                 375                 380
            Glu Asn Trp His Pro Gly Ile Val Gly Leu Leu Ala Ser Arg Leu Lys
            385                 390                 395                 400
            Asp Arg Phe Arg Arg Pro Ala Phe Ala Ile Ala Phe Asp Pro Ser Gly
                            405                 410                 415
            Lys Gly Thr Gly Ser Gly Arg Ser Ile Asn Gly Phe Asp Met Gly Arg
                            420                 425                 430
            Met Val Arg Ala Ala Val Asp Ala Gly Leu Leu Val Lys Gly Gly Gly
                            435                 440                 445
            His Ala Met Ala Ala Gly Leu Thr Val Glu Arg Ala Asn Leu Gly Lys
                            450                 455                 460
            Leu Arg Thr Phe Phe Glu Glu Ala Ala Ala Lys Thr Val Ser Glu Leu
            465                 470                 475                 480
            Val Glu Ser Ser Val Leu Lys Ile Asp Gly Ala Ile Gly Ala Ser Gly
                            485                 490                 495
            Ala Thr Leu Gln Leu Val Asp Gln Leu Glu Gln Ala Gly Pro Tyr Gly
                            500                 505                 510
            Ser Gly His Ser Gln Pro Ile Phe Ala Val Pro Ala His Arg Leu Arg
                            515                 520                 525
            Asp Val Arg Leu Val Gly Thr Ser His Val Lys Ile Thr Leu Glu Ala
                            530                 535                 540
            Met Asp Gly Ser Arg Leu Asp Gly Ile Ala Phe Arg Ala Ala Glu Ala
            545                 550                 555                 560
            Pro Leu Gly Gln Met Leu Leu Asn Ala Arg Gly Arg Ser Ile His Val
                            565                 570                 575
            Ala Gly Thr Val Gly Ala Asp Leu Trp Gln Gly Gln Arg Arg Val Gln
                            580                 585                 590
            Leu Arg Val Leu Asp Ala Ala Phe Ala Pro
                            595                 600

<210> SEQ ID NO 23
<211> LENGTH: 1674
<212> TYPE: DNA
<213> ORGANISM: Agrobacterium tumefaciens

<400> SEQUENCE: 23
atgctggtcc agctctcgat tcgtgacatc gttctgattg aaaggctcga cctcggcttt      60
gaggcgggcc tttccgtgtt gacgggtgag acgggcgcgg gcaaatccat tctgcttgac     120
agcctgtcgc tggccctcgg gggccgcggc gatggcggtc tggtgcgcca cggtgaagag     180
aagggacagg tcactgccac tttcgaagtt ccgaacagcc accccacacg gcatctcctg     240
cgcgaaaacg gcctcgatga cgatggcgac ctgatttttc cgccgcgtgc aatccgcaga      300
ggacgcacca aggcctatat caacgatcag gccatcagcg tgcagatgat gcgtcagctg     360
gggcagctat tggtcgaaat tcacggccag cacgacgacc gcgctcttgt cgataccgat     420
gcccaccgca cgctgctgga tgctttcgcc gggctgagcg acgatgcccg tgccgttcag     480
```

-continued

```
ggtttctacc gcacatggaa ggacgccgag cgggcattga aaactcatcg tgccaaggtt      540
gaggctgctg cccgagaggc ggactatctg cgttcctccg tcgaggagct tgaggtgctc      600
tcgccgcgcg acggcgagga ggaggagctt gccgaacgtc gggcggtgat gcagaaatcc      660
gaacgtattg ccggtgatat cgccgaagcg agcgagttcc tgaacggcaa cgcctcgcca      720
gtgcccatga tcgcatccat gatgcggcgc ctggaacgca agagccacga ggcgccggga      780
ttgctggaag acaccgtgca attgttggat gccgcgctcg acagcctttc caacgcgcag      840
atggaagtgg aggccgcact tcgccgcacc gagttcgatc cacgcgagct ggagcgggtg      900
gaggaacggc tgtttgcgct acgcgccgcc ggacgcaaat ataatgtcgc ggtgcctgat      960
ctgccggcga ttgcggaaaa aatggtcgcg gatcttgccg acctcgatgc gggcgaagaa     1020
aagctcggca aacttgaagc caatctcggc gttgtgaaag ccaatttcga ccacgcggcc     1080
aaatcgcttt ccgaaaaacg ccacaatgcg gcgaacgcgc tttccgaagc tgtcatggcg     1140
gagcttccgg cgctcaagct ggagcgggca cgttttaccg tcgaagtcag ctccgacccg     1200
gagcaagcga cggctgacgg tatcgacatc gtggaattcc acgttcagac caatcctgga     1260
acgcggcccg gccgatcat gaaagtcgct tctggcggcg aattgtcccg tttcctgctg     1320
gcgcttaaag tcgcgctggc ggatcgtggt tcggcaccga cactggtgtt cgacgaaatc     1380
gacacgggcg ttggcggcgc tgtggcagat gccattggcc aaaggctgcg tcgtctgtcg     1440
aaaaccgtgc aggttctgtc cgtcacccac gcgccccagg tggccgcgcg gcggccaca      1500
catcttctca tttccaaagg cccctccggc gacggcaccg agcgcatcgc cacgcgtgtc     1560
gctaccatgg agccgaaaca tcgcaccgaa gaaatcgccc gcatgcttgc cggtgcctcg     1620
gtgacagatg aggcgagggc tgctgccgcc cgcctgcttg ccgccaagga ttaa           1674
```

<210> SEQ ID NO 24
<211> LENGTH: 557
<212> TYPE: PRT
<213> ORGANISM: Agrobacterium tumefaciens

<400> SEQUENCE: 24

```
Met Leu Val Gln Leu Ser Ile Arg Asp Ile Val Leu Ile Glu Arg Leu
1               5                   10                  15

Asp Leu Gly Phe Glu Ala Gly Leu Ser Val Leu Thr Gly Glu Thr Gly
            20                  25                  30

Ala Gly Lys Ser Ile Leu Leu Asp Ser Leu Ser Leu Ala Leu Gly Gly
        35                  40                  45

Arg Gly Asp Gly Gly Leu Val Arg His Gly Glu Lys Gly Gln Val
    50                  55                  60

Thr Ala Thr Phe Glu Val Pro Asn Ser His Pro Thr Arg His Leu Leu
65                  70                  75                  80

Arg Glu Asn Gly Leu Asp Asp Asp Gly Asp Leu Ile Phe Arg Arg Val
                85                  90                  95

Gln Ser Ala Asp Gly Arg Thr Lys Ala Tyr Ile Asn Asp Gln Ala Ile
            100                 105                 110

Ser Val Gln Met Met Arg Gln Leu Gly Gln Leu Leu Val Glu Ile His
        115                 120                 125

Gly Gln His Asp Asp Arg Ala Leu Val Asp Thr Asp Ala His Arg Thr
    130                 135                 140

Leu Leu Asp Ala Phe Ala Gly Leu Ser Asp Asp Ala Arg Ala Val Gln
145                 150                 155                 160
```

Gly Phe Tyr Arg Thr Trp Lys Asp Ala Glu Arg Ala Leu Lys Thr His
                165                 170                 175

Arg Ala Lys Val Glu Ala Ala Arg Glu Ala Asp Tyr Leu Arg Ser
        180                 185                 190

Ser Val Glu Glu Leu Glu Val Leu Ser Pro Arg Asp Gly Glu Glu Glu
        195                 200                 205

Glu Leu Ala Glu Arg Arg Ala Val Met Gln Lys Ser Glu Arg Ile Ala
        210                 215                 220

Gly Asp Ile Ala Glu Ala Ser Glu Phe Leu Asn Gly Asn Ala Ser Pro
225                 230                 235                 240

Val Pro Met Ile Ala Ser Met Met Arg Arg Leu Glu Arg Lys Ser His
                245                 250                 255

Glu Ala Pro Gly Leu Leu Glu Asp Thr Val Gln Leu Leu Asp Ala Ala
            260                 265                 270

Leu Asp Ser Leu Ser Asn Ala Gln Met Glu Val Glu Ala Ala Leu Arg
        275                 280                 285

Arg Thr Glu Phe Asp Pro Arg Glu Leu Glu Arg Val Glu Glu Arg Leu
        290                 295                 300

Phe Ala Leu Arg Ala Ala Gly Arg Lys Tyr Asn Val Ala Val Pro Asp
305                 310                 315                 320

Leu Pro Ala Ile Ala Glu Lys Met Val Ala Asp Leu Ala Asp Leu Asp
                325                 330                 335

Ala Gly Glu Glu Lys Leu Gly Lys Leu Glu Ala Asn Leu Gly Val Val
            340                 345                 350

Lys Ala Asn Phe Asp His Ala Ala Lys Ser Leu Ser Glu Lys Arg His
        355                 360                 365

Asn Ala Ala Asn Ala Leu Ser Glu Ala Val Met Ala Glu Leu Pro Ala
370                 375                 380

Leu Lys Leu Glu Arg Ala Arg Phe Thr Val Glu Val Ser Ser Asp Pro
385                 390                 395                 400

Glu Gln Ala Thr Ala Asp Gly Ile Asp Ile Val Glu Phe His Val Gln
                405                 410                 415

Thr Asn Pro Gly Thr Arg Pro Gly Pro Ile Met Lys Val Ala Ser Gly
            420                 425                 430

Gly Glu Leu Ser Arg Phe Leu Leu Ala Leu Lys Val Ala Leu Ala Asp
        435                 440                 445

Arg Gly Ser Ala Pro Thr Leu Val Phe Asp Glu Ile Asp Thr Gly Val
450                 455                 460

Gly Gly Ala Val Ala Asp Ala Ile Gly Gln Arg Leu Arg Arg Leu Ser
465                 470                 475                 480

Lys Thr Val Gln Val Leu Ser Val Thr His Ala Pro Gln Val Ala Ala
                485                 490                 495

Arg Ala Ala Thr His Leu Leu Ile Ser Lys Gly Pro Ser Gly Asp Gly
            500                 505                 510

Thr Glu Arg Ile Ala Thr Arg Val Ala Thr Met Glu Pro Lys His Arg
        515                 520                 525

Thr Glu Glu Ile Ala Arg Met Leu Ala Gly Ala Ser Val Thr Asp Glu
        530                 535                 540

Ala Arg Ala Ala Ala Arg Leu Leu Ala Ala Lys Asp
545                 550                 555

<210> SEQ ID NO 25
<211> LENGTH: 765
<212> TYPE: DNA

<213> ORGANISM: Agrobacterium tumefaciens

<400> SEQUENCE: 25

```
atgcagtggc aggacgaggc aatcattctc ggcgtaaagc gtcatggcga gaccagcgtc    60
atcgccgagg tgatgacccg tttgcgcggc cgccatctgg ggatggtgcg cggcgggcgc   120
tcccgcagca tgcagccggt gctgcaggcg ggaaaccggg tggatgtgat ctggcgggcg   180
cggcttgacg accatctcgg cgaattccgc attgagcctt tgcagttgcg ggcagcgcaa   240
ttgatggaaa cggcaaccgc cgtgtatggc gtgcaggcca tgggcgcgct gctgcggctt   300
ctgccggagc gtgacccgca tccgcatctc tatcaggcgc tcgacgtcat tctcgacaat   360
ctccatgatc cggtcgatgc tggcgaattg ttcgtacggt tcgagctggc ggtgctgaac   420
gatcttggtt tcggtctcga tctcacggaa tgcgcggcaa cgggcctgcg caccgatctc   480
atctatgtat cgcccaaaac gggcagggcg gtctgtagta cggcgggcgc gccctatgcg   540
gcgcgtatgc tttcgcttcc cgctttcctg agcgaaggtc agtcgaaggc ggccgaccgc   600
gacagcctcg cggcagcctt cgcctgacc ggccattttc tccaccggca tgtctatgat    660
ccgcgcggcc tcaatgaaaa cgccgcccgc gacggtttcg tgcaggcggc gttgaaggca   720
ctggagcgca aggcggtgct gcctgcgctc gataaggcgg tatag                   765
```

<210> SEQ ID NO 26
<211> LENGTH: 254
<212> TYPE: PRT
<213> ORGANISM: Agrobacterium tumefaciens

<400> SEQUENCE: 26

```
Met Gln Trp Gln Asp Glu Ala Ile Ile Leu Gly Val Lys Arg His Gly
  1               5                  10                  15

Glu Thr Ser Val Ile Ala Glu Val Met Thr Arg Leu Arg Gly Arg His
             20                  25                  30

Leu Gly Met Val Arg Gly Gly Arg Ser Arg Ser Met Gln Pro Val Leu
         35                  40                  45

Gln Ala Gly Asn Arg Val Asp Val Ile Trp Arg Ala Arg Leu Asp Asp
     50                  55                  60

His Leu Gly Glu Phe Arg Ile Glu Pro Leu Gln Leu Arg Ala Ala Gln
 65                  70                  75                  80

Leu Met Glu Thr Ala Thr Ala Val Tyr Gly Val Gln Ala Met Gly Ala
                 85                  90                  95

Leu Leu Arg Leu Leu Pro Glu Arg Asp Pro His Pro His Leu Tyr Gln
            100                 105                 110

Ala Leu Asp Val Ile Leu Asp Asn Leu His Asp Pro Val Asp Ala Gly
        115                 120                 125

Glu Leu Phe Val Arg Phe Glu Leu Ala Val Leu Asn Asp Leu Gly Phe
    130                 135                 140

Gly Leu Asp Leu Thr Glu Cys Ala Ala Thr Gly Leu Arg Thr Asp Leu
145                 150                 155                 160

Ile Tyr Val Ser Pro Lys Thr Gly Arg Ala Val Cys Ser Thr Ala Gly
                165                 170                 175

Ala Pro Tyr Ala Ala Arg Met Leu Ser Leu Pro Ala Phe Leu Ser Glu
            180                 185                 190

Gly Gln Ser Lys Ala Ala Asp Arg Asp Ser Leu Ala Ala Ala Phe Arg
        195                 200                 205

Leu Thr Gly His Phe Leu His Arg His Val Tyr Asp Pro Arg Gly Leu
    210                 215                 220
```

Asn Glu Asn Ala Ala Arg Asp Gly Phe Val Gln Ala Ala Leu Lys Ala
225                 230                 235                 240

Leu Glu Arg Lys Ala Val Leu Pro Ala Leu Asp Lys Ala Val
                245                 250

<210> SEQ ID NO 27
<211> LENGTH: 1809
<212> TYPE: DNA
<213> ORGANISM: Agrobacterium tumefaciens

<400> SEQUENCE: 27

| | | | | | |
|---|---|---|---|---|---|
| gtgaccaccg | atcccttgca | gattctcaag | accgtgtatg | gctacgatac | gtttcgtgga | 60 |
| cagcaggccg | aaatcatccg | gcatgtgatg | gcaggcaaca | atgcatttgt | attgatgcca | 120 |
| acaggggcg | ggaagtcgct | ttgttaccag | attccggcgc | tcgcccgtaa | gggaatgggg | 180 |
| ctggttgttt | cgcccctgat | cgcgctgatg | gttgatcagg | tcgccgcctt | gcgtcaggca | 240 |
| ggtgtgcggg | cagaagctct | caactccgat | cttcccccag | aagagcggcg | gatactctgg | 300 |
| caggatatgc | gggctggcaa | ggtcgatatt | ctctatgccg | cgccggagac | ccttctcaag | 360 |
| ccggatgttc | tggatgcgct | tcaacctatc | agcctgtcgc | tgatcgccat | cgacgaagct | 420 |
| cattgcctgt | cgcagtgggg | gcacgatttc | cgtcccccct | accgccagct | agacacgttg | 480 |
| atcgagcgct | ttccggatac | gccacgcatg | gcgctcacgg | cgactgcgga | cgagccaacc | 540 |
| cgcgccgaaa | ttctgggtca | tctcgggatc | aacggaagcg | acgccttcat | agccggattc | 600 |
| gatcggccaa | atatccgcta | tgcgatcatg | gaaaaggata | atccacgtac | gcagctgaag | 660 |
| cgcttcctga | cgggtcgcga | ggacgaaagc | ggcatcgtct | attgcctttc | caaacgcaag | 720 |
| gtagatgaga | cggcggcctg | gctgcgtgag | gaggggcgcg | atgcgctgcc | ctatcacgcc | 780 |
| ggcatggaca | aggccgcccg | cgaggcgaac | cagacccact | tccagcatgg | tgaagctgtc | 840 |
| atcatggttg | caaccgtggc | tttcggtatg | ggcatcgaca | aaccggatgt | gcgcttcgtt | 900 |
| gtgcatatcg | atctgcccag | cagcatcgaa | gcctattatc | aggaaaccgg | ccgtgccggc | 960 |
| cgtgacggtc | tgccgtccga | cgtgcttatg | ctttacggtt | atgaagacat | cgcattgcgc | 1020 |
| aaccgctttta | tcgaagagtc | ggatgcgggc | gaccagcgca | agaacatgga | gcgccggaag | 1080 |
| ctcgatgcgt | tgcttggcct | cgcggaaaca | gccggttgcc | gtcggcgggt | gcttttgtct | 1140 |
| tatttcggcg | accattgtga | gccctgcggc | aattgcgaca | cctgtgcgga | gccgccggac | 1200 |
| ctgtttgatg | gtgccattgc | cgcgcagaag | ttgctgtcct | gcatttaccg | cacgggagaa | 1260 |
| cgtttcggcc | aggcctatgt | catccgcgta | ttgctgggca | tggaagatga | acggatatcg | 1320 |
| aactttggtc | acgatcggat | cacgacctac | ggcatcggca | agagcacga | caatcgcacc | 1380 |
| tggcgggcca | tcctgcgcca | gatggttgcg | ctgcgcctga | tcgagttga | tctggccggt | 1440 |
| cacggggat | tgtccatttc | cgaagaaggg | aggcggttcc | tgcgcgaaaa | gccgtccctg | 1500 |
| atgttgagga | taccgtccgc | tccccgttcg | gcgcgacaac | agacgaatcg | caagcccacc | 1560 |
| gccattgttc | taccggatgc | cgatcgtagt | ctctttgagg | cgctgcgtgc | gaagcgcatg | 1620 |
| gaaattgccc | gcgcacagaa | cgttccgccc | tatgtgattt | tcacgacaa | gacactcatt | 1680 |
| gagcttgcgc | catcaagacc | ggcctctgtg | ggggaaatgg | cgcagatacc | tggagtggga | 1740 |
| gacacaaagc | tggaacgata | cggccctgct | tttctggcgg | cgatcatgga | acatgccgcc | 1800 |
| agcgagtga | | | | | 1809 |

<210> SEQ ID NO 28

<211> LENGTH: 602
<212> TYPE: PRT
<213> ORGANISM: Agrobacterium tumefaciens

<400> SEQUENCE: 28

```
Val Thr Thr Asp Pro Leu Gln Ile Leu Lys Thr Val Tyr Gly Tyr Asp
1               5                   10                  15

Thr Phe Arg Gly Gln Gln Ala Glu Ile Ile Arg His Val Met Ala Gly
                20                  25                  30

Asn Asn Ala Phe Val Leu Met Pro Thr Gly Gly Lys Ser Leu Cys
            35                  40                  45

Tyr Gln Ile Pro Ala Leu Ala Arg Lys Gly Met Gly Leu Val Val Ser
    50                  55                  60

Pro Leu Ile Ala Leu Met Val Asp Gln Val Ala Ala Leu Arg Gln Ala
65                  70                  75                  80

Gly Val Arg Ala Glu Ala Leu Asn Ser Asp Leu Ser Pro Glu Glu Arg
                85                  90                  95

Arg Ile Leu Trp Gln Asp Met Arg Ala Gly Lys Val Asp Ile Leu Tyr
            100                 105                 110

Ala Ala Pro Glu Thr Leu Leu Lys Pro Asp Val Leu Asp Ala Leu Gln
        115                 120                 125

Pro Ile Ser Leu Ser Leu Ile Ala Ile Asp Glu Ala His Cys Leu Ser
    130                 135                 140

Gln Trp Gly His Asp Phe Arg Pro Pro Tyr Arg Gln Leu Asp Thr Leu
145                 150                 155                 160

Ile Glu Arg Phe Pro Asp Thr Pro Arg Met Ala Leu Thr Ala Thr Ala
                165                 170                 175

Asp Glu Pro Thr Arg Ala Glu Ile Leu Gly His Leu Gly Ile Asn Gly
            180                 185                 190

Ser Asp Ala Phe Ile Ala Gly Phe Asp Arg Pro Asn Ile Arg Tyr Ala
        195                 200                 205

Ile Met Glu Lys Asp Asn Pro Arg Thr Gln Leu Lys Arg Phe Leu Thr
    210                 215                 220

Gly Arg Glu Asp Glu Ser Gly Ile Val Tyr Cys Leu Ser Lys Arg Lys
225                 230                 235                 240

Val Asp Glu Thr Ala Ala Trp Leu Arg Glu Glu Gly Arg Asp Ala Leu
                245                 250                 255

Pro Tyr His Ala Gly Met Asp Lys Ala Ala Arg Glu Ala Asn Gln Thr
            260                 265                 270

His Phe Gln His Gly Glu Ala Val Ile Met Val Ala Thr Val Ala Phe
        275                 280                 285

Gly Met Gly Ile Asp Lys Pro Asp Val Arg Phe Val Val His Ile Asp
    290                 295                 300

Leu Pro Ser Ser Ile Glu Ala Tyr Tyr Gln Glu Thr Gly Arg Ala Gly
305                 310                 315                 320

Arg Asp Gly Leu Pro Ser Asp Val Leu Met Leu Tyr Gly Tyr Glu Asp
                325                 330                 335

Ile Ala Leu Arg Asn Arg Phe Ile Glu Glu Ser Asp Ala Gly Asp Gln
            340                 345                 350

Arg Lys Asn Met Glu Arg Arg Lys Leu Asp Ala Leu Leu Gly Leu Ala
        355                 360                 365

Glu Thr Ala Gly Cys Arg Arg Arg Val Leu Leu Ser Tyr Phe Gly Asp
    370                 375                 380

His Cys Glu Pro Cys Gly Asn Cys Asp Thr Cys Ala Glu Pro Pro Asp
```

```
                385                 390                 395                 400
Leu Phe Asp Gly Ala Ile Ala Ala Gln Lys Leu Leu Ser Cys Ile Tyr
                    405                 410                 415
Arg Thr Gly Glu Arg Phe Gly Gln Ala Tyr Val Ile Arg Val Leu Leu
                    420                 425                 430
Gly Met Glu Asp Glu Arg Ile Ser Asn Phe Gly His Asp Arg Ile Thr
                    435                 440                 445
Thr Tyr Gly Ile Gly Lys Glu His Asp Asn Arg Thr Trp Arg Ala Ile
                    450                 455                 460
Leu Arg Gln Met Val Ala Leu Arg Leu Ile Glu Val Asp Leu Ala Gly
465                 470                 475                 480
His Gly Gly Leu Ser Ile Ser Glu Glu Gly Arg Arg Phe Leu Arg Glu
                    485                 490                 495
Lys Pro Ser Leu Met Leu Arg Ile Pro Ser Ala Pro Arg Ser Ala Arg
                    500                 505                 510
Gln Gln Thr Asn Arg Lys Pro Thr Ala Ile Val Leu Pro Asp Ala Asp
                    515                 520                 525
Arg Ser Leu Phe Glu Ala Leu Arg Ala Lys Arg Met Glu Ile Ala Arg
                    530                 535                 540
Ala Gln Asn Val Pro Pro Tyr Val Ile Phe His Asp Lys Thr Leu Ile
545                 550                 555                 560
Glu Leu Ala Ala Ser Arg Pro Ser Val Gly Glu Met Ala Gln Ile
                    565                 570                 575
Pro Gly Val Gly Asp Thr Lys Leu Glu Arg Tyr Gly Pro Ala Phe Leu
                    580                 585                 590
Ala Ala Ile Met Glu His Ala Ala Ser Glu
                    595                 600

<210> SEQ ID NO 29
<211> LENGTH: 606
<212> TYPE: DNA
<213> ORGANISM: Agrobacterium tumefaciens

<400> SEQUENCE: 29
atggcaaaac gagtcaccgg tcccgaaatc gaaaaactga tccagctgct tgcaaaagtg      60
ccggggcttg gccccgctc ggcgcggcgg gcggcgctgc atctcatcaa gaagaaggaa      120
cagcttcttg accgctggg ccacgcgatg ggtgaagcct atgacaaggt gaagatctgc      180
tcgtgctgcg gcaatgtcga taccatcgat ccctgcacgg tctgcgccga tgatagacgt      240
gaccagtcgg tcatcatcgt ggtggaagac gtgtcggatc tgtgggcgct ggagcgagca      300
ggcgcaatga ataccgcata tcatgtgctt ggtggcacgc atcgccgct cgatggcgtc      360 gggccggaag atctgaacat caagggactg atcgatcgcg tcagcgccgg cggtattcgc      420
gagctcatca tcgccgtcaa tgcgacggtg gagggacagg caacagccca ttacatcacc      480
gaccgcctgg ccgatctcgg catcaagatc acccggcttg cgcatggcgt gcctgttggc      540
ggcgagctgg actatctcga cgagggcaca ttgacggcgg cgctgcgcgc tcgcacaacg      600
atctga                                                                606

<210> SEQ ID NO 30
<211> LENGTH: 201
<212> TYPE: PRT
<213> ORGANISM: Agrobacterium tumefaciens

<400> SEQUENCE: 30
```

Met Ala Lys Arg Val Thr Gly Pro Glu Ile Glu Lys Leu Ile Gln Leu
1               5                   10                  15

Leu Ala Lys Val Pro Gly Leu Gly Pro Arg Ser Ala Arg Ala Ala
            20                  25                  30

Leu His Leu Ile Lys Lys Lys Glu Gln Leu Leu Gly Pro Leu Gly His
        35                  40                  45

Ala Met Gly Glu Ala Tyr Asp Lys Val Lys Ile Cys Ser Cys Cys Gly
    50                  55                  60

Asn Val Asp Thr Ile Asp Pro Cys Thr Val Cys Ala Asp Asp Arg Arg
65                  70                  75                  80

Asp Gln Ser Val Ile Ile Val Glu Asp Val Ser Asp Leu Trp Ala
                85                  90                  95

Leu Glu Arg Ala Gly Ala Met Asn Thr Ala Tyr His Val Leu Gly Gly
            100                 105                 110

Thr Leu Ser Pro Leu Asp Gly Val Gly Pro Glu Asp Leu Asn Ile Lys
        115                 120                 125

Gly Leu Ile Asp Arg Val Ser Ala Gly Gly Ile Arg Glu Leu Ile Ile
    130                 135                 140

Ala Val Asn Ala Thr Val Glu Gly Gln Ala Thr Ala His Tyr Ile Thr
145                 150                 155                 160

Asp Arg Leu Ala Asp Leu Gly Ile Lys Ile Thr Arg Leu Ala His Gly
                165                 170                 175

Val Pro Val Gly Gly Glu Leu Asp Tyr Leu Asp Glu Gly Thr Leu Thr
            180                 185                 190

Ala Ala Leu Arg Ala Arg Thr Thr Ile
        195                 200

<210> SEQ ID NO 31
<211> LENGTH: 591
<212> TYPE: DNA
<213> ORGANISM: Agrobacterium tumefaciens

<400> SEQUENCE: 31
atgaccgatg attccagccc cttcctgacc gacgacatgg cactggatgg cgaaacgcag     60
gctatcgaac ccaccagccg catgctgtca tgggcgcgca attccgctct ctaccggctg    120
gaacagcgca tgatgacgga aaagcagctg cgcgatgcga tcacccgcaa ggcgcgggaa    180
aaattcgagg atatcagccc cgctcagata aaggcgcttg gcgaattcgc cgtgaccttc    240
gcctatggca tcaaggcgct cgacgatacg gcttatgcag aaattgccgt gcgaagtggc    300
cagcgcagcg gcaagtcgaa gcgcgggctt gcgcagaaac ttcagatcaa gggcattgat    360
cgggaaacgg ccgcagtcgc actgcaggaa accaacgatc tggtggcggc cgtcatcttt    420
gcgcgcaagc gcgccttcgg tcccttttcgc cgtgtcgagc ttgatgaaaa acgcaagtcg    480
aaggaatttt ctgccttcgc ccgcaacggc ttcggcttcg aaatcggcgc gaaggtgatg    540
gcgatgacgg tggaagaggc agaagagatc gtctcggaag caccgcttta a             591

<210> SEQ ID NO 32
<211> LENGTH: 196
<212> TYPE: PRT
<213> ORGANISM: Agrobacterium tumefaciens

<400> SEQUENCE: 32

Met Thr Asp Asp Ser Ser Pro Phe Leu Thr Asp Asp Met Ala Leu Asp
1               5                   10                  15

Gly Glu Thr Gln Ala Ile Glu Pro Thr Ser Arg Met Leu Ser Trp Ala

-continued

```
                    20                  25                  30
Arg Asn Ser Ala Leu Tyr Arg Leu Glu Gln Arg Met Met Thr Glu Lys
        35                  40                  45

Gln Leu Arg Asp Ala Ile Thr Arg Lys Ala Arg Glu Lys Phe Glu Asp
        50                  55                  60

Ile Ser Pro Ala Gln Ile Lys Ala Leu Gly Glu Phe Ala Val Thr Phe
65                      70                  75                  80

Ala Tyr Gly Ile Lys Ala Leu Asp Asp Thr Ala Tyr Ala Glu Ile Ala
                85                  90                  95

Val Arg Ser Gly Gln Arg Ser Gly Lys Ser Lys Arg Gly Leu Ala Gln
               100                 105                 110

Lys Leu Gln Ile Lys Gly Ile Asp Arg Glu Thr Ala Ala Val Ala Leu
        115                 120                 125

Gln Glu Thr Asn Asp Leu Val Ala Ala Val Ile Phe Ala Arg Lys Arg
        130                 135                 140

Ala Phe Gly Pro Phe Arg Arg Val Glu Leu Asp Glu Lys Arg Lys Ser
145                 150                 155                 160

Lys Glu Phe Ser Ala Phe Ala Arg Asn Gly Phe Gly Phe Glu Ile Gly
                165                 170                 175

Ala Lys Val Met Ala Met Thr Val Glu Glu Ala Glu Glu Ile Val Ser
                180                 185                 190

Glu Ala Pro Leu
            195
```

METHODS AND COMPOSITIONS FOR RECOMBINATION A GENE-DEFICIENT STRAINS OF *AGROBACTERIUM TUMEFACIENS*

BACKGROUND OF THE INVENTION

*Agrobacterium*-mediated transformation of plants results in the integration of a T-strand within the genome of the plant cell. The T-strand contains gene expression cassettes that are made up of gene regulatory elements that have been precisely engineered to link a promoter to a gene of interest and 3' untranslated region (UTR). The sequences are precisely engineered in relation to one another to optimally drive expression of the gene of interest to produce protein. The stability of the gene regulatory elements is crucial for the optimal expression of the gene of interest. Minor modification of the polynucleotide sequences that are contained within the T-strand can reduce or even eliminate expression of the gene of interest.

The *Agrobacterium tumefaciens* (LBA4404) strain is commonly used for integrating a T-strand within the genome of the plant cell. See Ooms, G., Hooykaas, P. J. J., Van Veen, R. J. M., Van Beelen, P., Regensburg-Tuienk, T. J. G., and R. A. Schilperoort (1982 "Octopine Ti-plasmid deletion mutants of *Agrobacterium tumefaciens* with emphasis on the right side of the T-region." *Plasmid* 7: 15-29; Hoekema, A., Hirsch, P. R., Hooykaas, P. J. J., and R. A. Schilperoort (1983) "A binary plant vector strategy based on separation of vir- and T-region of the *Agrobacterium tumefaciens* Ti-plasmid." *Nature* 303:179-180; and, de Frammond, A. J., Barton K. A., and M-D. Chilton (1983) "Mini-Ti: a new vector strategy for plant genetic engineering". *Biotechnology* 1: 262-269.

Despite the extensive use of *A. tumefaciens* (LBA4404) over the last thirty years, it has been observed that the plasmids transformed within this strain become unstable upon transformation within the strain. Gene regulatory elements, especially those elements that are repeated, have been observed to recombine within the *A. tumefaciens* (LBA4404) strain. This instability results in reduced plant transformation efficiency and the need to thoroughly screen potential transgenic plants for unaltered T-strand sequences. Given the instability of the plasmids transformed within this strain, a need exists for development of *Agrobacterium tumefaciens* (LBA4404) strains that do not possess recombination properties, and that can stably maintain a plasmid without rearrangements of the genetic elements located within the plasmid.

Thus, there remains a need for stains of *Agrobacterium tumefaciens* with improved plasmid stability. In particular, development for stains of *Agrobacterium tumefaciens* with deficiency in genetic recombination pathways would be desirable.

SUMMARY OF THE INVENTION

The present disclosure provides novel compositions and methods for the production and use of *Agrobacterium tumefaciens* strains (for example LBA4404) that are deficient in RecA activity relative to the parent strain. Combinations with other gene-deficient-strains of *Agrobacterium tumefaciens* are also disclosed. Specifically, two exemplary s recA minus strains, UIA777 where chloramphenicol resistant gene disrupting the recA gene and UIA770 where kanamycin resistant gene disrupting the recA gene are provided.

A deposit of *Agrobacteriuin tuinefaciens* strain UIA770 (LBA4404 recA- Kanamycin resistant) and *Agrobacteriuin tuinefaciens* strain UIA777 (LBA4404 recA- Chioramphenicol resistant) has been made with the American Type Culture Collection (ATCC), 10801 University Boulevard, Manassas, Va. 20110-2209 U.S.A., and assigned ATCC Accession No. PTA-123888 and PTA-123889, respectively. The strains were deposited with the ATCC on Mar. 7, 2017. Access to these deposits will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent.

In one aspect, provided are modified strains of *Agrobacterium tumefaciens*, wherein said modified strain is deficient in a genetic recombination pathway relative to its parent strain.

In one embodiment, the modified strain is deficient in at least one recombination pathway selected from the group consisting of RecA, RecB, RecD, RecF, RecG, RecJ, RecN, RecO, RecQ, RecR, and RecX. In another embodiment, the modified strain is deficient in RecA activity. In a further embodiment, the recA gene comprises a polynucleotide sequence having at least 60%, 65%, 70%, 75%, 80%, 85%, 90%, 95%, 98%, or 100% sequence identity with SEQ ID NO: 10 or 11. In another embodiment, the modified strain is also deficient in an activity selected from the group consisting of RecB, RecD, RecF, RecG, RecJ, RecN, RecO, RecQ, RecR, and RecX.

recA gene and RecA protein sequences are set forth in SEQ ID NOs: 10 and 12, respectively. recB gene and RecB protein sequences are set forth in SEQ ID NOs: 13 and 14, respectively. recD gene and RecD protein sequences are set forth in SEQ ID NOs: 15 and 16, respectively. recF gene and RecF protein sequences are set forth in SEQ ID NOs: 17 and 18, respectively. recG gene and RecG protein sequences are set forth in SEQ ID NOs: 19 and 20, respectively. recJ gene and RecJ protein sequences are set forth in SEQ ID NOs: 21 and 22, respectively. recN gene and RecN protein sequences are set forth in SEQ ID NOs: 23 and 24, respectively. recO gene and RecO protein sequences are set forth in SEQ ID NO: 25 and 26, respectively. recQ gene and RecQ protein sequences are set forth in SEQ ID NO: 27 and 28, respectively. recR gene and RecR protein sequences are set forth in SEQ ID NO: 29 and 30, respectively. recX gene and RecX protein sequences are set forth in SEQ ID NO: 31 and 32, respectively.

In another embodiment, a genomic recA gene is modified by a deletion, a rearrangement, or an insertion of a sequence in the recA gene. In another embodiment, a genomic recA gene is modified by inserting a sequence within the recA gene, thereby disrupting expression of RecA protein. In a further embodiment, the inserted sequence comprises a selectable marker gene. In another embodiment, the selectable marker comprises an antibiotic resistance gene selected from the group consisting of a chloramphenicol resistance gene, a kanamycin resistance gene, a spectinomycin resistance gene, a gentamycin resistance, or combinations thereof. In a further embodiment, the antibiotic resistance gene comprises a chloramphenicol resistance gene or a kanamycin resistance gene.

In one embodiment of the modified strain, RecA activity is undetectable in extracts prepared from said strain. In another embodiment, RecA protein is undetectable using Western blot analysis. In another embodiment, RecA mRNA is undetectable using Northern blot analysis. In another embodiment, recA gene is undetectable using Southern blot analysis.

In one embodiment, the recA gene encodes a protein of SEQ ID NO: 12. In another embodiment, the strain comprises a Ti plasmid. In a further embodiment, the Ti plasmid comprises a pAL4404 Ti plasmid, or is derived from pAL4404 Ti plasmid.

In one embodiment, the strain comprises a binary plasmid. In a further embodiment, the binary plasmid comprising a gene of an agronomic trait selected from the group consisting of an insecticidal resistance trait, herbicide tolerance trait, nitrogen use efficiency trait, water use efficiency trait, nutritional quality trait, DNA binding trait, selectable marker trait, and combinations thereof. In another embodiment, the strain comprises a ternary plasmid. In another embodiment, the parent strain is *Agrobacterium tumefaciens* (LBA4404).

In another aspect, provided are plasmids comprising a modified recA gene from *Agrobacterium tumefaciens*, wherein the recA gene has at least 60%, 65%, 70%, 75%, 80%, 85%, 90%, 95%, 98%, or 100% sequence identity to SEQ ID NO: 10 or 11 before modification, and the modified recA gene is deficient in expression of RecA protein.

In one embodiment, the modification comprises the insertion of a donor sequence within the recA gene or SEQ ID NO: 10 or 11. In a further embodiment, the donor sequence comprises a selectable marker gene. In another embodiment, the selectable marker gene comprises an antibiotic resistance gene selected from a chloramphenicol resistance gene, a kanamycin resistance gene, a spectinomycin resistance gene, a gentamycin resistance, or combinations thereof. In a further embodiment, the antibiotic resistance gene comprises a chloramphenicol resistance gene or a kanamycin resistance gene. In another embodiment, at least one end of the donor sequence is flanked by at least a 43 base pair fragment of SEQ ID NO: 10 or 11

In another aspect, provided are method of generating an *Agrobacterium tumefaciens* strain deficient in a genetic recombination pathway relative to its parent strain. The methods comprise
(a) providing a knock-out plasmid directed to the recA gene;
(b) introducing the knock-out plasmid into the *Agrobacterium tumefaciens* strain;
(c) selecting and screening the colonies comprising a genomic mutation; and,
(d) identifying at least one mutated *Agrobacterium tumefaciens* with a genomic mutation of recA.

In one embodiment, the recA gene has at least 60%, 65%, 70%, 75%, 80%, 85%, 90%, 95%, 98%, or 100% sequence identity to SEQ ID NO: 10 or 11. In another embodiment, the knock out plasmid induces a mutation selected from the group consisting of a genomic deletion, a genomic rearrangement, a genomic insertion, and combinations thereof. In a further embodiment, the genomic insertion comprises a sequence encoding a selectable marker. In another embodiment, the selectable marker gene comprises an antibiotic resistance gene selected from a chloramphenicol resistance gene, a kanamycin resistance gene, a spectinomycin resistance gene, a gentamycin resistance, or combinations thereof. In a further embodiment, the antibiotic resistance gene comprises a chloramphenicol resistance gene or a kanamycin resistance gene.

In another aspect, provided are transgenic events comprising (a) a T-strand insert flanked by an upstream genomic DNA border sequence and (b) a downstream genomic DNA border sequences, wherein the transgenic event comprises integration of the T-strand from a modified strain of *Agrobacterium tumefaciens*, which is deficient in a genetic recombination pathway relative to its parent strain.

In one embodiment, the T-strand from the modified strain of *Agrobacterium tumefaciens* is integrated within genomes of targeted plant cells which are used to regenerate the transgenic event. In another embodiment, the transgenic events further comprise an agronomic trait. In a further embodiment, the agronomic trait is selected from the group consisting of an insecticidal resistance trait, herbicide tolerance trait, nitrogen use efficiency trait, water use efficiency trait, nutritional quality trait, DNA binding trait, selectable marker trait, and combinations thereof. In another embodiment, the transgenic event is a dicotyledonous plant or a monocotyledonous plant.

In another embodiment, the dicotyledonous plant or monocotyledonous plant is selected from the group consisting of barley, canola, coffee, corn, cotton, flax, grapevine, hops, mustard, nuts, oat, poppy, rape, rice, rubber plant, rye, sunflower, sorghum, soybean, sugar cane, tea, tobacco, and wheat. In another embodiment, the dicotyledonous plant or monocotyledonous plant is selected from the group consisting of corn, wheat, cotton, rice, soybean, and canola. In another embodiment, the dicotyledonous plant or monocotyledonous plant is selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries.

In another aspect, provided are methods of producing a transgenic plant. The methods comprise
(a) contacting targeted plant cells with a modified strain of *Agrobacterium tumefaciens*, which is deficient in a genetic recombination pathway relative to its parent strain;
(b) selecting and screening plant cells comprising DNA from said *Agrobacterium* strain integrated into genome of the targeted plant cells; and
(c) regenerating whole transgenic plants from plant cells selected/screened in step (b).

In one embodiment, the selecting step is carried out using a selectable marker. In a further embodiment, the selectable marker gene comprises an antibiotic resistance gene selected from a chloramphenicol resistance gene, a kanamycin resistance gene, a spectinomycin resistance gene, a gentamycin resistance, or combinations thereof. In another further embodiment, the antibiotic resistance gene comprises a chloramphenicol resistance gene or a kanamycin resistance gene.

BRIEF DESCRIPTION OF THE FIGURES

FIG. 1A shows the recA gene and its neighboring sequence in pWM-RecAnei. B, XhoI restriction map of the DNA fragment from LBA4404 in pCP-MMSR2. C, Replacement of recA with cassettes encoding resistance to antibiotic Cm or Km.

DETAILED DESCRIPTION OF THE INVENTION

Figure 1:
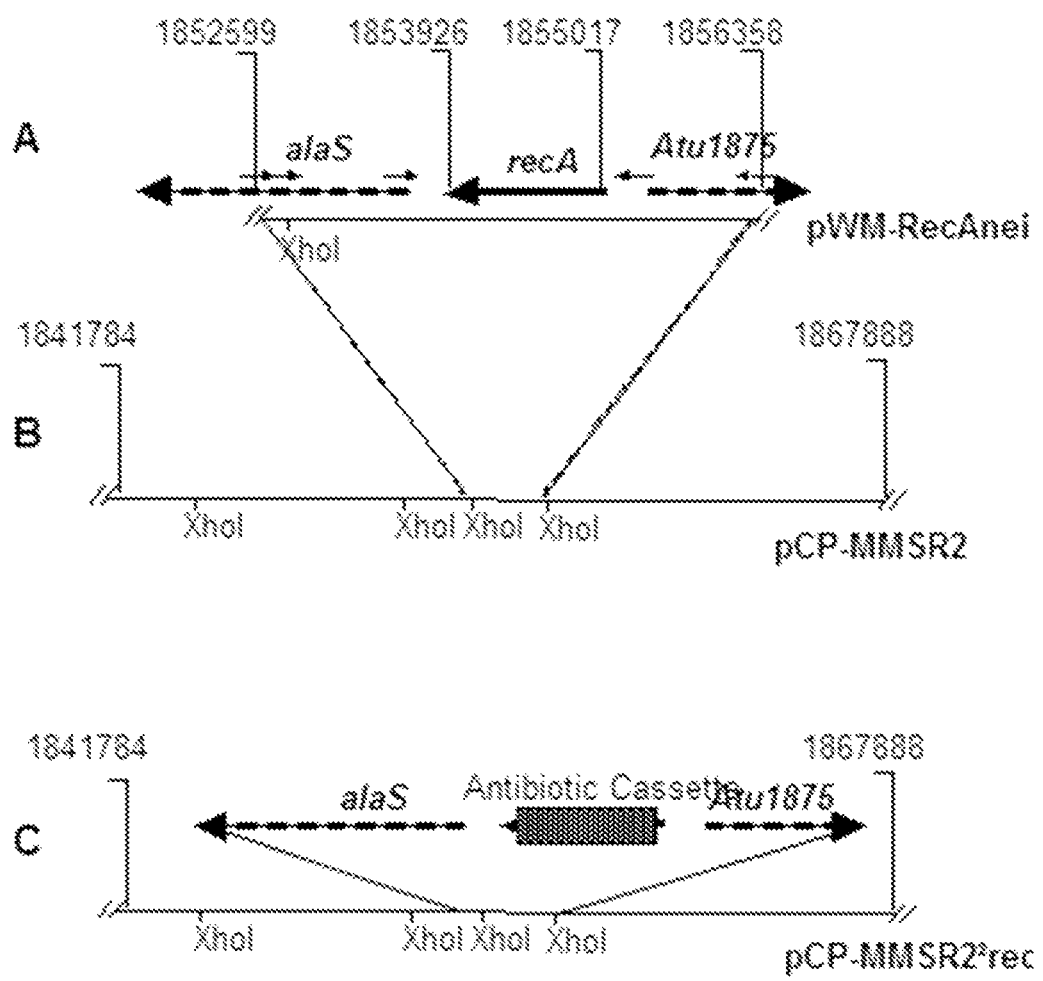
FIG. 1 illustrates an insert fragment maps of plasmids used for recA mutagenesis.

Disclosed herein are novel compositions and methods for the production and use of *Agrobacterium tumefaciens* (LBA4404) strains that are deficient in RecA activity relative to the parent strain. Further described is a chromosomal integration site for the integration of a polynucleotide fragment within the genome of *Agrobacterium tumefaciens* (LBA4404). The disclosed novel compositions and methods are useful for the production of transgenic events with plant species.

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application are specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, "endogenous sequence" defines the native form of a polynucleotide, gene or polypeptide in its natural location in the organism or in the genome of an organism.

As used herein, the terms "polynucleotide," "nucleic acid," and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide," and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a hetereologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another gene or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

As used herein, the term "modification" can refer to a change in a polynucleotide disclosed herein that results in reduced, substantially eliminated or eliminated activity of a polypeptide encoded by the polynucleotide, as well as a change in a polypeptide disclosed herein that results in reduced, substantially eliminated or eliminated activity of the polypeptide. Alternatively, the term "modification" can refer to a change in a polynucleotide disclosed herein that results in increased or enhanced activity of a polypeptide encoded by the polynucleotide, as well as a change in a polypeptide disclosed herein that results in increased or enhanced activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified, can be found by comparing the sequence of the particular polynucleotide or polypeptide with that of homologous polynucleotides or polypeptides, e.g., yeast or bacterial, and maximizing the number of modifications made in regions of high homology (conserved regions) or consensus sequences.

The term "derivative", as used herein, refers to a modification of a sequence set forth in the present disclosure. Illustrative of such modifications would be the substitution, insertion, and/or deletion of one or more bases relating to a nucleic acid sequence of a coding sequence disclosed herein that preserve, slightly alter, or increase the function of a coding sequence disclosed herein in crop species. Such derivatives can be readily determined by one skilled in the art, for example, using computer modeling techniques for predicting and optimizing sequence structure. The term "derivative" thus also includes nucleic acid sequences having substantial sequence identity with the disclosed coding sequences herein such that they are able to have the disclosed functionalities for use in producing embodiments of the present disclosure.

The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise rationally designed DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

The term "expression," as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic," "recombinant," or "transformed" organisms.

As used herein, the term "binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The terms "plasmid" and "vector," as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may carry DNA derived from essentially any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences for propagation in bacterial hosts.

Polypeptide and "protein" are used interchangeably herein and include a molecular chain of two or more amino acids linked through peptide bonds. The terms do not refer to a specific length of the product. Thus, "peptides", and "oligopeptides", are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be synthesized, or expressed recombinantly using known protein engineering techniques. In addition, inventive fusion proteins can be derivatized as described herein by well-known organic chemistry techniques.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

Expression "control sequences" refers collectively to promoter sequences, ribosome binding sites, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 Overview of principles of hybridization and the strategy of nucleic acid probe assays, Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The disclosure also relates to an isolated polynucleotide hybridizable under stringent conditions, preferably under highly stringent conditions, to a polynucleotide as of the present disclosure.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the disclosure is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in this application or the complement thereof.

Another non-limiting example of stringent hybridization conditions are hybridization in 6× sodium chloride/sodium citrate (SSC) at about 45° C., followed by one or more washes in 1×SSC, 0.1% SDS at 50° C., preferably at 55° C. more preferably at 60° C. and even more preferably at 65° C.

Highly stringent conditions can include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

In some embodiments an isolated nucleic acid molecule of the disclosure that hybridizes under highly stringent conditions to a nucleotide sequence of the disclosure can correspond to a naturally-occurring nucleic acid molecule. As used herein, a "naturally-occurring" nucleic acid molecule refers to an RNA or DNA molecule having a nucleotide sequence that occurs in nature (e.g., encodes a natural protein).

A skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). The terms "homology" or "percent identity" are used interchangeably herein. For the purpose of this disclosure, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available on the internet at the accelrys world wide web accelrys.com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available on the internet at the accelrys world wide web accelrys.com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available on the internet at the vega website, more specifically ALIGN-IGH Montpellier, or more specifically at http://vega.igh.cnrs.fr/bin/align-guess.cgi) using a PAM120 weight residue table, a gap length penalty of 12 and a gap penalty of 4.

The nucleic acid and protein sequences of the present disclosure may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present disclosure. BLAST protein searches may be performed with the BLASTX program, score=50, word length=3 to obtain amino acid sequences homologous to the protein molecules of the present disclosure. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. (Available on the internet at the ncbi website for example world wide web ncbi.nlm.nih.gov).

The term "chimeric" as used herein, means comprised of sequences that are "recombined". For example the sequences are "recombined and are not found together in nature.

The term "recombine" as used herein means refers to any method of joining polynucleotides. The term includes end to end joining, and insertion of one sequence into another. The term is intended to encompass includes physical joining techniques such as sticky-end ligation and blunt-end ligation. Such sequences may also be artificially or recombinantly synthesized to contain the recombined sequences.

Suitable plants for the subject invention can be selected from the group consisting of flowers, fruit, vegetables, nursery, turf and ornamental crops. In a further embodiment, the fruit is selected from the group consisting of almond, apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. In a further embodiment, the vegetable is selected from the group consisting of asparagus, beet (for example sugar beet and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (for example sweet pepper, bell pepper, and hot pepper), potato, pumpkin, sweet potato, snap bean, squash, and tomato. In another embodiment, the nursery plant or flower or flower part is selected from the group consisting of baby's breath, carnation, dahlia, daffodil, geranium, gerbera, lily, orchid, peony, Queen Anne's lace, rose, snapdragon, or other cut-flowers or ornamental flowers, potted flowers, flower bulbs, shrub, deciduous or coniferous tree.

Ti Plasmid—In some embodiments the *Agrobacterium tumefaciens* (LBA4404) deficient in RecA activity comprises a Ti plasmid. The Ti plasmid (also known as a helper plasmid) comprises the vir regions necessary for the production and transfer of the T-DNA region. The Ti plasmids (e.g., pAL4404, pTiBo542, pTiC58 [and the common derivative pTi15955], pTiAch5, or a pTiChry5) include, among other gene features, octopine synthesizing genes, oncogenes, virulent genes (herein after vir genes), and imperfect repeat T-DNA border sequences which flank the T-strand. Most Ti plasmids that are used in *Agrobacterium* strains for plant transformation are disarmed. Accordingly, the vir and one gene regions that are located within the T-strand of wildtype, virulent *Agrobacterium* strains have been removed or mutated. However, the T-DNA borders remain, and are modified to include a polynucleotide sequence between the right and left T-DNA borders. A disarmed Ti plasmid is still capable of transforming a T-strand within plant genomic DNA, but the T-strand is modified to reduce or remove oncogenic properties that are found in a wild type and virulent T-strand. In an embodiment, a wildtype and virulent Ti plasmid that has been modified to rearrange, mutate, delete, add, invert, or translocate a polynucleotide sequence are referred herein as a Ti plasmid derivative. In an embodiment, the T-DNA region has been modified to contain at least one gene expression cassette expressing an agronomic trait. Such Ti-derived plasmids, having functional vir genes and lacking all or substantially all of the T-region and associated elements are provided herein as an embodiment.

In subsequent embodiments, the Ti plasmid is a pTiBo542 plasmid. In an embodiment, the Ti plasmid is a derivative of a pTiBo542 plasmid (Hood, E. E.; Helmer, G. C.; Fraley, R. T.; Chilton, M. D. The hypovirulence of *Agrobacterium tumefaciens* A281 is encoded in the region of PtiB0542 outside the T-DNA. J. Bacteriol. 168:1291-1301; 1986, herein incorporated by reference in its entirety. In subsequent embodiments, the Ti plasmid is a pTiC58 plasmid (Holsters et al., The Functional Organization of the Nopaline *A. tumefaciens* plasmid pTiC58. Plasmid 3(2); 212-230, 1980, herein incorporated by reference in its entirety). In an embodiment, the Ti plasmid is a derivative of a pTiC58 plasmid. In subsequent embodiments, the Ti plasmid is a pTiAch5 plasmid (Gielen, J.; De Beuckeleer, M.; Seurinck, J.; Deboeck F.; De Greve H.; Lemmers, M.; Van Montagu M.; Schell J. The Complete Nucleotide Sequence of the TL-DNA of the *Agrobacterium tumefaciens* plasmid pTiAch5. The EMBO Journal. 3(4):835-846; 1984, herein incorporated by reference in its entirety). In an embodiment, the Ti plasmid is a derivative of a pTiAch5 plasmid. In subsequent embodiments, the Ti plasmid is a pTiChry5 plasmid (Kovacs L. G.; Pueppke S. G. Mapping and Genetic Organization of pTiChry5, a Novel Ti Plasmid from a Highly Virulent *Agrobacterium tumefaciens* Strain, Mol Gen Genet 242(3):327-336, 1994, herein incorporated by reference in its entirety). In an embodiment, the Ti plasmid is a derivative of a pTiChry5 plasmid. In subsequent embodiments, the Ti plasmid is a pTi15995 plasmid (Barker, R. F., Idler, K. B., Thompson, D. V. and Kemp, J. D. Nucleotide sequence of the T-DNA region from the *Agrobacterium tumefaciens* octopine Ti plasmid pTi15955, Plant Mol. Biol. 2 (6), 335-350, 1983, herein incorporated by reference in its entirety). In an embodiment, the Ti plasmid is a derivative of a pTi15995 plasmid. In further embodiments, the Ti plasmid is a derivative of a pAL4404 plasmid (van der Fits et al., (2000) Plant Molec. Biol. 43:495-502, herein incorporated by reference in its entirety).

Binary Vector—In some embodiments the *Agrobacterium tumefaciens* (LBA4404) deficient in RecA activity comprises a binary vector. In other embodiments the second plasmid is a binary vector. Non-limiting examples of binary vectors include; pBIN binary vector (Bevan M (1984) Binary *Agrobacterium* vectors for plant transformation. Nucleic Acids Res 12: 8711-872, herein incorporated by reference in its entirety), pGA binary vector (An G (1987) Binary Ti vectors for plant transformation and promoter analysis. Methods Enzymol 153: 292-305 An G, Watson B D, Stachel S, Gordon M P, Nester E W (1985) New cloning vehicles for transformation of higher plants. EMBO J 4: 277-284, herein incorporated by reference in its entirety), SEV binary vector (Fraley R T, Rogers S G, Horsch R B, Eichholtz D A, Flick J S, Fink C L, Hoffmann N L, Sanders P R (1985) The SEV system: a new disarmed Ti plasmid vector system for plant transformation. Biotechnology (N Y) 3: 629-635, herein incorporated by reference in its entirety), pEND4K binary vector (Klee H J, Yanofsky M F, Nester E W (1985) Vectors for transformation of higher plants. Biotechnology (N Y) 3: 637-642, herein incorporated by reference in its entirety), pBI binary vector (Jefferson R A, Kavanagh T A, BevanMW (1987) GUS fusions: b-glucuronidase as a sensitive and versatile gene fusion marker in higher plants. EMBO J 6:3901-3907, herein incorporated by reference in its entirety), pCIB10 binary vector (Rothstein S J, Lahners K N, Lotstein R J, Carozzi N B, Jayne S M, Rice D A (1987) Promoter cassettes, antibiotic-resistance genes, and vectors for plant transformation. Gene 53: 153-161, herein incorporated by reference in its entirety), pMRK63 binary vector (Vilaine F, Casse-Delbart F (1987) A new vector derived from *Agrobacterium* rhizogenes plasmids: a micro-Ri plasmid and its use to construct a mini-Ri plasmid. Gene 55: 105-114, herein incorporated by reference in its entirety), pGPTV binary vector (Becker D (1990) Binary vectors which allow the exchange of plant selectable markers and reporter genes. Nucleic Acids Res 18: 203, herein incorporated by reference in its entirety), pCGN1547 binary vector (McBride K E, Summerfelt K R (1990) Improved binary vectors for *Agrobacterium*-mediated plant transformation. Plant Mol Biol 14: 269-276, herein incorporated by reference in its entirety), pART binary vector (Gleave A P (1992) A versatile binary vector system with a T-DNA organizational structure conducive to efficient integration of cloned DNA into the plant genome. Plant Mol Biol 20: 1203-1207, herein incorporated by reference in its entirety), pGKB5 binary vector (Bouchez D, Camilleri C, Caboche M (1993) A binary vector based on Basta resistance for in planta transformation of *Arabidopsis thaliana*. C R Acad Sci Ser III Sci Vie 316: 1188-1193, herein incorporated by reference in its entirety), pMJD80 binary vector (Day M J D, Ashurst J L, Dixon R A (1994) Plant expression cassettes forenhanced translational efficiency. Plant Mol Biol Rep 12: 347-357, herein incorporated by reference in its entirety), pMJD81 binary vector (Day M J D, Ashurst J L, Dixon R A (1994) Plant expression cassettes forenhanced translational efficiency. Plant Mol Biol Rep 12: 347-357, herein incorporated by reference in its entirety), pPZP binary vector (Hajdukiewicz P, Svab Z, Maliga P (1994) The small, versatile pPZP family of *Agrobacterium* binary vectors for plant transformation. Plant Mol Biol 25: 989-994, herein incorporated by reference in its entirety), pBINPLUS binary vector (van Engelen F A, Molthoff J W, Conner A J, Nap J P, Pereira A, Stiekema W J (1995) pBINPLUS: an improved plant transformation vector based on pBIN19. Transgenic Res 4: 288-290, herein incorporated by reference in its entirety), pRT100 binary vector (Uberlacker B, Wen W (1996) Vectors with rare-cutter restriction enzyme sites for expression of open reading frames in transgenic plants. Mol Breed 2: 293-295, herein incorporated by reference in its entirety), pCB binary vector (Xiang C, Han P, Lutziger I, Wang K, Oliver D J (1999) A mini binary vector series for plant transformation. Plant Mol Biol 40: 711-717, herein incorporated by reference in its entirety), pGreen binary vector (Hellens R P, Edwards E A, Leyland N R, Bean S, Mullineaux P M (2000) pGreen: a versatile and flexible binary Ti vector for Agrobacteriummediated plant transformation. Plant Mol Biol 42: 819-832, herein incorporated by reference in its entirety), pPZP-RCS2 binary vector (Goderis I J W M, De Bolle M F C, Francois I E J A, Wouters P F J, Broekaert W F, Cammue B P A (2002) A set of modular plant transformation vectors allowing flexible insertion of up to six expression units. Plant Mol Biol 50: 17-27, herein incorporated by reference in its entirety), pMDC binary vector (Curtis M D, Grossniklaus U (2003) A gateway cloning vector set for highthroughput functional analysis of genes in planta. Plant Physiol 133: 462-469, herein incorporated by reference in its entirety), pRCS2 binary vector (Chung S M, Frankman E L, Tzfira T (2005) A versatile vector system for multiple gene expression in plants. Trends Plant Sci 10: 357-361, herein incorporated by reference in its entirety), pEarleyGate binary vector (Earley K W, Haag J R, Pontes O, Opper K, Juehne T, Song K, Pikaard C S (2006) Gateway-compatible vectors for plant functional genomics and proteomics. Plant J 45: 616-629, herein incorporated by reference in its entirety), pGWTAC binary vector (Chen Q J, Zhou H M, Chen J, Wang X C (2006) A Gateway-based platform for multigene plant transformation. Plant Mol Biol 62: 927-936, herein incorporated by reference in its entirety), pORE binary vector (Coutu C, Brandle J, Brown D, Brown K, Miki B, Simmonds J, Hegedus D D (2007) pORE: A modular binary vector series suited for both monocot and dicot plant transformation. Transgenic Res 16: 771-781, herein incorporated by reference in its entirety), pSITE binary vector (Chakrabarty R, Banerjee R, Chung S M, Farman M, Citovsky V, Hogenhout S A, Tzfira T, Goodin M (2007) pSITE vectors for stable integration or transient expression of autofluorescent protein fusions in plants: probing Nicotiana benthamiana-virus interactions. Mol Plant Microbe Interact 20: 740-750, herein incorporated by reference in its entirety), pMSP binary vector (Lee L Y, Kononov M E, Bassuner B, Frame B R, Wang K, Gelvin S B (2007) Novel plant transformation vectors containing the superpromoter. Plant Physiol 145: 1294-1300, herein incorporated by reference in its entirety), pCAMBIA binary vector (http://www.cambia.org/daisy/cambia/materials/vectors), and pGD binary vector (Goodin M M, Dietzgen R G, Schichnes D, Ruzin S, Jackson A O (2002) pGD vectors: versatile tools for the expression of green and red fluorescent protein fusions in agroinfiltrated plant leaves. Plant J 31: 375-383, herein incorporated by reference in its entirety). See, herein incorporated by reference in its entirety. Binary vectors generally contain a number of important features such as T-DNA border sequences, origins of replication that are functional in both *Escherichia coli* and *Agrobacterium* strains, antibiotic resistance genes that are compatible with other antibiotic resistance harbored by the pTi/pRi plasmid and/or *Agrobacterium* genome, and other features that improve plant transformation efficiency (e.g., overdrive sequence). Further features of binary vectors are known to those having ordinary skill in the art, for example see, Lee and Gelvin (2008) *Plant Physiology,* 146; 325-332 (herein incorporated by reference) which discloses many of the above described features of binary plasmids/vectors.

Ternary Vector—In some embodiments the *Agrobacterium tumefaciens* (LBA4404) deficient in RecA activity comprises a ternary vector. A "ternary" (i.e., three-plasmid) vector wherein a copy of the constitutive mutant virGN54D gene from pTi15955 is co-resident on a pBBR1-derived plasmid in *Agrobacterium tumefaciens* strain LBA4404 that contained the disarmed Ti helper plasmid pAL4404 and a binary vector harboring genes for plant transformation has been described. See van der Fits et al., (2000) Plant Molec. Biol. 43:495-502, herein incorporated by reference in its entirety. Additional non-limiting examples of a ternary vector are described in further detail at European Patent Application No. 2042602A1 and U.S. Patent Application No. 2010/0132068A1 that describe cosmid binary vectors and "booster" plasmids that, when present in an *Agrobacterium* cell harboring a Ti helper plasmid, constitute further examples of ternary plasmid systems, herein incorporated by reference in its entirety. Finally, International Patent Application No. 2012016222A2 describes a ternary plasmid system for use in *Agrobacterium*, herein incorporated by reference in its entirety.

Plasmids—In some embodiments a plasmid comprising a recA gene is an embodiment of the subject disclosure. Plasmids are assigned to incompatibility groups (genotypic designation: inc; group designation: Inc) based on sequences contained in the plasmid. The inc determinant typically serves to prevent other plasmids of the same or related incompatibility group from coexisting in the same host, and helps maintain a certain copy number of the plasmid within the cell. See, e.g., Fernandez-Lopez, et al. (2006) *FEMS Microbiol. Rev.* 30:942-66; and Adamczyk and Jagura-Burdzy (2003) *Acta Biochim. Pol.* 50:425-53. Two plasmids are incompatible if either is less stable in the presence of the other than it is by itself. Competition for cell resources can result when two plasmids of the same incompatibility group are found in the same cell. Whichever plasmid is able to replicate faster, or provides some other advantage, will be represented to a disproportionate degree among the copies allowed by the incompatibility system. Surprisingly, plasmids can also be incompatible when they both possess the same functions for partitioning themselves into daughter cells.

Plasmids typically fall into only one of the many existing incompatibility groups. There are more than 30 known incompatibility groups. Plasmids belonging to incompatibility group IncP have been studied thoroughly and a large number of plasmids which derive from this IncP group have been constructed (Schmidhauser et al. (1988) *Biotechnology* 10:287-332). Exemplary plasmids containing the IncP incompatibility group include: pMP90RK, pRK2013, pRK290, pRK404, and pRK415. These plasmids may be maintained in numerous bacterial species including *E. coli* and *Agrobacterium tumefaciens*. Examples of other incompatibility groups include, but are not limited to; IncN, IncW, IncL/M, IncT, IncU, IncW, IncY, IncB/O, IncFII, Inch, IncK, IncCom9, IncFI, IncFII, IncFIII, IncHI1, IncHI2, IncX, IncA/C, IncD, IncFIV, IncFV/FO, IncFVI, IncH1 3, IncHI1, Inc12, IncI, IncJ, IncV, IncQ, and the like, including variants thereof, e.g., exhibiting substantial sequence or functional relationship.

In addition, a suitable plasmid used to transform plant cell using the methods described herein can contain a selectable marker gene encoding a protein that confers on the transformed plant cells resistance to an antibiotic or a herbicide. The individually employed selectable marker gene may accordingly permit the selection of transformed cells while the growth of cells that do not contain the inserted DNA can be suppressed by the selective compound. The particular selectable marker gene(s) used may depend on experimental design or preference, but any of the following selectable markers may be used, as well as any other gene not listed herein that could function as a selectable marker. Examples of selectable markers include, but are not limited to, genes that provide resistance or tolerance to antibiotics such as kanamycin, G418, hygromycin, bleomycin, and methotrexate, or to herbicides, such as phosphinothricin (bialaphos), glyphosate, imidazolinones, sulfonylureas, triazolopyrimidines, chlorsulfuron, bromoxynil, and Dalapon.

Gene Expression Cassettes Encoding Agronomic Traits—
In subsequent embodiments, the plant cells are selected to regenerate plants from said cells. In further embodiments of the disclosure, the T-DNA contains a gene expression cassette that encodes an agronomic trait. In additional embodiments, the agronomic trait produces a commodity product.

In an embodiment, the subject disclosure relates to the introduction of one or more gene expression cassettes which are inserted within the plant genome. In some embodiments the gene expression cassettes comprise a coding sequence. The coding sequence can encode, for example, a gene that confers an agronomic trait. In further embodiments, the agronomic trait is selected from the group consisting of an insecticidal resistance trait, herbicide tolerance trait, nitrogen use efficiency trait, water use efficiency trait, nutritional quality trait, DNA binding trait, and selectable marker trait. In additional embodiments, the agronomic traits are expressed within the plant. An embodiment of the subject disclosure includes a plant comprising one or more agronomic traits.

In some embodiments the transgenic plant comprises a gene expression cassette. Standard recombinant DNA and molecular cloning techniques for the construction of a gene expression cassette as used herein are well known in the art and are described, e.g., by Sambrook et al., *Molecular Cloning: A Laboratory Manual*, Second Edition, Cold Spring Harbor Laboratory Press, Cold Spring Harbor, N.Y. (1989); and by Silhavy et al., *Experiments with Gene Fusions*, Cold Spring Harbor Laboratory Press, Cold Spring Harbor, N.Y. (1984); and by Ausubel et al., *Current Protocols in Molecular Biology*, published by Greene Publishing Assoc. and Wiley-Interscience (1987).

A number of promoters that direct expression of a gene in a plant can be employed in a gene expression cassette. Such promoters can be selected from constitutive, chemically-regulated, inducible, tissue-specific, and seed-preferred promoters. The promoter used to direct expression of a nucleic acid depends on the particular application. For example, a strong constitutive promoter suited to the host cell is typically used for expression and purification of expressed proteins.

Non-limiting examples of preferred plant promoters include promoter sequences derived from *A. thaliana* ubiquitin-10 (ubi-10) (Callis, et al., 1990, *J. Biol. Chem.*, 265: 12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139). Other constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) *Plant Mol. Biol.* 18:675-689); pEMU promoter (Last et al. (1991) Theor. Appl. Genet. 81:581-588); ALS promoter (U.S. Pat. No. 5,659,026); Maize Histone promoter (Chabouté et al. Plant Molecular Biology, 8:179-191 (1987)); and the like.

Other useful plant promoters include tissue specific and inducible promoters. An inducible promoter is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the embodiments of the instant disclosure. See Ward et al., Plant Mol. Biol. 22: 361-366 (1993). Exemplary inducible promoters include ecdysone receptor promoters (U.S. Pat. No. 6,504,082); promoters from the ACE1 system which respond to copper (Mett et al., Proc. Natl. Acad. Sci. 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); or promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-1a promoter, which is activated by salicylic acid (see Ono S, Kusama M, Ogura R, Hiratsuka K., "Evaluation of the Use of the Tobacco PR-1a Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al., (1997) Plant J. 12(2): 255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as P5CS (Zang et al., (1997) Plant Sciences 129:81-89); cold-inducible promoters, such as, corl5a (Hajela et al., (1990) Plant Physiol. 93:1246-1252), corl5b (Wilhelm et al., (1993) Plant Mol Biol 23:1073-1077), wscl (Ouellet et al., (1998) FEBS Lett. 423-324-328), ci7 (Kirch et al., (1997) Plant Mol Biol. 33:897-909), ci21A (Schneider et al., (1997) Plant Physiol. 113:335-45); drought-inducible promoters, such as Trg-31 (Chaudhary et al., (1996) Plant Mol. Biol. 30:1247-57), rd29 (Kasuga et al., (1999) Nature Biotechnology 18:287-291); osmotic inducible promoters, such as Rab17 (Vilardell et al., (1991) Plant Mol. Biol. 17:985-93) and osmotin (Raghothama et al., (1993) Plant Mol Biol 23:1117-28); and heat inducible promoters, such as heat shock proteins (Barros et al., (1992) Plant Mol. 19:665-75; Marrs et al., (1993) Dev. Genet. 14:27-41), smHSP (Waters et al., (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al., (1993) Mol. Gen. Genetics 236:331-340). Certain promoters are inducible by wounding, including the *Agrobacterium* pMAS promoter (Guevara-Garcia et al., (1993) Plant J. 4(3):495-505) and the *Agrobacterium* ORF13 promoter (Hansen et al., (1997) Mol. Gen. Genet. 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al., (1989) *The Plant Cell* Vol. 1, 839-853), and the maize globulin-1 gene (Belanger, et al. (1991) *Genetics* 129:863-972). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al., (1994) T-DNA tagging of a seed coat-specific cryptic promoter in tobacco. Plant J. 4: 567-577), the P-gene promoter from maize (Chopra et al., (1996) Alleles of the maize P gene with distinct tissue specificities encode Myb-homologous proteins with C-terminal replacements. Plant Cell 7:1149-1158, Erratum in Plant Cell. 1997, 1:109), the globulin-1 promoter from maize (Belenger and Kriz (1991) Molecular basis for Allelic Polymorphism of the maize Globulin-1 gene. Genetics 129: 863-972), and promoters that direct expression to the seed coat or hull of maize kernels, for example the pericarp-specific glutamine synthetase promoter (Muhitch et al., (2002) Isolation of a Promoter Sequence From the Glutamine Synthetase$_{1-2}$ Gene Capable of Conferring Tissue-Specific Gene Expression in Transgenic Maize. Plant Science 163:865-872).

In addition to the promoter, the gene expression cassette (which can be in, e.g., a vector) typically contains a transcription unit or expression cassette that contains all the additional elements required for the expression of the nucleic acid in host cells, either prokaryotic or eukaryotic. A typical expression cassette thus contains a promoter operably linked to a nucleic acid sequence encoding a gene product (e.g., a protein). The gene expression cassette may also include additional elements which are operably linked according to methods known art: signals required for efficient polyadenylation of the transcript, transcriptional termination, ribosome binding sites, or translation termination. Additionally, the expression cassette may include enhancers and/or heterologous splicing signals.

Other components of the gene expression cassette are provided as embodiments. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, (1997) *Plant Mol. Biol.*, 34: 687-692 and International Patent Publication No. WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al eds; CRC Press pp. 89-119 (1993). The selection of an appropriate expression vector will depend upon the host and the method of introducing the expression vector into the host. The gene expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp 7831-7846(nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. *Gene* 91:151-158 (1990); Ballas et al., Nucleic Acids Res. 17:7891-7903 (1989); Joshi et al. Nucleic Acid Res. 15:9627-9639 (1987).

The gene expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al., Proc. Nat. Acad. Sci. USA 86:6126-6130 (1989);

potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al., Nature 353:90-94 (1991); untranslated leader from the coat protein mRNA of alfalfa mosaic virus (AMV RNA 4), Jobling et al., Nature 325:622-625 (1987); Tobacco mosaic virus leader (TMV), Gallie et al., (1989) Molecular Biology of RNA, pages 237-256; and maize chlorotic mottle virus leader (MCMV) Lommel et al., Virology 81:382-385 (1991). See also Della-Cioppa et al., Plant Physiology 84:965-968 (1987).

The gene expression cassette construct can also contain sequences that enhance translation and/or mRNA stability such as introns. An example of one such intron is the first intron of gene II of the histone H3.III variant of *Arabidopsis thaliana*. Chaubet et al., Journal of Molecular Biology, 225:569-574 (1992).

In those instances where it is desirable for the expression cassette to express a gene product that is directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (U.S. Pat. No. 5,510,417), *Zea mays* Brittle-1 chloroplast transit peptide (Nelson et al., Plant Physiol 117(4):1235-1252 (1998); Sullivan et al., Plant Cell 3(12):1337-48; Sullivan et al., Planta (1995) 196(3):477-84; Sullivan et al., J. Biol. Chem. (1992) 267(26):18999-9004) and the like. In addition, chimeric chloroplast transit peptides are known in the art, such as the Optimized Transit Peptide (U.S. Pat. No. 5,510,471). Additional chloroplast transit peptides have been described previously in U.S. Pat. Nos. 5,717,084 and 5,728,925. One skilled in the art will readily appreciate the many options available in expressing a product to a particular organelle. For example, the barley alpha amylase sequence is often used to direct expression to the endoplasmic reticulum (Rogers, J. Biol. Chem. 260: 3731-3738 (1985)).

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants can be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, (1983); Meijer et al., Plant Mol. Biol. 16:807-820, (1991)); neomycin phosphotransferase, which confers resistance to the aminoglycosides neomycin, kanamycin and paromycin (Herrera-Estrella, EMBO J. 2:987-995, 1983 and Fraley et al., Proc. Natl. Acad. Sci USA 80:4803 (1983)) and hygromycin phosphotransferase, which confers resistance to hygromycin (Marsh, Gene 32:481-485, (1984); see also Waldron et al., Plant Mol. Biol. 5:103-108, (1985); Zhijian et al., Plant Science 108:219-227, (1995)); trpB, which allows cells to utilize indole in place of tryptophan; hisD, which allows cells to utilize histinol in place of histidine (Hartman, Proc. Natl. Acad. Sci., USA 85:8047, (1988)); mannose-6-phosphate isomerase which allows cells to utilize mannose (International Patent Application No. WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, Biosci. Biotechnol. Biochem. 59:2336-2338, (1995)).

Additional selectable markers include, for example, a mutant acetolactate synthase, which confers imidazolinone or sulfonylurea resistance (Lee et al., EMBO J. 7:1241-1248, (1988)), a mutant psbA, which confers resistance to atrazine (Smeda et al., Plant Physiol. 103:911-917, (1993)), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, (1983)); streptomycin (Jones et al., Mol. Gen. Genet. 210:86-91, (1987)); spectinomycin (Bretagne-Sagnard et al., Transgenic Res. 5:131-137, (1996)); bleomycin (Hille et al., Plant Mol. Biol. 7:171-176, (1990)); sulfonamide (Guerineau et al., Plant Mol. Biol. 15:127-136, (1990)); bromoxynil (Stalker et al., Science 242:419-423, (1988)); glyphosate (Shaw et al., Science 233:478-481, (1986)); phosphinothricin (DeBlock et al., EMBO J. 6:2513-2518, (1987)), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) Gene 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al., Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Scheffler et al., Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al., Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., *Genetics* (1988) 119:185-197; Nash et al., Plant Cell (1990) 2(11): 1039-1049), among others.

Further examples of suitable markers include the cyan fluorescent protein (CYP) gene (Bolte et al., (2004) J. Cell Science 117: 943-54 and Kato et al., (2002) Plant Physiol 129: 913-42), the yellow fluorescent protein gene (PHI-YFP™ from Evrogen; see Bolte et al., (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al., (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

In certain embodiments, the nucleotide sequence of the transgene encoding a gene product in an expression cassette can be optionally combined with another nucleotide sequence of interest in the cassette and/or the plant. For example, in certain embodiments the transgene can be combined or "stacked" with another nucleotide sequence of interest that provides additional resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The "stacking" of two or more nucleic acid sequences of interest within a plant genome can be accomplished, for example, via conventional plant breeding using two or more events, transformation of a plant with a construct which contains the sequences of interest, re-transformation of a transgenic plant, or addition of new traits through integration via homologous recombination.

Such nucleotide sequences of interest include, but are not limited to, those examples of genes or coding sequences that confer (1) resistance to pests or disease, (2) resistance to herbicides, and (3) value added traits provided below:

1. Genes or Coding Sequences (e.g. iRNA) That Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., 1993 *Science* 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al., (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, (1992) Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., (1993) Insect Molec. Biol. 23:691), and parsley ubi4-2 polyubiquitin gene (Kawalleck et al., (1993) Plant Molec. Biol. 21:673).

(K) A molecule that stimulates signal transduction. Examples of such molecules include nucleotide sequences for mung bean calmodulin cDNA clones (Botella et al., (1994) Plant Molec. Biol. 24:757) and a nucleotide sequence of a maize calmodulin cDNA clone (Griess et al., (1994) Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., (1993) Plant Sci. 89:43) which renders transgenic tobacco plants resistant to *Pseudomonas solanacearum.*

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al., (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al., (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al., (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., (1992) Bio/Technology 10:1436). The cloning and characterization of a gene which encodes a bean endopolygalacturonase-inhibiting protein is described by (Toubart et al., (1992) Plant J. 2:367).

(R) A developmental-arrestive protein produced in nature by a plant, such as the barley ribosome-inactivating gene that provides an increased resistance to fungal disease (Longemann et al., (1992). Bio/Technology 10:3305).

(S) RNA interference, in which a DNA polynucleotide encoding an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al., U.S. Pat. No. 6,573,099.

2. Genes or Coding Sequences that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., (1988) EMBO J. 7:1241), which is also known as AHAS enzyme (Miki et al., (1990) Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European Patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricin acetyl-transferase gene is provided in European Patent application No. 0 242 246. De Greef et al., (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al., (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al., (1991) Plant Cell 3:169 describe the use of plasmids encoding mutant psbA genes to transform *Chlamydomonas.* Nucleotide sequences for nitrilase genes in U.S. Pat. No. 4,810,648, and DNA molecules containing these genes are available under ATCC accession numbers 53435, 67441 and 67442. Cloning and expression of DNA coding for a glutathione S-transferase is described by Hayes et al., (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (European Patent No. 418175, European Patent No. 470856, European Patent No. 487352, European Patent No. 527036, European Patent No. 560482, European Patent No. 682659, U.S. Pat. No. 5,424,276), in particular isoxaflutole, which is a selective herbicide for maize, diketonitriles (European Patent No. 496630, and European Patent No. 496631), in particular 2-cyano-3-cyclopropyl-1-(2-SO2CH3-4-CF3 phenyl) propane-1,3-dione and 2-cyano-3-cyclopropyl-1-(2-SO2CH3-4-2,3Cl2phenyl) propane-1,3-dione, triketones (European Patent No. 625505, European Patent No. 625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., (1992) Proc. Nat. Acad. Sci. USA 89:2624.

(B) Decreased phytate content.

(1) Introduction of a phytase-encoding gene, such as the *Aspergillus niger* phytase gene (Van Hartingsveldt et al., (1993) Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., (1990) Maydica 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., (1988) J. Bacteriol. 170: 810), *Bacillus subtilis* levansucrase gene (Steinmetz et al., (1985) Mol. Gen. Genel. 200:220), *Bacillus licheniformis* α-amylase (Pen et al., (1992) Bio/Technology 10:292), tomato invertase genes (Elliot et al., (1993), barley amylase gene (Sogaard et al., (1993) J. Biol. Chem. 268:22480), and maize endosperm starch branching enzyme II (Fisher et al., (1993) Plant Physiol. 102:10450).

Commodity Products—In further embodiments of the subject disclosure, the transgenic plant produces a commodity product. In an embodiment, the commodity product is selected from the group consisting of protein concentrate, protein isolate, grain, meal, flour, oil, or fiber.

A commodity product refers to any product which is comprised of material derived from a plant or plant seed and is sold to consumers. Crop plants are the largest source of protein, carbohydrates and vegetable oil for consumption. The transgenic plants can be used to manufacture commodity products. The plants and/or plant seeds can be processed into meal, flour, or oil as well as be used as a protein or oil source in animal feeds for both terrestrial and aquatic animals. Soybeans and soybean oils can be used in the manufacture of many different products, but not limited to, whole or processed seeds, animal feed, vegetable oil, meal, flour, nontoxic plastics, printing inks, lubricants, waxes, hydraulic fluids, electric transformer fluids, solvents, cosmetics, hair care products, natto, tempeh, protein concentrate, protein isolates, textured and hydrolyzed protein, and biodiesel.

Plant Classification—In additional embodiments the subject disclosure relates to a transgenic plant, wherein the transgenic plant is selected from the group consisting of a dicotyledonous plant or a monocotyledonous plant. In further embodiments, the subject disclosure relates to consumable plants, including crop plants and plants used for their oils, protein, or carbohydrates. Thus, any plant species or plant cell can be selected as described further below.

In some embodiments, plants which are genetically modified in accordance with the present disclosure (e.g., plant host cells) includes, but is not limited to, any higher plants, including both dicotyledonous and monocotyledonous plants, and particularly consumable plants, including crop plants. Such plants can include, but are not limited to, for example: alfalfa, soybeans, cotton, rapeseed (also described as canola), linseed, corn, rice, brachiaria, wheat, safflowers, sorghum, sugarbeet, sunflowers, tobacco and turf grasses. Thus, any plant species or plant cell can be selected. In embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*; Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* and *Triticum aestivum*); and duckweed (*Lemnaceae* sp.). In some embodiments, the genetic background within a plant species may vary.

The nucleic acids introduced into a plant cell can be used to confer desired traits on essentially any plant. A wide variety of plants and plant cell systems may be engineered for the desired physiological and agronomic characteristics described herein using the gene expression constructs of the present disclosure and the various transformation methods mentioned above. In embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea mays.*

In further aspects of subject disclosure the systems, compositions, and methods disclosed herein relate to a transgenic plant or plant cell. In other embodiments, the transgenic plant or plant cell is produced by contacting plant cells with an *A. tumefaciens* (LBA4404) strain deficient in RecA activity.

In Vitro Assays—

In an embodiment, the subject disclosure relates to an in vitro assay for assessing RecA activity within the *A. tumefaciens* (LBA4404) strain. Various in vitro assays are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. in one embodiment, a second fluorescent DNA dye is SYTO13® used at less than 10 µM, less than 4 µM, or less than 2.7 µM.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generare sequencing reads. DNA fragments of 300-800 bp or libraries containing fragments of 3-20 kbp can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kbp in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotide that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In another embodiment, the detection can be completed using blotting assays, including Western blots, Northern blots, and Southern blots. Such blotting assays are commonly used techniques in biological research for the identification and quantification of biological samples. These assays include first separating the sample components in gels by electrophoretic means, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the detection can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Transformation—Transformation of the *A. tumefaciens* LBA (4404) host cells with the vector(s) disclosed herein may be performed using any transformation methodology known in the art, and the bacterial host cells may be transformed as intact cells or as protoplasts (i.e. including cytoplasts). Exemplary transformation methodologies include 'poration methodologies, e.g., electroporation, protoplast fusion, bacterial conjugation, and divalent cation treatment (calcium chloride $CaCl_2$ treatment or $CaCl_2/Mg^{2+}$ treatment), or other well known methods in the art. See, e.g., Morrison, *J. Bact.*, 132:349-351 (1977); Clark-Curtiss & Curtiss, *Methods in Enzymology*, 101:347-362 (Wu et al., eds, 1983), Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). Other known transformation methods specific are described at by Guerout-Fleury, A. M., Frandsen, N. and Stragier, P. (1996) Plasmids for ectopic integration in *Bacillus subtilis*. Gene 180 (1-2), 57-61.

Integration Site—Embodiments of the disclosure include methods for identifying and integrating a polynucleotide fragment within a genomic locus of *A. tumefaciens* (LBA4404). The integration within the recA genomic locus, or within the polynucleotide fragments directly upstream or downstream of the recA genomic locus is provided herein. The genomic locus for integrating the polynucleotide fragment is provided as SEQ ID NO: 11. Those having ordinary skill in the art will appreciate that allelic variation of a disclosed genomic polynucleotide sequence may be observed within SEQ ID NO: 11 of *A. tumefaciens* (LBA4404). Accordingly, the disclosure relates to a polynucleotide sequence with 80%, 82.5%, 85%, 87.5%, 90%, 92.5%, 95%, 97.5%, 99%, 99.5%, or 99.9% sequence identity with SEQ ID NO: 11.

Other embodiments of the present disclosure can include integrating a polynucleotide into the *A. tumefaciens* (LBA4404) genome at the recA genomic locus, and the subsequent stacking of a second polynucleotide at the same location. Wherein, the genomic locus within the *A. tumefaciens* (LBA4404) genome is utilized as a preferred locus for introducing additional polynucleotides. In an embodiment, any location within SEQ ID NO: 11 serves as a neutral integration site for the integration of a polynucleotide into the *A. tumefaciens* (LBA4404) genome.

Other embodiments of the present disclosure can include integrating a polynucleotide containing a gene expression cassette into the *A. tumefaciens* (LBA4404) genome at the recA genomic locus, and the subsequent removal of a selectable marker expression cassette from the integrated polynucleotide. Wherein, the method used to remove the selectable marker expression cassette is a double crossing over method, an excision method using CRE-LOX, an excision method using FLP-FRT, or an excision method using the RED/ET RECOMBINATION® kit (Genebridges, Heidelberg, Germany), in addition to other excision methods known in the art.

Other embodiments of the present disclosure can include integrating a polynucleotide into the *A. tumefaciens* (LBA4404) genome at the recA genomic locus as an alternative to the use of extraneous replicating plasmids. Wherein, one or more extraneous replicating plasmids are incompatible due to the presence of similar origins or replication, incompatibility groups, redundant selectable marker, or other gene elements. Wherein, one or more extraneous replicating plasmids are not functional in *A. tumefaciens* (LBA4404) due to the specificity of the *A. tumefaciens* (LBA4404) restriction modification system. Wherein, one or more extraneous replicating plasmids are not available, functional or readily transformable within the *A. tumefaciens* (LBA4404) genome.

Other embodiments of the present disclosure can include methods for increasing the efficiency of homologous recombination in a prokaryotic cell. Methods relying upon homologous recombination mediated by introduced enzymes, such as lambda red 'recombineering' and analogous approaches are useful in a limited number of bacterial classes, particularly *Escherichia* (Datsenko and Wanner (2000) Proc Natl Acad Sci USA. 97: 6640-5) and *Salmonella*. Methods relying upon site-specific recombination mediated by introduced enzymes, such as phage integrases, FLP/FRT or Cre/loxP may also be used, but are reliant on the presence of pre-existing sites within the target DNA (Wirth et al (2007) Current Opinions in Biotechnology 18, 411-419). Alternative methods exploit viruses or mobile elements, or their components (e.g. phage, transposons or mobile introns).

However, methods relying upon host-mediated homologous recombination are by far the most commonly-used type of chromosomal DNA modifications. In a typical microbial application of host-mediated homologous recombination, a plasmid with a single region of sequence identity with the chromosome is integrated into the chromosome by single-crossover integration, sometimes referred to as 'Campbell-like integration'. After such an event, genes on the introduced plasmid are replicated as part of the chromosome, which may be more rapid than the plasmid replication. Accordingly, growth in medium with selection for a plasmid-borne selectable marker gene may provide a selective pressure for integration. Campbell-like integration can be used to inactivate a chromosomal gene by placing an internal fragment of a gene of interest on the plasmid, so that after integration, the chromosome will not contain a full-length copy of the gene. The chromosome of a Campbell-like integrant cell is not stable, because the integrated plasmid is flanked by the homologous sequences that directed the integration. A further homologous recombination event between these sequences leads to excision of the plasmid, and reversion of the chromosome to wild-type. For this reason, it may be necessary to maintain selection for the plasmid-borne selectable marker gene to maintain the integrant clone.

An improvement on the basic single-crossover integration method of chromosomal modification is double crossover homologous recombination, also referred to as allelic exchange, which involves two recombination events. The desired modified allele is placed on a plasmid flanked by regions of homology to the regions flanking the target allele in the chromosome ('homology arms'). A first integration event can occur in either pair of homology arms, leading to integration of the plasmid into the chromosome in the same manner as Campbell-like integration. After the first crossover event, the chromosome contains two alternative sets of homologous sequences that can direct a second recombination event. If the same sequences that directed the first event recombine, the plasmid will be excised, and the cell will revert to wild-type. If the second recombination event is directed by the other homology arm, a plasmid will be excised, but the original chromosomal allele will have been exchanged for the modified allele introduced on the plasmid; the desired chromosomal modification will have been achieved. As with Campbell-like integration, the first recombination event is typically detected and integrants isolated using selective advantage conferred by integration of a plasmid-borne selectable marker gene.

Embodiments of the subject disclosure are further exemplified in the following Examples. It should be understood that these Examples are given by way of illustration only.

EXAMPLES

Example 1 Construction of an *Agrobacterium tumefaciens* (LBA4404) Genomic Library and Isolation of recA Plus Cosmid Clones A genomic DNA library is constructed to isolate and identify the previously uncharacterized recA gene from *Agrobacterium tumefaciens* (LBA4404). Genomic DNA from *A. tumefaciens* (LBA4404) is partially digested with the restriction enzyme Sau3A1 (New England Biolabs, Ipswich, Mass.), and is fractionated by centrifugation on a 10-40% discontinuous sucrose gradient in a buffer (20 mM Tris-HCl, pH 8.0; 10 mM EDTA; and, 50 mM NaCl). Fractions containing genomic DNA fragments with sizes spanning a range of about 20-40 kb are pooled and ligated into the broad-host-range cosmid vector, pCP13/B (tetracycline-resistant) (Dessaux Y, Tempé J, Farrand S K. 1987. Genetic analysis of mannityl opine catabolism in octopine-type *Agrobacterium tumefaciens* strain 15955. *Mol Gen Genet.* 208(1-2):301-8). This cosmid vector is treated with BamHI and alkaline phosphatase before use in the ligation reaction. The ligation mixture is processed using Promega's Packagene® Lambda DNA Packaging system (Promega, Madison, Wis.) and transfected into *Escherichia coli* (HB101). The resulting library bank contains about 5,000 tetracycline-resistant cosmid transductants representing about twenty-times the coverage of the *A. tumefaciens* (LBA4404) genome.

To isolate cosmid clones harboring the recA gene of *A. tumefaciens* (LBA4404), *E. coli* (HB101) bacterial strains are isolated from the library and spread onto Luria broth plates containing 0.01% methanesulfonic acid methyl ester (MMS). Because *E. coli* (HB101) is a recA mutant, and therefore sensitive to MMS, the MMS-resistant colonies that grew on the media are hypothesized to contain cosmids encoding the recA gene of *A. tumefaciens* (LBA4404) (Farrand S K, O'Morchoe S P, McCutchan J. 1989. Construction of an *Agrobacterium tumefaciens* C58 recA mutant. J Bacteriol. 171(10):5314-21). Hundreds of MMS-resistant cosmid clones are obtained, and twenty-four of them are further purified and analyzed by restriction enzyme digestion with XhoI. Nine of the colonies that shared a common subset of XhoI fragments are submitted for end sequencing using primers; pCP13/B left and pCP13/B right (Table 1). Assuming synteny between the chromosomes of *A. tumefaciens* (LBA4404), and the sequenced strain of *A. tumefaciens* (C58) the cosmids are searched for the junction sequences that predicted that recA would be located in the middle of the insert. One such cosmid, pCP-MMSR2, is subjected to further sequencing to confirm the presence of a putatively identified recA gene using primers as further described in Table 1.

TABLE 1

Primers used to identify and isolate the recA gene from *A. tumefaciens*

| Primers | Sequences |
|---|---|
| PCP13/B left (SEQ ID NO: 1) | GGCATTCTTGGCATAGTGGT |
| PCP13/B right (SEQ ID NO: 2) | GCTGAAGCCAGTTACCTTCG |
| F-RecAnei (SEQ ID NO: 3) | *CCGGATCCCCGCGTTCCAGCGTCTTGCGGA AACG |
| R-RecAnei (SEQ ID NO: 4) | *CCGGATCCGGATAGGGCATGCCGTGGGTGA TGATGG |
| F2-RecAnei (SEQ ID NO: 5) | CGTTCCAGCGTCTTGCGGAAACG |
| R2-recAnei (SEQ ID NO: 6) | CCGTTTCAGTCTCGATCATGC |

TABLE 1-continued

Primers used to identify and isolate
the recA gene from A. tumefaciens

| Primers | Sequences |
|---|---|
| F3-RecAnei (SEQ ID NO: 7) | GCATTGGTGAACATCAGTGTCGG |
| F-RecA-frt (SEQ ID NO: 8) | \*\*CCACCGGACGCGAACGCCCGGACCTTCGA ATGCATCAGCCCTCGTGTAGGCTGGAGCTGC TTC |
| R-RecA-frt (SEQ ID NO: 9) | \*\*CCTGTGCGGCTTCAATAACCTAAAGGTGG ATCGGATGGCACAACATATGAATATCCTCCT TAG |

*The underlined sequence of the BamHI digestion site is added for cloning purpose.
**The 43 bp sequence from both ends of recA including 9 bp of the gene (in bold font) is included in these primers. Sequences in these primers for amplifying the antibiotic cassettes flanked with frt sites are indicated in italic.

Example 2 Cloning, Characterization, and Sequence Analysis of the recA Gene from *A. tumefaciens* (LBA4404)

To construct the recA gene knock-out strains of *A. tumefaciens* (LBA4404), the location of the recA gene is assessed to determine if the location of the recA gene is present in the same genomic context as other recA gene isolates from *Agrobacterium* and *Rhizobium* species (Goodner B et al., 2001. Genome sequence of the plant pathogen and biotechnology agent *Agrobacterium tumefaciens* C58. Science 2942323-2328; and, Slater S C et al., 2009. Genome sequences of three *Agrobacterium* biovars help elucidate the evolution of multi-chromosome genomes in bacteria. *J Bacteriol.* 191(8):2501-11). Accordingly, the neighboring sequences located upstream and downstream of recA from *A. tumefaciens* (C58), *A. vitis* (S4), *A. radiobactor* (K84), *Rhizobium leguminosarum* and *Rhizobium* sp. NGR234, are searched for highly conserved sequences to design primers (F-recAnei and R-RecAnei in Table 1). These sequences are located about 1.5 kb upstream and downstream from the recA gene. These sequences are amplified by PCR using the primers that bound to a region containing the recA gene from *A. tumefaciens* (LBA4404). The resulting 3.7 kb PCR fragment is cloned into the pWM91 plasmid to generate a new plasmid that is labeled as pWM-recAnei (see FIG. 1) (Metcalf W W, Jiang W, Daniels L L, Kim S K, Haldimann A, Wanner B L. 1996. Conditionally replicative and conjugative plasmids carrying lacZ alpha for cloning, mutagenesis, and allele replacement in bacteria. *Plasmid.* 35(1):1-13). The PCR amplified recA gene fragment is submitted for sequencing using recAnei primers as listed in Table 1. The sequencing data identified the recA gene from *A. tumefaciens* (LBA4404) which is presented as SEQ ID NO: 10. Furthermore, the sequencing data indicated that the recA gene from *A. tumefaciens* contains the same genomic context as other relative strains; it is flanked by alaS in the downstream direction and Atu1875, a carbohydrate kinase, in the upstream direction (the genomic sequence containing the recA gene and the upstream and downstream flanking sequences is also provided as SEQ ID NO: 11).

Figure 2:
FIG. 2 illustrates a relatedness of recA from *A. tumefaciens* (LBA4404) with the recA gene from other *Agrobacterium* strains. The phylogenic tree is generated using phyML (available at world wide web phylogeny.fr.) (Dereeper A, Guignon V, Blanc G, Audic S, Buffet S, Chevenet F, Dufayard J F, Guindon S, Lefort V, Lescot M, Claverie J M, Gascuel O. (2008) Phylogeny.fr: robust phylogenetic analysis for the non-specialist. Nucleic Acids Research. 36 (Web Server Issue):W465-9). The internal 969 bp fragment of recA (34-1005 bp) is used to perform this alignment analysis. The other strains are selected from the representative recA genomovars (G-) in the genus *Agrobacterium* and related taxa as indicated (Costechareyre et al., 2010).

The recA gene of *A. tumefaciens* (LBA4404) is almost identical in sequence to the recA gene from genomovar-1 isolates of biovar 1 *Agrobacterium* strains such as S 377, TT111 and ATCC4720. In addition, the recA gene of *A. tumefaciens* (LBA4404) shares 92% identity in nucleic acid sequence with the recA gene of the genomovar-8 strain, i.e., C58 (Costechareyre et al., 2010). The overall relatedness of the recA gene of *A. tumefaciens* (LBA4404) as compared with the recA gene from other *Agrobacterium* strains and related taxa can be compared, and a phylogenetic tree of this comparison is shown in FIG. 2. The sequence comparison results of the recA gene of *A. tumefaciens* (LBA4404) suggest that quite a few regions of the *A. tumefaciens* (LBA4404) genome contained genomic DNA sequences unrelated to those of *A. tumefaciens* (C58). Further sequence comparisons indicated that chromosomal polymorphisms exist even among the closely related biovar 1 isolates of *Agrobacterium* spp.

Example 3 Replacement and Disruption of the recA Gene in MMS-Resistant Cosmids with a Kanamycin or Chloramphenicol-Resistance Cassette The bacteriophage λ-based red recombination is used to introduce antibiotic resistance cassettes into the recA gene of *A. tumefaciens* (LBA4404) carried on pCP-MMSR2 (Datsenko K A, Wanner B L. 2000. One-step inactivation of chromosomal genes in *Escherichia coli* K-12 using PCR products. *Proc Natl Acad Sci USA.* 97(12):6640-5). Briefly, using primers F-recA-frt and R-RecA-frt listed in Table 1, DNA fragments encoding the chloramphenicol and kanamycin antibiotic resistance genes are amplified from pKD3 and pKD4, respectively. These amplified PCR fragments encoding the antibiotic cassettes are flanked with 43 bp sequences located upstream and downstream of the recA gene. The sequences further included 9 bp from each end of the recA gene. The resulting linear PCR amplification products are electroporated into the *E. coli* (HB101) strains that harbored the MMS-resistant cosmids, pCP-MMSR2 and pKD20, for red-mediated recombination. The plasmid pKD20 provides the red recombinase and can be cured following recombination by growth of the transformed strains at 42° C. Next, the disruption of the recA gene within the cosmid is confirmed by testing its inability to restore MMS resistance of *E. coli* (HB101) and by sequence analysis using primers F3-recAnei and R2-RecAnei (Table 1). Several such constructs met the requirement of being unable to complement the recA mutation in *E. coli* (HB101). One of each antibiotic resistance class, pCP-MMSRΔrecAkan, and pCP-MMSRΔrecACm is retained for constructing the recA knock-out strains of *A. tumefaciens* (LBA4404).

Example 4 Replacement and Disruption of the recA Gene in the Chromosome of *A. tumefaciens* (LBA4404) with a Kanamycin or Chloramphenicol-Resistance Cassette The two recA-disrupted cosmid clones described above are transformed into *A. tumefaciens* (LBA4404) for marker-exchange of the disrupted recA gene of the cosmid into the *A. tumefaciens* (LBA4404) chromosomal recA gene. Briefly, following the electroporation of the recA-disrupted cosmids into *A. tumefaciens* (LBA4404), transformants are selected and purified on nutrient agar plates containing tetracycline and kanamycin or chloramphenicol. Next, the transformants are inoculated in liquid culture containing only kanamycin or chloramphenicol. These cultures are sub-cultured three times to increase the probability of double cross-over events and loss of the cosmid clone. Fifty-micro liter volumes of 1000-fold diluted culture are spread on plates containing the appropriate antibiotics, and about 100-200 colonies are picked and screened for double-crossovers by testing for resistance to kanamycin or chloramphenicol and sensitivity to both tetracycline and MMS. The resulting candidate recA knock-out *Agrobacterium* strains are isolated and labeled as UIA777 (Cm) and UIA770 (Kan). The isolated recA knock-out strains are further confirmed by PCR and sequence analysis using primers listed in Table 1. The full process of constructing the recA gene knock-out in *A. tumefaciens* is illustrated in FIG. 1.

Example 5 Characterization of Growth Properties of recA Knock-Out Strains of *A. tumefaciens* (LBA4404) Strains The two *A. tumefaciens* (LBA4404) knock-out recA strains, UIA777 and UIA770, are observed for bacterial growth rates. It is observed that the recA knock-out strains exhibited a one-hour growth delay as compared to the wild-type strain when inoculated into MGL liquid medium (see FIG. 3). Further observations indicate that both recA knock-out strains grew even slower on solid nutrient agar plates. For instance, it is observed that the recA knock-out strains required over three days for the colonies to reach about 1-2 mm in diameter while the wild-type strain grew to the same 1-2 mm diameter of size in about two days.

The two *A. tumefaciens* (LBA4404) knock-out recA strains, UIA777 and UIA770, are observed for sensitivity to methyl methanesulfonate (MMS) and ultra-violet (UV) irradiation. The sensitivity to MMS and UV irradiation, is a common characteristics of bacterial recA knock-out strains (Farrand S K, O'Morchoe S P, McCutchan J. 1989. Construction of an *Agrobacterium tumefaciens* C58 recA mutant. J Bacteriol. 171(10):5314-21). Overnight cultures of the *A. tumefaciens* (LBA4404) recA knock-out strains are diluted 100-fold into 3 ml of MGL medium and grown with shaking to early-stationary phase. The resulting cultures are then ten-fold serially diluted in 0.9% NaCl and 5 μl samples are spotted onto the surface of nutrient agar plates. For MMS treatment, 0.01% MMS is included into the media. For UV irradiation, the plates are exposed to a UV light source (Amersham-Pharmacia Biotech, Pittsburgh, Pa.) to deliver precise doses of UV as measured by an internal UV dosimeter. Immediately after exposure, the plates are covered and incubated in a lightproof black box at 28° C. for 24 hours. The titer of the culture at the zero dilution is used to determine the survival of cells in the presence of MMS or following exposure to various doses of UV irradiation. As shown in Table 2, the two *A. tumefaciens* (LBA4404) recA knock-out strains, UIA777 and UIA770, are sensitive to both MMS and UV irradiation as compared to wild-type *A. tumefaciens* (LBA4404).

TABLE 2

Characterization of *A. tumefaciens* (LBA4404) recA knock-out strains, UIA777 and UIA770, to MMS and UV irradiation treatments

| Strains | No treatment | MMS | UV treatment | | |
|---|---|---|---|---|---|
| | | | 4 J/m² | 8 J/m² | 16 J/m² |
| LBA4404 | $2.9 \times 10^6$ | $1.5 \times 10^6$ | $2.6 \times 10^6$ | $1.5 \times 10^6$ | $4.3 \times 10^5$ |
| UIA777 | $1.3 \times 10^6$ | $<10^1$ | $1.3 \times 10^4$ | $6.3 \times 10^2$ | $<10^1$ |
| UIA770 | $1.0 \times 10^6$ | $<10^1$ | $2.6 \times 10^4$ | $3.3 \times 10^2$ | $<10^1$ |
| UIA770 (pSOM301) | $2.0 \times 10^6$ | $1.2 \times 10^6$ | $2.5 \times 10^6$ | $1.4 \times 10^6$ | $6.6 \times 10^5$ |

Figure 3:
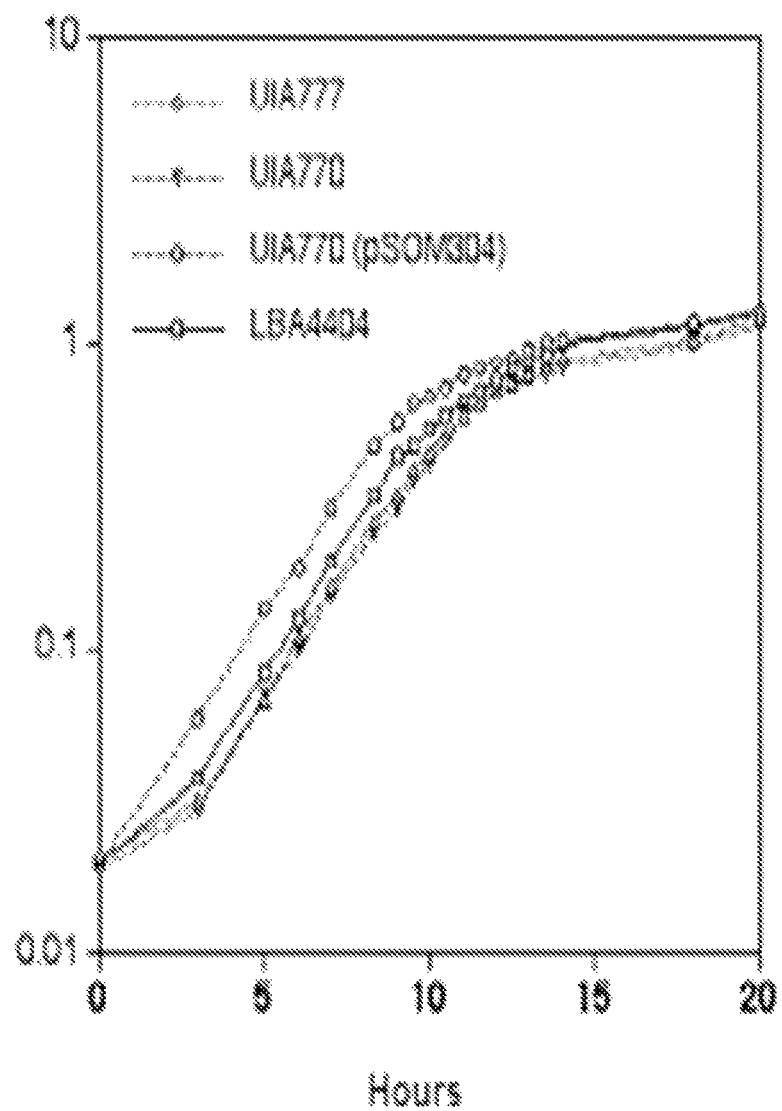
FIG. 3 illustrates the growth rates of two exemplary *A. tumefaciens* (LBA4404) mutant recA minus strains, UIA777 and UIA770 as compared with wild-type and complemented strains. For these assays MGL medium is used.

Example 6 Complementation of recA Knock-Out *A. tumefaciens* (LBA4404) Strains Plasmid pSOM301, a derivative of pCP13/B containing the recA gene from C58 (Farrand S K, O'Morchoe S P, McCutchan J. 1989. Construction of an *Agrobacterium tumefaciens* C58 recA mutant. J Bacteriol. 171(10):5314-21), is tested for its ability to complement the slow growth, MMS and UV sensitivity of *A. tumefaciens* (LBA4404) recA knock-out strain, UIA770. The pSOM301 plasmid restored the growth delay and small colony phenotype of UIA770 (FIG. 3). It can also restore resistance of UIA770 to MMS and UV irradiation to levels similar to those shown by wild-type *A. tumefaciens* (LBA4404) (Table 2).

Example 7 Characterization of Isolated Plasmid from the recA Knock-Out *A. tumefaciens* (LBA4404) Strains The wild-type, *A. tumefaciens* (LBA4404) strain harbors the vir helper plasmid pAL4404 (Hoekema A, Hirsch P R, Hooykaas P J J J, Schilperoort, 1983. A binary plant vector strategy based on separation of vir and T-region of the *Agrobacterium tumefaciens* Ti-plasmid. Nature 303:179-180). The pAL4404 helper plasmid (i.e., Ti plasmid) is isolated from recA knock-out strains. Next, the helper plasmid is subjected to gel electrophoretic analysis. The resulting gel analysis indicated that the isolated plasmids from the *A. tumefaciens* (LBA4404) UIA777 and UIA770 strains both harbored a single plasmid that migrates with the same mobility as pAL4404.

Example 8 Introduction of the Ternary Plasmid from the recA Knock-Out *A. tumefaciens* (LBA4404) Strains The ternary plasmid (pDAB9292) as previously described in International Patent Application No. PCT/US2011/046028, herein incorporated by reference, is transformed into the two *A. tumefaciens* (LBA4404) recA knock-out strains, UIA777 and UIA770. The introduction of the ternary plasmid into the *Agrobacterium* strains is confirmed by molecular confirmation assays (i.e., restriction enzyme digestion and sequencing).

Figure 4:
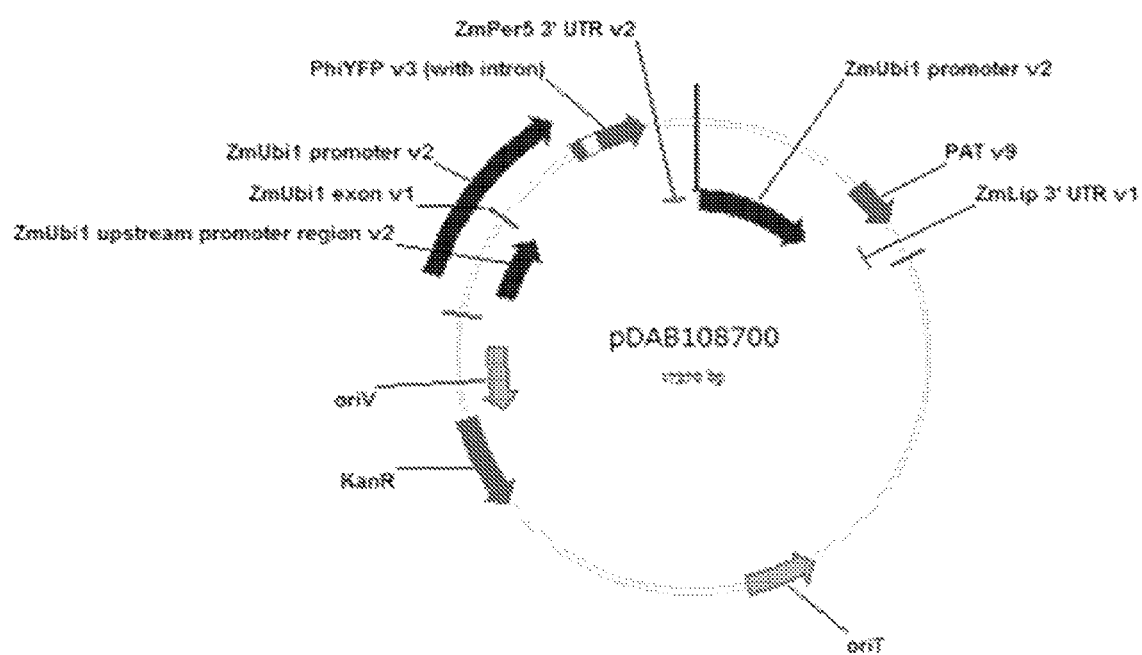
FIG. 4 illustrates a plasmid map of binary plasmid, pDAB108700, showing the construct design and duplication of the *Zea mays* Ubiquitin-1 promoter within the construct.

Example 9 Stability of a Binary Plasmid Containing Repeated Gene Elements in the recA Knock-Out *A. tumefaciens* (LBA4404) Strains The *A. tumefaciens* (LBA4404) recA knock-out strains are tested to assess the stability of a binary plasmid containing repeated gene elements. In previous experiments it is observed that the use of repeated gene elements within the binary plasmid would rearrange when the binary plasmid is cloned into *A. tumefaciens* (LBA4404). The binary plasmid, pDAB108700 (SEQ ID NO:12), is illustrated in FIG. 4. As shown, pDAB108700 contains two gene expression cassettes, both driven by the same promoter. The first gene expression cassette contains the *Zea mays* Ubiquitin-1 promoter (Zm Ubi1 promoter v2) linked to the phi-yellow fluorescent protein (PhiYPF v3) gene sequence and terminated with the *Zea mays* peroxidase 5 3' UTR (ZmPer5 3'UTR v2). The second gene expression cassette contains the *Zea mays* Ubiquitin-1 promoter (Zm Ubi1 promoter v2) linked to the phosphinothricin acetyl transferase (PAT v9) gene sequence and terminated with the *Zea mays* lipase 3' UTR (ZmLip 3'UTR v1).

TABLE 3

Characterization of *A. tumefaciens* (LBA4404) knock-out recA strain, UIA777, for stability of binary plasmids

| *Agrobacterium tumefaciens* Strains | Relative Stability |
|---|---|
| LBA4404 wildtype | ~80% stability |
| UIA777 strain | ~100% stability |
| LBA4404 wildtype with ternary plasmid (pDAB9292) | ~60% stability |
| UIA777 strain with ternary plasmid (pDAB9292) | ~70% stability |

The binary plasmid, pDAB108700, is transformed into the *A. tumefaciens* strains of Table 3. After transformation, two bacterial colonies are isolated from the transformation of each bacterial strain. Each colony is grown-up and the binary plasmid DNA is isolated for validation with a series of restriction enzyme digestions (i.e., NotI, EcoRI, FsoI, and PstI digests). Next, one specific colony from the first experiment is selected and streaked-out on solid medium. Ten of the colonies that grew on the solid medium are picked and grown-up. The binary plasmid DNA is isolated for another round of validation with a series of restriction enzyme digestions (i.e., NotI, EcoRI, FsoI, and PstI digests). The banding patterns of the restriction enzyme digestions are observed for the production of expected size plasmid-DNA fragments. The colonies that produced banding patterns with aberrant and unexpected sizes of plasmid-DNA fragments are identified as unstable. The colonies that produced banding patterns with an expected size of plasmid-DNA fragments are identified as stable. The total percentage of plasmids that did not exhibit any rearrangements for each different strain is calculated and the results are presented in Table 3.

Example 10 Plant-Mediated Transformation with the *A. tumefaciens* (LBA4404) recA Knock-Out Strains Plant species are transformed according to embodiments of the subject disclosure using techniques that are known in the art. The two *A. tumefaciens* (LBA4404) recA knock-out strains, UIA777 and UIA770, containing a binary plasmid are used for the plant-mediated transformations. As a result of the transformation, a gene expression cassette containing a selectable marker is integrated as a T-strand into a genomic locus within the plant chromosome. The integration of the T-strand within the upstream and downstream genomic flanking sequences results in a transgenic event, stably integrated within the genome of a transgenic plant.

Corn plants may be transformed with either of the two *A. tumefaciens* (LBA4404) recA knock-out strains, UIA777 and UIA770, containing a binary plasmid by utilizing the same techniques previously described in Example #8 of WO 2007/053482. The resulting transformation incorporates a gene expression cassette containing an agronomic trait that is integrated as a T-strand into a genomic locus within the plant chromosome.

Soybean plants may be transformed with either of the two *A. tumefaciens* (LBA4404) recA knock-out strains, UIA777 and UIA770, containing a binary plasmid by utilizing the same techniques previously described in Example #11 or Example #13 of WO 2007/053482. The resulting transformation incorporates a gene expression cassette containing an agronomic trait that is integrated as a T-strand into a genomic locus within the plant chromosome.

Cotton plants may be transformed with either of the two *A. tumefaciens* (LBA4404) recA knock-out strains, UIA777 and UIA770, containing a binary plasmid by utilizing the same techniques previously described in Examples #14 of patent application U.S. Pat. No. 7,838,733 or Example #12 of WO 2007/053482 (Wright et al.). The resulting transformation incorporates a gene expression cassette containing an agronomic trait that is integrated as a T-strand into a genomic locus within the plant chromosome.

Canola plants may be transformed with either of the two *A. tumefaciens* (LBA4404) recA knock-out strains, UIA777 and UIA770, containing a binary plasmid by utilizing the same techniques previously described in Example #26 of patent application U.S. Pat. No. 7,838,733 or Example #22 of WO 2007/053482 (Wright et al.). The resulting transformation incorporates a gene expression cassette containing an agronomic trait that is integrated as a T-strand into a genomic locus within the plant chromosome.

For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5): 587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," Plant Physiol. 1997 November; 115(3):971-980. For *Agrobacterium*-mediated transformation of rice, see, e.g., Hiei et al., "Transformation of rice mediated by *Agrobacterium tumefaciens*," Plant Mol. Biol. 1997 September; 35(1-2):205-18.

The latin names for these and other plants are given below. It should be clear that thes plants may be transformed with either of the two *A. tumefaciens* (LBA4404) recA knock-out strains, UIA777 and UIA770, containing a binary plasmid. As a result either of the two *A. tumefaciens* (LBA4404) recA knock-out strains, UIA777 and UIA770, can be used to transform an agronomic trait into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and Table Beets (Beta spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense*, and *frutescens*), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (Sorghum spp.), Alfalfa (*Medicago sativa*), Carrot (*Daucus carota*), Beans (*Phaseolus* spp. and other genera), Oats (*Avena sativa* and strigosa), Peas (*Pisum, Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis*, Poa, *Cynodon*, and other genera), Clover (*Trifolium*), Vetch (*Vicia*). Transformation of such plants with either of the two *A. tumefaciens* (LBA4404) recA knock-out strains, UIA777 and UIA770, containing a binary plasmid, for example, is contemplated as an embodiment of the subject disclosure.

The two *A. tumefaciens* (LBA4404) recA knock-out strains, UIA777 and UIA770, containing a binary plasmid may be used for transformation of many deciduous and evergreen timber cropping systems. Transgenic timber species would increase the flexibility of over-the-top use of these herbicides without injury concerns. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), *eucalyptus* (*Eucalyptus* spp.), hickory (*Carya* spp.), maple (*Acer* spp.), oak (*Quercus* spp.), and pine (*Pinus* spp.).

Use of either of the two *A. tumefaciens* (LBA4404) recA knock-out strains, UIA777 and UIA770, containing a binary plasmid for the transformation of ornamental and fruit-bearing species is also within the scope of embodiments of this disclosure. Examples include, but are not limited to; rose (Rosa spp.), burning bush (*Euonymus* spp.), petunia (*Petunia* spp.), *begonia* (*Begonia* spp.), *rhododendron* (*Rhododendron* spp.), crabapple or apple (*Malus* spp.), pear (*Pyrus* spp.), peach (*Prunus* spp.), and marigolds (*Tagetes* spp.). While aspects of this invention have been described in certain embodiments, they can be further modified within the spirit and scope of this disclosure.

This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

APPENDIX

```
                     Sequence listing

PCP13/B left
                                                    SEQ ID NO: 1
ggcattcttggcatagtggt PCP13/B right
                                                    SEQ ID NO: 2
gctgaagccagttaccttcg F-RecAnei
                                                    SEQ ID NO: 3
ccggatccccgcgttccagcgtcttgcggaaacg R-RecAnei
                                                    SEQ ID NO: 4
ccggatccggatagggcatgccgtgggtgatgatgg F2-RecAnei
                                                    SEQ ID NO: 5
cgttccagcgtcttgcggaaacg R2-recAnei
                                                    SEQ ID NO: 6
ccgtttcagtctcgatcatgc F3-RecAnei
                                                    SEQ ID NO: 7
gcattggtgaacatcagtgtcgg F-RecA-frt
                                                    SEQ ID NO: 8
ccaccggacgcgaacgcccggaccttcgaatgcatcagccctcgtgtaggctggagctgcttc SEQ ID NO: 9
                                                    SEQ ID NO: 9
cctgtgcggcttcaataacctaaaggtggatcggatggcacaacatatgaatatcctccttag recA gene
                                                    SEQ ID NO: 10
atggcacaaaattctttgcgtctcgtagaggataaatcggtggataaaagcaaggcactggaagcggcgctct
cccagatcgaacggtcgttcggcaagggatcgatcatgaagctcggttccaatgaaaacgtggttgaagtaga
gaccatttcgacgggttctctcagcctggatatagcgctcggtatcggcggcctgccgaagggcgtatcgtt
gagatttacggcgccggaaagctccggtaagacgacgcttgcgttgcagacgatcgcggaagcccagaaaaagg
gcggcatctgcgccttcgtggatgccgagcacgcgctcgatccggtctatgcccgcaagctcggtgtggattt
gcagaaccttctgatctcgcagccggatacgggcgagcaggcgcttgaaatcaccgatacgctggtgcgctcc
ggtgccgtcgacattctggtcgtggactcggttgcggcgctgacgccgcgtgccgaaatcgaaggcgagatgg
gtgacagcctgccgggccttcaggcacgtctgatgagccaggcgctgcgcaagctgaccgcctcgatctccaa
gtcgaagtgcatggtgatcttcatcaaccagatccgcatgaagatcggcgtcatgttcggttcgccggaaacg
acgacgggcggtaatgcgcttaaattctacgcctcggtgcgtctcgacattcgccgtatcggcgccgtcaagg
agcgtgaagaggttgtcggcaaccagacccgcgtcaaggtcgtcaagaacaagatggcaccgccttcaagca
```

```
ggtggaattcgacatcatgtatggtgaaggcgtttccaagaccggcgagcttgtcgatctcggcgtgaaagcc
ggtatcgtcgagaaatccggtgcatggttctcctataacagccagcgtttggggcaggggcgtgaaaatgcca
agactttcctgcgcgacaatccggaaatggcaagcgagatcgaactggcgctgcgccagaacgccggtctgat
cgccgatcggttcctgcagaatggcggcccggaagctggcgaaagcgacgacggtcccgacgagggctga
``` recA genomic DNA fragment

SEQ ID NO: 11

```
agcgcgacgatcggcgcgccgcgctgtttggcagcggcaacctcttgcgaatagatgatggttaggagcgggg
agatggggcgggtcattctgtttgttccagactataaaaaaacgggttcatgccagcatttcggccttgggga
caagccccaacatggtctcgacactgtcttttgacaggtcttgggcggtggcgaaaggcgattcacggtgat
ggcggccgccgcggcacccaatcgcagggcctcagtgatggctttgcctccgtaatcgccgcgagataacct
gacgccatggcgtctccggccccggttacgtctttcacctcgcgatgatgggtgggtggaggcttgcggttt
gcgtcgcgttgaaggctaccacttcgcttgccgcacgggtgatgacgccgccggcaaggcctgcctgcggag
aatgcccggccagtcgcgaacattgtctgccgtctgtccggtcagcgcgcgcctctgcctggttcatgaag
agaatgtcgatatcggcgagcatgtccttcagcttcaccgccttggcgggcgaaatggcgatggccgcgagcg
gctttttggcaggcgcgggcaatgagaccgaagcgccttcaacgtatcctccggcagattggcatcgcaaagcag
aaggtcgctcgcggtaatcgcttcacgcaccgcgcgaactttgaggcggcgcggcgaaaacagcttgtaaagg
tccatatccgcaagtgcgatgacaagattgccgtcgcgctccagaatggcggtgtagcttggcgtgcggcgat
cgaggaaaacgaagggcgtatcttccacgcccgcctgccttgctgcctctgccaccgcttcgccggtcacgtc
gccgccgcgcggtgcgatgatacggacggcaaaaccgagccgggaaagattgcgcgccgcattgaaaccgccg
ccgccagcctcttccatccatgagccaggattgctgggcgccgggcgccgtttcagtctcgatcatgccgcgc
ctgtcatatgcgcgccgcccagaacgagtatcttcttcacgcttgtgtttccctctttcgccggatggaaaagg
tggacgattcgtcccaatcttctgtttgttccccttcacatccggttcgcagcgataggccggacacggaaaa
acgaaagcagaacaaaccacttatcgctatttgttttcaatatgctggctgccgcttgcgatatgagaacaaa
tagagtacatcctatttccatactgcttcattgcctgtgcggcttcaataacctaaaggtggatcggatggca
caaaattctttgcgtctcgtagaggataaatcggtggataaaagcaaggcactggaagcggcgctctcccaga
tcgaacggtcgttcggcaagggatcgatcatgaagctcggttccaatgaaaacgtggttgaagtagagaccat
ttcgacgggtctctcagcctggatatagcgctcggtatcggcggcctgccgaaggggcgtatcgtgagattt
acggcccggaaagctccggtaagacgacgcttgcgttgcagacgatcgcggaagccagaaaaagggcggcat
ctgccgccttcgtggatgccgagcacgcgctcgatccggtctatgcccgcaagctcggtgtggatttgcagaac
cttctgatctcgcagccggatacgggcgagcaggcgcttgaaatcaccgatacgctggtgcgctccggtgccg
tcgacattctggtcgtggactcggttgcggcgctgacgccgcgtgccgaaatcgaaggcgagatgggtgacag
cctgccgggccttcaggcacgtctgatgagccaggcgctgcgcaagctgaccgcctcgatctccaagtcgaag
tgcatggtgatcttcatcaaccagatccgcatgaagatcggcgtcatgttcggttcgccggaaacgacgacgg
gcggtaatgcgcttaaattctacgcctcggtgcgctcgacattcgcgtatcggcgccgtcaaggagcgtga
agaggttgtcggcaaccagacccgcgtcaaggtcgtcaagaacaagatggcaccgccttcaagcaggtggaa
ttcgacatcatgtatggtgaaggcgtttccaagaccggcgagcttgtcgatctcggcgtgaaagccggtatcg
tcgagaaatccggtgcatggttctcctataacagccagcgtttggggcaggggcgtgaaaatgccaagacttt
cctgcgcgacaatccggaaatggcaagcgagatcgaactggcgctgcgccagaacgccggtctgatcgccgat
cggttcctgcagaatggcggcccggaagctggcgaaagcgacgacggtcccgacgagggctgatgcattcgaa
ggtccggccgttcgcgtccggtggcttgccggcatgagccggtatggatcaaaagggtcgtgcgattttcct
cgcgtggccctttttctttgcctagacgccttggtgcgcctccatggctggacagggcaggatgcggacgata
aaagcctttgatttttgcaagatagccatcattcgggatggcggtgatggactccagctgtgagcggtgtgtgg
gcatgagcggtgtgaatgaaattcggtcgacctttctcgactacttcaagaagaacggacacgagattgtgcc
ctccagcccgctggtgccgcgcaacgatccgacgctgatgttcaccaatgcggcatggtgcagttcaagaac
gtcttcaccggtctcgaaagccgtcctattccaccgccgcctcggcgcagaaatcgtgcgcgccggtggca
agcataacgacctggacaatgtcggttatacggcccgtcaccatacgttcttcgaaatgctcggcaatttctc
ctttggcgactatttcaaggaagaggcgattaccatgcctggaacctgatcaccaaggaattcggcatcgac
cgcaaccgtctgctggtcacggtctatcacaccgacgacgaggcttttaatctctgggaagaagatcgccggtt
tctccgacgatcgcatcatccgtattccgaccagcgataatttctgggcatgggcgataccggtccgtgcgg
tccctgctcggaaatcttctatgaccacggcgatcatatctgggcggaccgccggttcgccgaagaggat
ggcgaccgtttcatcgaaatctggaacctcgtcttcatgcaatatgagcagctgacgaaggaagagcgcatcg
atctgccgcgccgtcatcgacaccgcatctcgagcgcattcggcgtttgttgcagggcaaacacgacaat
tacgacaccgatctgttccgggcgctgattcggcctccgtcgaagcgaccggcgttccggcagagggcgaga
agcgcgccagccatcgcgtcattgccgatcatctgcgctcctccgcctttcctgatcgccgatggcgtcctgcc
gtcaaatgagggccgtggtacgttctgcgccgcatcatgcgccgcgccatgcgccatgccgagcttctcggt
tcgcgcgagccgctgatctacaagctgctgccggcgctgatacagcagatgggccgcgcctatccggaactgg
ttcgcgccgaggcgctgatctccgagacg
```

RecA protein

SEQ ID NO: 12

```
MAQNSLRLVEDKSVDKSKALEAALSQIERSFGKGSIMKLGSNENVVEVETISTGSLSLDIALGIGGLPKGRIV
EIYGPESSGKTTLALQTIAEAQKKGGICAFVDAEHALDPVYARKLGVDLQNLLISQPDTGEQALEITDTLVRS
GAVDILVVDSVAALTPRAEIEGEMGDSLPGLQARLMSQALRKLTASISKSKCMVIFINQIRMKIGVMFGSPET
TTGGNALKFYASVRLDIRRIGAVKEREEVVGNQTRVKVVKNKMAPPFKQVEFDIMYGEGVSKTGELVDLGVKA
GIVEKSGAWFSYNSQRLGQGRENAKTFLRDNPEMASEIELALRQNAGLIADRFLQNGGPEAGESDDGPDEG
``` recB gene

SEQ ID NO: 13

```
atgactttcacccatcacgcaaagcgcgtcctgacgatcgctgcgggaacaccgttcctcaaaacgctcgcgg
aaacgctgtgtgacgggacactgacagccggctataaatacgaccctgcggatccgtttcgcttgccaaggt
gacgatctatgttccgaccggcgtccgcccgcgtgctgcgctcagagtttgtcgatcttctgggcggccgt
tccgccatttttgccactgatcggccgctcggcgaaaccgatgacgacagcggcttcttcgagatcgaaatc
ctgagatcatggatctggcgccgcgattccggcaccgccggcaaatcgagctggcgcgcctcattctggc
atgggcgcaacagcctgcccgacgccatcagggccatccattcggactcaccacttgtcgccccgccagccct
gccgacgccatatggctggcgcgcgcgcttggcgaagtgatcgatgcgatggatacggaagaaaaagaatggg
aggcgctcgcgcatctcgataccggcgatcacgcccaatggtggcagctgacggcggatttcctgaaaatcgc
```

Sequence listing

```
cagcgtgttctggcccgccgtcttgccgaactcaatcgaacttccgcaggccgacatcgcaacggcatcctg
agggcagaggcgaaccggcttgccaacctgccggacaccggaccaatcatcgttgcgggctccacgggctcaa
ttccggcagcagcagaccttatcgcctctgtcgcctccctgccccagggcgtcgtcgtgcttccgggcctcga
tcttacgatgccggaggaacaatggggaggctattgccgaggacctaccgatccttcaagccgcacccattcg
caatacggactctacatgctgttgcagaagctcgatatcatgcgagacgatgtcgttcagattggcgctatcg
atagcgatcttgaaaaacgcgcggcggttttttcggcagcacttgctcctgccaaatccaccagcgactggaa
ccgctggcgtgaggacaagcaaccggattttcgacgatgcttttgcggcagcgaccctgatagaagctgca
aacgagcgcgaagaggcaaccgcaattgcggtggcgctgcggctggcggcttgaagcgccgggcgctggccgcc
cgtctcaggccgcgctgatcacgcccgatcgcggactggccaggcgcgtggcgacggaattgcaacgcttcgg
tatcgaagccgacgattccgccggtacgccgcttccgccacgccgcaggccggactgacgcaactcgcactg
gaagctatcctcaggcccggagatccggtgccggtcatttccttctgaaacatccgctcagccgtttcgggc
tttcgctggaggcttttacaaaagcatcaaaggcgctggaattgatcgcacttagaggcggccgtcgaaac
ggaaatcggcaatctggaggcggttctcgatgcgcaactggcggcgcagcgtgatgaccggcatccgcctgcc
tggaggctggcactgccgagggaagcgtagacgccgcgcgatctggcacgccggatcgccgtttcgacag
agccgcttggcagcgcattcgttcgtagcgaccgctcaggccggtctttcacggacaaattgccgctttccga
ttgggccgagcggacgggccgggtgatcgaagccatctgccggatgacaacaacgatcttgccactctctgg
tccggcgaggcaggcgacaagctttccggcctgtttggcgaattgatggaaagcggcgaaatcctggatgcgg
atggtccgcaatgggctgatatcttcgcggcactggtggctggcgaatcgatcaagccgcgatccatgcgcca
tccgcgcattttcattttcggtgccttgaggcacgactgcaaagcgtcgacactgtcgtgatcggcggtctc
aatgaagggctttggccgggccagacggcaaacaacccgtttctgtcccgcaacatgaagacagccatcggtc
tggaaccgccggagcggcgcatcggccagctggcgcacgattttcgagatggcgaacgggacacggcagatttt
ctacagccgcgcgctcagacagggctcgacacccgcagtcgcatcgcgctggctgcagcgattgctggcactc
ggcggcgaggattttgccgaacagctgaagaagcgcggcgagacctatcgccactgggcagccctgatggatg
cgaccatcgaccaggaagcagcaaagcgccctgcccccaaagcgtcgcggccgacttgcagccgaagagctattc
cttcagcgaagtgggcaggctgcgccgtgaccccattcgatctacgcgcggcgtatcctgaagctcaacccg
cttgatggcttcaaccgcgatcccaatgccgccgaccgtggcacgctctatcatgcaatcattgagcgctatt
cccgcgaggggcatattcccggcacaccggcatcgctcgaggccatgcagcgtattctggatgagagtttcga
cgcggaagatcttcctgcacatgtcgatgtcatctggcgcccgcgattcgaggcggttggcacgcgcctttatc
gactgggagaaagaacgacatccatccatccgccgcagcttttttcgaggcgcgtgccggacaggaaatccccg
aggcaggcataaggctgaccggcatcgccgaccgcatagatatcaagaccggcggtcaggcggatattatcga
ctacaaaacggggcttgcgccttcagtcaatcaggcgcgcgcgctgtcgacccgcagctcgcgctggaagcg
gcagcactgatgcggggcgccttccgcgaggcgggttcgcagacaccggaaaaaccttatctatgtgcgcctgc
ggccgggtacccgttttttttgccgaccaggtgaataacgaacactccaaccggggtggcaaaaaagcaccgaa
atcggcaattgagctggcaaccgaatcaatcgatcagctggccaagttcgtgcgttcgctgcgtgatggcgag
aacggttttgcctcgcggctggtgccggaggagcagcagtcctatgggggggaatatgaccacctcgcccgcg
tttcggaatggtcgacggcagaaccgggagacggcgatgatgattga
```

RecB protein
SEQ ID NO: 14

```
MTFTHHAKRVLTIAAGTPFLKTLAETLCDGTLTAGYKYDPADPLSLAKVTIYVPTRRSARVLRSEFVDLLGGR
SAILPLIRPLGETDDDSGFFEIENPEIMDLAPPISGTGRQIELARLILAWRNSLPDAIRAIHSDSPLVAPASP
ADAIWLARALGEVIDAMDTEEKEWEALAHLDTGDHAQWWQLTADFLKIASVFWPARLAELNRTSAGRHRNGIL
RAEANRLANLPDTGPIIVAGSTGSIPAAADLIASVASLPQGVVVLPGLDLTMPEEQWEAIAEDPTDPSSRTHS
QYGLYMLLQKLDIMRDDVVQIGAIDSDLEKRAAVFSAALAPAKSTSDWNRWREDKQPGFFDDAFAAATLIEAA
NEREEATAIAVALRLALEAPGAGRPSQAALITPDRGLARRVATELQRFGIEADDSAGTPLSATPQAGLTQLAL
EAILRPGDPVPVISLLKHPLSRFGLSLEAFTKASKALELIALRGGRVETEIGNLEAVLDAQLAAQRDDRHPPA
WRLALPEGSVDAARDLARRIAVSTEPLGSAFVRSDRSGRSFTDKLPLSDWAERTGRVIEAICADDNNDLATLW
SGEAGDKLSGLFGELMESGEILDADGPQWADIFAALVAGESIKPRSMRHPRIFIFGALEARLQSVDTVVIGGL
NEGLWPGQTANNPFLSRNMKTAIGLEPPERRIGQLAHDFEMANGTRQIFYSRALRQGSTPAVASRWLQRLLAL
GGEDFAEQLKKRGETYRHWAALMDATIDQEAAKRPAPKPPADLQPKSYSFSEVGRLRRDPYSIYARRILKLNP
LDGFNRDPNAADRGTLYHAIIERYSREGHIPGTPASLEAMQRILDESFDAEDLPAHVDVIWRPRFEAVARAFI
DWEKERHPSIRRSFFEARAGQEIPEAGIRLTGIADRIDIKTGGQADIIDYKTGLAPSVNQARALLDPQLALEA
AALMRGAFREAGSQTPENLIYVRLRPGTRFFADQVNNEHSNRGGKKAPKSAIELATESIDQLAKFVRSLRDGE
NGFASRLVPEEQQSYGGEYDHLARVSEWSTAEPGDGDDD
``` recD gene (exodeoxyribonuclease V)
SEQ ID NO: 15

```
atgttattttcaccgcaacaggacgaagcgctcaaggctgtttcccgctggctgaaggaaggccggacgccgg
ttttccggttgttcggttatgccggaaccggcaagacgacgcttgccaaacattttcgcggaaaatgtcgatgg
cgaagtgctgtttgcggcctttaccggcaaggcggcaggtgctgcgctcgcgggggcgaccaatgcccgc
accatccattcgctgatctaccgcccgcgcggcgaagagaccgtggaagacgaggagaccggcaagacctcgg
tcgcgccaatgttttccatcaaccgccagacgcccgctcgccaaggcggcactcatcatcgatgaatgttc
gatggtggatgagcagctcggcaaggatctgatgagcttcggcacgcctatcctggtgctcggcgatcccggg
cagttgccgccagtttcaggcggttggcttcttcacggagcaggagcctgattacctgctctccgaaattcatc
ggcaggccaaggacaatcccatcatccaccttgccatggatgtgcgggaaggccgcgagatcatgcgtggcga
ttacggtgccgcgcaggtgatttccaagtccgaggtgacacgatcgctcgtgctcgatgccgatcaggtgctc
gtcggcacaaatcgcacgcgacgccgttataaccagcggcttcgcgagctgaaggatttacggccgattatc
cgcaatccggcgacaagctggtttgcttgaggaacgatccggccaagggcctgctgaacggctctctctggca
ggtcatgagttcgtcgcgcgagacggtgaaacccggcatcaacctgatgatccgcctgaagacgacgatatg
gatcggggcgcggccaagatcaaattgctgaaggcggctttcgaggatgtggaaacgaaattccgtggacca
cccgcaagcgttatgacgagttcgatttcggctatgcgctgaccgtgcacaaggcgcagggtcgcagtggaa
caatgtggttctctttgacgagagctatgccttccgcgattcgcgcgagcggtggctttacaccgccatcacc
cgccgccgcagaaacactcacaatcgttcgctga
```

SEQ ID NO: 16 RecD protein

```
MLFSPQQDEALKAVSRWLKEGRTPVFRLFGYAGTGKTTLAKHFAENVDGEVLFAAFTGKAAQVLRSRGATNAR
TIHSLIYRPRGEETVEDEETGKTSVAPMFSINRQSPLAKAALIIIDECSMVDEQLGKDLMSFGTPILVLGDPG
```

QLPPVSGGGFFTEQEPDYLLSEIHRQAKDNPITHLAMDVREGREIMRGDYGAAQVISKSEVTQSLVLDADQVL
VGTNRTRRRYNQRLRELKGFTADYPQSGDKLVCLRNDPAKGLLNGSLWQVMSSSRETVKPGINLMIRPEDDDM
DRGAAKIKLLKAAFEDVETEIPWTTRKRYDEFDFGYALTVHKAQGSQWNNVVLFDESYAFRDSRERWLYTAIT
RAAETLTIVR recF gene
SEQ ID NO: 17

Atgacgaataaggtgtcgcttttacggctgaaactcacggacttccgcaactatgcggcggcgtcgcttgcgc
tggatgaccgccacgtggtgctgacgggtgacaacggttccggcaagaccaatcctcggaggctgtttcgtt
tctgtgcccggaaggggcctgcgccgccaccctgtccgatgtgacgcgagtgggggcggaggccgccggt
ttttcgattttttgcggatgtcgacggcatggacggcgaggtcgccatcggaaccgggatcgagggtgacggcg
aggtagtgtcgcgccgcctgaggctgaacgggacatcggtgaagtcggtcgatgaattgacggatcatctgcg
ggtgctgtggctgacgcctgccatggatgggcttttttaccggttcatcctcggatcgccggcgttttctcgat
cggttggtgctctgctcgatcccgcgcatgggcggcgggcaagcgacttcgaaaaggccatgcgcggccgca
accgtctgcttcggaaggccgtttcgatccggtctggctggcgtatcgagaagcagatggcggaactcgg
catttccatggcgctcgcgcgctatgaaatgttgggtcttttgaaaagcctcatcgaaggccgttccggcaat
gctgccttcccctctgcagcgctggcgctctcggggtttcatggacgacacgctcaaccggccggctgtcgatc
tggaagacgagtataggcttatgctgcgcgaaggccggtatcgagacgcggcggcggggccgcacgcttgatgg
accgcaccgtgtcgatctgttcgtgcgccatgcggaaaagaacatggaggcagagcgttgctcgaccggagaa
cagaaggcgctgctggtggggattggtgcttgcgcatgcccagctcaccgccaacatgaccggccatgccgcgg
ttctgctgctcgacgaaattgccgcgcatctggatgagggcaggcgggcggctctgttcgatctcattcacgc
gctcggtggtcagagtttcatgaccggaacggatgcggcaatgttctccgcccttggcgacagggcgcaattc
ttcaatgtctcccacggggcatcacggcatga RecF protein
SEQ ID NO: 18
MTNKVSLLRLKLTDFRNYAAASLALDDRHVVLTGDNGSGKTNLLEAVSFLSPGRGLRRATLSDVTRVGAEEAAG
FSIFADVDGMDGEVAIGTGIEGDGEVVSRRLRLNGTSVKSVDELTDHLRVLWLTPAMDGLFTGSSSDRRRFLD
RLVLSLDPAHGRRASDFEKAMRGRNRLLSEGRFDPVWLDGIEKQMAELGISMALARYEMLGLLKSLIEGRSGN
AAFPSAALALSGFMDDTLNRPAVDLEDEYRLMLREGRYRDAAAGRTLDGPHRVDLFVRHAEKNMEAERCSTGE
QKALLVGLVLAHAQLTANMTGHAPVLLLDEIAAHLDEGRRAALFDLIHALGGQSFMTGTDAAMFSALGDRAQF
FNVSHGGITA recG gene
SEQ ID NO: 19
atgcgtcccgccattctcgatccgctatttgcttccgtctccaccctgccggtgtgggcggaagcttgccg
accttctggccaaactgctgagccgggaaaatgccgacgacacccgcgtgatcgatcttctgttccacgcgcc
atcaaacgtcatcgaccggcgcaaccgcccgggcatcgcgcttgccgctcccggcgccattgtcaccatccag
ggacgtgtcgaccggcatcagccagctccaccaggcaatcgttccgcgcccaccgtgttttcctgcatgacg
agaccggggaactggcgctgaccttcttccgcgcaagggagactggctttccaaggccttacccgtcgatgaa
gaggttctcgtcagcgccaaggtggactggttcaacggccgcttccatggtgcatccggatttcatggtga
agctctccgaggccgagaacctgccgctggtcgaagccgtttatccgatgacagccgggctgtctccgaaggt
gctgcggcgggcaattgaaggcgggctttcgaaactgccggtctttcccgaatggatcgacgaaacgctcaag
acccgtcagggtttcggcgacgtggcatcgagcttccgtgagttgcacgatccgcgcgacagcgccgatatcg
atcctcaggcccgcacgcagacggctcgcctacgacgaattcctggccgggcagctgtcactggcgctggt
gcggcaaagactgcgcaaggtcgcggccagccgatccgcgccaagggggacattgctgcaaaatcctgtcg
caactgcccttctccctgacgccgagccagaatgcctcggtgaaagatatcctgaccgatatggccagcgagg
accgtatgttgcggctgttgcaaggcgatgtcggcgcgggcaagacgctggtggcgctgatggctatggcaac
cgccgtcgaggccgagggcaggccggtgttgatggccccgaccgaaattcttgcccggcagcatttcgccacc
atctccaaactcgccaatgccgtgggcattacggttgaggtgctgaccggccgcaccaagggcaaggagcgtc
gcgagatcgaagaacgcgtggcctccggtgaggcacagatcgtcatcggcacccacgcgctgttccaggacag
cgtgagttacaagaacctcgtgctggccgtggtggatgagcagcaccgtttcggcgtacaccagcgcctgcgt
ctcaccgccaagggcatcacgccgcatatgctttgttatgaccgccacgccattccgcgcacgctggtgctg
gccgccttcggcgacatggatgtgtcgaaactcaccgaaaaaccggccgccgaaaaccgatccagaccgtga
caatccccacagagcgcatcggcgacatcgtcgagcggctgcgcgccgcgctgaaggagggcaagaaggccta
ctggatctgcccgctggtggaggagacggaagagtccgacctgatgtcggcggaagaacgacatgcggttctc
tcgcagatgctcggtgccaatatcggtctcatccatgggcgcatgagcgcctgagaaggacgccgccatgc
tggctttcaagaacggcgaaacccggctgctggtcaacgacagtggtggaagtgggtgtcgacgttccga
cgccacgatcatggtcatcgaacatgccgaacgttcggcctggcccagcttcaccagctgcgtggccgggtt
ggacgcggtgacgaggcctccacctgcatcctgctctataagggggccgctcagcgaaaacggccgcgcccgac
tttccatcctgcgcgacagcgaggacggcttcctgattgccgaagaggatttgaagctgcgcggcgaaggcga
actcctcggcacccgccagtccggaacccggcttccgcatcgccaagcctgaagccatgccgatctcctg
gaaatcgcccgcaaggacgccgcctatgtcatcgagcgcgaccccgaactgaccggcccgcgcggcgaaagcc
tgcgcaccctgctctatctgcaccgccgcgacgaagctatccgcttcctgcacgccggctga RecG protein
SEQ ID NO: 20
MRPAILDPLFASVSTLAGVGPKLADLLAKLLSRENADDTRVIDLLFHAPSNVIDRRNRPGIALAAPGAIVTIQ
GRVDRHQPAPPGNRSAPYRVFLHDETGELALTFFRAKGDWLSKALPVDEEVLVSGKVDWFNGRASMVHPDFMV
KLSEAENLPLVEAVYPMTAGLSPKVLRRAIEGGLSKLPVFPEWIDETLKTRQGFGDVASSFRELHDPRDSADI
DPQAPARRRLAYDEFLAGQLSLALVRQRLRKVAGQPIRAKGDIAAKILSQLPFSLTPSQNASVKDILTDMASE
DRMLRLLQGDVGAGKTLVALMAMATAVEAGGQAVLMAPTEILARQHFATISKLANAVGITVEVLTGRTKGKER
REIEERVASGEAQIVIGTHALFQDSVSYKNLVLAVVDEQHRFGVHQRLRLTAKGITPHMLVMTATPIPRTLVL AAFGDMDVSKLTEKPAGRKPIQTVTIPTERIGDIVERLRAALKEGKKAYWICPLVEETEESDLMSAEERHAVL
SQMLGANIGLHGRMSGPEKDAAMLAFKNGETRLLVATTVVEGVDVPDATIMVIEHAERFGLAQLHQLRGRV
GRGDEASTCILLYKGPLSENGRARLSILRDSEDGFLIAEEDLKLRGEGELLGTRQSGTPGFRIASLEAHADLL
EIARKDAAYVIERDPELTGPRGESLRTLLYLHRRDEAIRFLHAG recJ gene
SEQ ID NO: 21
atggcaatgatggagccggccgataccgtggtccgcgcatttcttagcgtggagcggtcggcgacagagcaac
gttgggtttcgcggctggatcaggccgcacagaaccgtgcgctggccatgtcccagatccatgccattcccga
actgattgcccgggtgctggccgggcgaggggtggggtggatgaggctctcgctttcctcgatccgaccatt
cgctcattgatgcccgaccgcatgtgctgacagattgcgaaaaggctgccgaaaggctggtccgcgccattg
agaccggcgagaaggtggcgatcttcggcgattatgacgttgatgtcgatgccgccgtcttccgcgctgatcg
gtttctcgcacatttcggggctgacgccggaaatctatattccagatcgtatttcgagggttatgggccgaac
ccggcggcgatgcagcagcttgccgccaatggccgcgaccctgatcgtgacggttgattgcggctccaccagcc
atgaatcgctgaatgccgcaaaggatgcgggaacagatgtggtggtgatcgatcaccaccaggtcggttcgga
actgccgccggcggtggcgttggtcaatcccaaccgcgaagacgatctttcggggcaggggcatctctgcgcc
gcaggcgtggtgtttctggttctggtcgccaccctcaggctgttgaaggacaggcgcaacagacaggcgttca
cgatcgatctgctggcgctgctggatatagtcgcactcgcaaccgtatgcgacgtggtgcccttgaaggggct
gaaccgcgcctatgtggtaaagggggttgattgccgcgcgccatatgaacaacgccgggctggcggcgctgttc
agaaaggcggggttgggcgggccggtgacaccgtatcattgtcggttttcctgatcgggcacgcatcaatgccg
gtggccgtattggcgatgccgcactgggtagccgtctgcttacactcgacgactcgtcacaggcggacgtgat
tgccgaaaagctggatgagctcaaccgcgagcgacaggcgatggaagccgtgatgctggcggaagccgaagcg
gaagcgctttatgagtatggcgacggtctggcgctggccgtcatcgttaccgcacgggaaaactggcatccgg
ggatcgttggcctgcttgcctcacgcctcaaggaccgttccgccgcccggccttgcaatcgcttttcgatcc
ctctggcaagggcacaggctccggccgctcgatcaatggttcgatatgggcagaatggtccgcgccgctgtg
gatgccggcctgctggtcaaggggtggcggtcacgccatggccgcgggcctgacggtggaacgcgccaatctcg
gcaaactccggaccttcttcgaggaagccgccgcaaagacggtgagcgagctggtggaaagcagcgtgcttaa
gatcgacggcgcaatcggcgcgtccggtgcgaccctgcagcttgtcgatcagctggaacaggctggtccttat
ggctccggccattctcagcccattttttgccgtgcctgcccaccggctgcgcgatgtgcgtctggtcggcacct
cccacgtcaagatcacgctggaggccatggatggctcacggctgacggcatcgcattccgcgccgcagaggc
ccctctggggcagatgctgctgaatgcgcgtggcaggtctatccacgtggcaggcaccgtgggtgccgatctc
tggcagggccagaggcgtgtgcagctgcgtgttctggacgcggctttcgcgccctga RecJ protein
SEQ ID NO: 22
MAMMEPADTVVRAFLSVERSATEQRWVSRLDQAAQNRALAMSQIHAIPELIARVLAGRGVGVDEALAFLDPTI
RSLMPDPHVLTDCEKAAERLVRAIETGEKVAIFGDYDVDGAASSALMYRFLAHFGLTPEIYIPDRIFEGYGPN
PAAMQQLAANGATLIVTVDCGSTSHESLNAAKDAGTDVVVIDHHQVGSELPPAVALVNPNREDDLSGQGHLCA
AGVVFLVLVATLRLLKDRRNRQAFTIDLLALLDIVALATVCDVVPLKGLNRAYVVKGLIAARHMNNAGLAALF
RKAGLSGQPVTPYHFGFLIGPRINAGGRIGDAALGSRLLTLDDSSQADVIAEKLDELNRERQAMEAVMLAEAEA
EALYEYGDGSGAGVIVTARENWHPGIVGLLASRLKDRFRRPAFAIAFDPSGKGTGSGRSINGFDMGRMVRAAV
DAGLLVKGGGHAMAAGLTVERANLGKLRTFFEEAAAKTVSELVESSVLKIDGAIGASGATLQLVDQLEQAGPY
GSGHSQPIFAVPAHRLRDVRLVGTSHVKITLEAMDGSRLDGIAFRAAEAPLGQMLLNARGRSIHVAGTVGADL
WQGQRRVQLRVLDAAFAP recN gene
SEQ ID NO: 23
atgctggtccagctctcgattcgtgacatcgttctgattgaaaggctcgacctcggctttgaggcgggcctt
ccgtgttgacgggtgagacgggcgcgggcaaatccattctgctttgacagcctgtcgctggcctcggggggccg
cggcgatggcggtctggtgcgccacggtgaagagaagggacaggtcactgccactttcgaagttccgaacagc
caccccacacggcatccctgcgcgaaaacggcctcgatgacgatggcgacctgattttccgccgcgtgcaat
ccgcagacggacgcaccaaggcctatatcaacgatcaggccatcagcgtgcagatgatgcgtcagctggggca
gctattggtcgaaattcacggccagcacgacgaccgcgctcgtgctcgataccgatgccaccgcacgctgctg
gatgctttcgccgggctgagcgacgatgcccgtgccgttcaggggttctaccgcacatggaaggacgccgagc
gggcattgaaaactcatcgtgccaaggttgaggctgctgcccgagaggcggactatctgcgttcctccgtcga
ggagcttgaggtgctctcgccgcgcgacggcgaggaggaggagcttgccgaacgtcgggcggtgatgcagaaa
tccgaacgtattgccggtgatatcgccgaagcgagcgagttcctgaacggcaacgcctcgccagtgccatga
tcgcatccatgatgcggcgcctggaacgcaagagccacgaggcgccggattgctggaagacaccgtgcaatt
gttggatgccgcgctcgacagcctttccaacgcgcagatggaagtggaggccgcacttcgccgcaccgagttc
gatccacgcgagctggagcgggtgaggaacggctgtttgcgctacgcgccgccggacgcaaatataatgtcg
cggtgcctgatctgccggcgattgcggaaaaaatggtcgcggatcttgccgacctcgatgcgggcgaagaaaa
gctcggcaaacttgaagccaatctcggcgttgtgaaagccaatttcgaccaccgcggccaaatcgcttttccgaa
aaacgccacaatgcggcgaacgcgctttccgaagctgtcatggcggagctttccggcgctcaagctggagcggg
cacgttttaccgtcgaagtcagctccgacccggagcaagcgacggctgacggtatcgacatcgtggaattcca
cgttcagaccaatcctggaacgcggcccgcccgatcatgaaagtcgcttctggcggcgaattgtcccgtttc
ctgctggcgcttaaagtcgcgctggcggatcgtggttcggccacgacactggtgttcgacgaaatcgacacgg
gcgttggcggcgctgtggcagatgcgcattggccaaaggctgcgtcgtctgtcgaaaaccgtgcaggttctgtc
cgtcacccacgcgccccaggtggccgcgggcggccacacatcttctcatttccaaaggcccctccggcgac
ggcaccgagcgcatcgccacgcgtgtcgctaccatggagccgaaacatcgcaccgaagaaatcgcccgcatgc
ttgccggtgcctcggtgacagatgaggcgagggctgctgccgcccgcctgcttgccgccaaggattaa RecN protein
SEQ ID NO: 24
MLVQLSIRDIVLIERLDLGFEAGLSVLTGETGAGKSILLDSLSLALGGRGDGGLVRHGEEKGQVTATFEVPNS
HPTRHLLRENGLDDDGDLIFRRVQSADGRTKAYINDQAISVQMMRQLGQLLVEIHGQHDDRALVDTDAHRTLL
DAFAGLSDDARAVQGFYRTWKDAERALKTHRAKVEAAAREADYLRSSVEELEVLSPRDGEEEELAERRAVMQK
SERIAGDIAEASEFLNGNASPVPMIASMMRRLERKSHEAPGLLEDTVQLLDAALDSLSNAQMEVEAALRRTEF DPRELERVEERLFALRAAGRKYNVAVPDLPAIAEKMVADLADLDAGEEKLGKLEANLGVVKANFDHAAKSLSE
KRHNAANALSEAVMAELPALKLERARFTVEVSSDPEQATADGIDIVEFHVQTNPGTRPGPIMKVASGGELSRF
LLALKVALADRGSAPTLVFDEIDTGVGGAVADAIGQRLRRLSKTVQVLSVTHAPQVAARAATHLLISKGPSGD
GTERIATRVATMEPKHRTEEIARMLAGASVTDEARAAAARLLAAKD recO gene

SEQ ID NO: 25 atgcagtggcaggacgaggcaatcattctcggcgtaaagcgtcatggcgagaccagcgtcatcgccgaggtga
tgacccgtttgcgcggccgccatctggggatggtgcgcggcgggcgctcccgcagcatgcagccggtgctgca
ggcgggaaaccgggtggatgtgatctggcgggcgcggcttgacgaccatctcggcgaattccgcattgagcct
ttgcagttgcgggcagcgcaattgatggaaacggcaaccgccgtgtatggcgtgcaggccatgggcgcgctgc
tgcggcttctgccggagcgtgacccgcatccgcatctctatcaggcgctcgacgtcattctcgacaatctcca
tgatccggtcgatgctggcgaattgttcgtacggttcgagctggcggtgctgaacgatcttggtttcggtctc
gatctcacggaatgcgcggcaacgggcctgcgcaccgatctcatctatgtatcgcccaaaacgggcagggcgg
tctgtagtacggcgggcgcgccctatgcggcgcgtatgctttcgcttcccgctttcctgagcgaaggtcagtc
gaaggcggccgaccgcgacagcctcgcggcagcctttcgcctgaccggccattttctccaccggcatgtctat
gatccgcgcggcctcaatgaaaacgccgcccgcgacggtttcgtgcaggcggcgttgaaggcactggagcgca
aggcggtgctgcctgcgctcgataaggcggtatag RecO protein

SEQ ID NO: 26

MQWQDEAIILGVKRHGETSVIAEVMTRLRGRHLGMVRGGRSRSMQPVLQAGNRVDVIWRARLDDHLGEFRIEP
LQLRAAQLMETATAVYGVQAMGALLRLLPERDPHPHLYQALDVILDNLHDPVDAGELFVRFELAVLNDLGFGL
DLTECAATGLRTDLIYVSPKTGRAVCSTAGAPYAARMLSLPAFLSEGQSKAADRDSLAAAFRLTGHFLHRHVY
DPRGLNENAARDGFVQAALKALERKAVLPALDKAV recQ gene

SEQ ID NO: 27 gtgaccaccgatcccttgcagattctcaagaccgtgtatggctacgatacgtttcgtggacagcaggccgaaa
tcatccggcatgtgatggcaggcaacaatgcatttgtattgatgccaacaggggcggaagtcgctttgtta
ccagattccggcgctcgcccgtaagggaatggggctggttgtttcgccctgatcgcgctgatggttgatcag
gtcgccgccttgcgtcaggcaggtgtgcgggcagaagctctcaactccgatctttcccagaagagcggcgga
tactctggcaggatatgcgggctggcaaggtcgatattctctatgccgcgccggagacccttctcaagccgga
tgttctggatgcgcttcaacctatcagcctgtcgctgatcgccatcgacgaagctcattgcctgtcgcagtgg
gggcacgatttccgtcccccttaccgccagctagacacgttgatcgagcgctttccggatacgcacgcatgg
cgctcacggcgactgcggacgagccaaccgcgccgaaattctgggtcatctcgggatcaacggaagcgacgc
cttcatagccggattcgatcggcaaatatccgctatgccagcagcatggaaaaggataatccacgtacgcagctg
aagcgcttcctgacgggtcgcgaggacgaaagcggcatcgtctattgccttttccaaacgcaaggtagatgaga
cggcggcctggctgcgtgaggagggcgcgatgcgctgccctatcacgccggcatggacaaggccgcccgcga
ggcgaaccagacccacttccagcatggtgaagctgtcatcatggttgcaaccgtggctttcggtatgggcatc
gacaaaccggatgtgcgcttcgttgtcatactgatctgccgcagcatgcgaagcctattatcaggaaaccg
gccgtgccggccgtgacggtctgccgtccgacgtgctctatgctttacggttatgaagacatcgcattgcgcaa
ccgctttatcgaagagtcggatgcgggcgaccagcgcaagaacatggagcgccgaagctcgatgcgttgctt
ggcctcgcgaaacagccggttgccgtcggcgggtgcttttgtcttatttcggcgaccattgtgagccctgcg
gcaattgcgacacctgtgcggagccgccggacctgtttgatggtgccattgccgccgcagaagttgctgtcctg
catttaccgcacgggagaacgtttcggccaggcctatgtcatccgctattgctgggcatggaagatgaacgg
atatcgaactttggtcacgatcggatcacgacctacggcatcggcaaagagcacgacaatcgcacctggcggg
ccatcctgcgccagatggttgcgctgcgcctgatcgaggttgatctggccggtcacggggggattgtccatttc
cgaagaagggaggcggttcctgcgcgaaaagccgtccctgatgttgaggataccgctccgctcccgttcggcg
cgacaacagacgaatcgcaagcccaccgccattgttctaccggatgccgatcgtagtctcttgaggcgctgc
gtgcgaagcgcatgaaattgcccgcgcacagaacgttccgccctatgtgatttttcacgacaagacactcat
tgagcttgcggcatcaagaccggcctctgtggggaaatggcgcagatacctggagtgggagacacaaagctg
gaacgatacggccctgctttctggcggcgatcatggaacatgccgccagcgagtga RecQ protein

SEQ ID NO: 28

VTTDPLQILKTVYGYDTFRGQQAEIIRHVMAGNNAFVLMPTGGGKSLCYQIPALARKGMGLVVSPLIALMVDQ
VAALRQAGVRAEALNSDLSPEERRILWQDMRAGKVDILYAAPETLLKPDVLDALQPISLSLIAIDEAHCLSQW
GHDFRPPYRQLDTLIERFPDTPRMALTATADEPTRAEILGHLGINGSDAFIAGFDRPNIRYAIMEKDNPRTQL
KRFLTGREDESGIVYCLSKRKVDETAAWLREEGRDALPYHAGMDKAAREANQTHFQHGEAVIMVATVAFGMGI
DKPDVRFVVHIDLPSSIEAYYQETGRAGRDGLPSDVLMLYGYEDIALRNRFIEESDAGDQRKNMERRKLDALL
GLAETAGCRRRVLLSYFGDHCEPCGNCDTCAEPPDLFDGAIAAQKLLSCIYRTGERFGQAYVIRVLLGMEDER
ISNFGHDRITTYGIGKEHDNRTWRAILRQMVALRLIEVDLAGHGGLSISEEGRRFLREKPSLMLRIPSAPRSA
RQQTNRKPTAIVLPDADRSLFEALRAKRMEIARAQNVPPYVIFHDKTLIELAASRPASVGEMAQIPGVGDTKL
ERYGPAFLAAIMEHAASE recR gene

SEQ ID NO: 29 atggcaaaacgagtcaccggtcccgaaatcgaaaaactgatccagctgcttgcaaaagtgccggggcttgggc
cccgctcggcgcggcgggcggcgctgcatctcatcaagaagaaggaacagcttcttggaccgctgggccacgc
gatgggtgaagcctatgacaaggtgaagatctgctcgtgctgcgcaatgtcgataccatcgatccctgcacg
gtctggccgatgatagacgtgaccagtcggtcatcatcgtgtcggaagacgtgtcggatctgtgggctcgggtgg
agcgagcaggcgcaatgaataccgcatatcatgtgcttggtggcacgctatcgccgctcgatggctcgggcc
ggaagatctgaacatcaagggactgatcgatcgcgtcagcgccggcggtattcgcgagctcatcatcgccgtc
aatgcgacggtggagggacaggcaacagcccattacatcaccgaccgcctggccgatctcggcatcaagatca
cccggcttgcgcatggcgtgcctgttggcggcgagctggactatctcgacgagggcacattgacggcggcgct
gcgcgctcgcacaacgatcga

Sequence listing

RecR protein
SEQ ID NO: 30
MAKRVTGPEIEKLIQLLAKVPGLGPRSARRAALHLIKKKEQLLGPLGHAMGEAYDKVKICSCCGNVDTIDPCT
VCADDRRDQSVINVEDVSDLWALERAGAMNTAYHVLGGTLSPLDGVGPEDLNIKGLIDRVSAGGIRELIIAVN
ATVEGQATAHYITDRLADLGIKITRLAHGVPVGGELDYLDEGTLTAALRARTTI recX gene
SEQ ID NO: 31
atgaccgatgattccagcccttcctgaccgacgacatggcactggatggcgaaacgcaggctatcgaaccca
ccagccgcatgctgtcatgggcgcgcaattccgctctctaccggctggaacagcgcatgatgacggaaaagca
gctgcgcgatgcgatcacccgcaaggcgcgggaaaaattcgaggatatcagcccgctcagataaaggcgctt
ggcgaattcgccgtgaccttcgcctatggcatcaaggcgctcgacgatacgcttatgcagaaattgccgtgc
gaagtggccagcgcagcggcaagtcgaagcgcgggcttgcgcagaaacttcagatcaagggcattgatcggga
aacggccgcagtcgcactgcaggaaaccaacgatctggtggcggccgtcatctttgcgcgcaagcgcgccttc
ggtcccttcgccgtgtcgagcttgatgaaaaacgcaagtcgaaggaattttctgccttcgcccgcaacggct
tcggcttcgaaatcggcgcgaaggtgatggcgatgacggtggaagaggcagaagagatcgtctcggaagcacc
gctttaa RecX protein
SEQ ID NO: 32
MTDDSSPFLTDDMALDGETQAIEPTSRMLSWARNSALYRLEQRMMTEKQLRDAITRKAREKFEDISPAQIKAL
GEFAVTFAYGIKALDDTAYAEIAVRSGQRSGKSKRGLAQKLQIKGIDRETAAVALQETNDLVAAVIFARKRAF
GPFRRVELDEKRKSKEFSAFARNGFGFEIGAKVMAMTVEEAEEIVSEAPL

What is claimed is:

1. A modified strain of *Agrobacterium tumefaciens*, wherein said modified strain is *A. tumefaciens* LBA4404 recA minus strain UIA777 or UIA770 as deposited with ATCC, and assigned Accession numbers PTA-123889 and PTA-123888, respectively.

2. The modified strain of claim 1, wherein the strain comprises a Ti plasmid.

3. A method of producing a transgenic plant, comprising:
   a. contacting targeted plant cells with a modified strain of *Agrobacterium tumefaciens* of claim 1;
   b. selecting and screening plant cells comprising DNA from said *Agrobacterium* strain integrated into genome of the targeted plant cells; and
   c. regenerating whole transgenic plants from plant cells selected/screened in step (b).

4. The method of claim 3, wherein the selecting step is carried out using a selectable marker comprising an antibiotic resistance gene selected from a chloramphenicol resistance gene, a kanamycin resistance gene, a spectinomycin resistance gene, a gentamycin resistance, or combinations thereof.

5. The method of claim 3, wherein said transgenic plant is selected from the group consisting of maize, soybean, rye, barley, cotton, and canola.

6. A composition comprising the modified *Agrobacterium tumefaciens* strain of claim 1, wherein the strain is further modified to comprise a binary vector for transformation of plants.

7. The composition of claim 6 wherein said binary vector comprises a gene encoding a product regulating an agronomic trait selected from the group consisting of an insecticidal resistance trait, herbicide tolerance trait, nitrogen use efficiency trait, water use efficiency trait, nutritional quality trait, DNA binding trait, selectable marker trait, or any combination thereof.

* * * * *